US009481878B2

(12) United States Patent
Chang et al.

(10) Patent No.: US 9,481,878 B2
(45) Date of Patent: *Nov. 1, 2016

(54) COMPOSITIONS AND METHODS OF USE OF IMMUNOTOXINS COMPRISING RANPIRNASE (RAP) SHOW POTENT CYTOTOXIC ACTIVITY

(71) Applicants: Immunomedics, Inc., Morris Plains, NJ (US); IBC Pharmaceuticals, Inc., Morris Plains, NJ (US)

(72) Inventors: Chien-Hsing Chang, Downingtown, PA (US); David M. Goldenberg, Mendham, NJ (US); Edmund A. Rossi, Woodland Park, NJ (US)

(73) Assignees: Immunomedics, Inc., Morris Plains, NJ (US); IBC Pharmaceuticals, Inc., Morris Plains, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/017,885

(22) Filed: Sep. 4, 2013

(65) Prior Publication Data

US 2014/0038261 A1 Feb. 6, 2014
US 2016/0257947 A9 Sep. 8, 2016

Related U.S. Application Data

(60) Continuation of application No. 12/871,345, filed on Aug. 30, 2010, now Pat. No. 8,551,480, which is a continuation-in-part of application No. 12/754,740, filed on Apr. 6, 2010, now Pat. No. 8,562,988, and a continuation-in-part of application No. 12/754,140, (Continued)

(51) Int. Cl.
| | |
|---|---|
| *A61K 39/395* | (2006.01) |
| *C07K 14/46* | (2006.01) |
| *C07K 16/28* | (2006.01) |
| *C12N 9/96* | (2006.01) |
| *A61K 39/00* | (2006.01) |
| *A61K 47/48* | (2006.01) |
| *A61K 51/08* | (2006.01) |
| *B82Y 5/00* | (2011.01) |
| *C07K 16/30* | (2006.01) |
| *C07K 16/46* | (2006.01) |
| *A61K 51/10* | (2006.01) |

(52) U.S. Cl.
CPC ............. *C12N 9/96* (2013.01); *A61K 39/0011* (2013.01); *A61K 47/4833* (2013.01); *A61K 47/48746* (2013.01); *A61K 51/088* (2013.01); *A61K 51/1027* (2013.01); *B82Y 5/00* (2013.01); *C07K 16/2803* (2013.01); *C07K 16/2833* (2013.01); *C07K 16/2887* (2013.01); *C07K 16/3007* (2013.01); *C07K 16/468* (2013.01); *A61K 2039/6056* (2013.01); *A61K 2039/625* (2013.01); *C07K 2317/31* (2013.01); *C07K 2317/55* (2013.01); *C07K 2317/77* (2013.01); *C07K 2317/92* (2013.01); *C07K 2319/00* (2013.01); *C07K 2319/30* (2013.01)

(58) Field of Classification Search
CPC .......... C07K 16/2833; C07K 16/2887; C07K 16/3007; C07K 16/468; C07K 16/2803; C07K 2317/55; C07K 2317/77; C07K 2317/92; C07K 2319/30; A61K 39/0011; A61K 47/4833; A61K 47/48746; A61K 51/088; A61K 2039/6056; A61K 2039/625; B82Y 5/00; C61K 2319/00

See application file for complete search history.

(56) References Cited

U.S. PATENT DOCUMENTS

| | | | |
|---|---|---|---|
| 4,046,722 A | 9/1977 | Rowland | |
| 4,699,784 A | 10/1987 | Shih et al. | |
| 4,818,709 A | 4/1989 | Primus et al. | |
| 4,868,109 A | 9/1989 | Lansdorp et al. | |
| 5,194,254 A | 3/1993 | Barber et al. | |
| 5,196,193 A | 3/1993 | Carroll | |
| 5,478,556 A | 12/1995 | Elliot et al. | |
| 5,530,101 A | 6/1996 | Queen et al. | |
| 5,571,515 A | 11/1996 | Scott et al. | |
| 5,585,089 A | 12/1996 | Queen et al. | |

(Continued)

FOREIGN PATENT DOCUMENTS

| | | |
|---|---|---|
| EP | 0324625 A1 | 7/1989 |
| EP | 0340793 B1 | 8/1995 |

(Continued)

OTHER PUBLICATIONS

Rossi et al., Blood vol. 114, No. 22 Nov. 20, 2009. Abstract No. 3721.*

(Continued)

*Primary Examiner* — Phuong Huynh
(74) *Attorney, Agent, or Firm* — Richard A. Nakashima

(57) ABSTRACT

The present invention concerns methods and compositions for forming immunotoxin complexes having a high efficacy and low systemic toxicity. In preferred embodiments, the toxin moiety is a ranpirnase (Rap), such as Rap(Q). In more preferred embodiments, the immunotoxin is made using dock-and-lock (DNL) technology. The immunotoxin exhibits improved pharmacokinetics, with a longer serum half-life and significantly greater efficacy compared to toxin alone, antibody alone, unconjugated toxin plus antibody or even other types of toxin-antibody constructs. In a most preferred embodiment the construct comprises an anti-Trop-2 antibody conjugated to Rap, although other combinations of antibodies, antibody fragments and toxins may be used to form the subject immunotoxins. The immunotoxins are of use to treat a variety of diseases, such as cancer, autoimmune disease or immune dysfunction.

3 Claims, 14 Drawing Sheets

Related U.S. Application Data filed on Apr. 5, 2010, now Pat. No. 8,722,047, and a continuation-in-part of application No. 12/752,649, filed on Apr. 1, 2010, now Pat. No. 8,034,352, which is a continuation-in-part of application No. 12/418,877, filed on Apr. 6, 2009, now Pat. No. 7,906,118, which is a continuation-in-part of application No. 11/389,358, filed on Mar. 24, 2006, now Pat. No. 7,550,143, and a continuation-in-part of application No. 11/478,021, filed on Jun. 29, 2006, now Pat. No. 7,534,866, and a continuation-in-part of application No. 12/396,605, filed on Mar. 3, 2009, now Pat. No. 7,858,070, which is a division of application No. 11/633,729, filed on Dec. 5, 2006, now Pat. No. 7,527,787, which is a continuation-in-part of application No. 11/478,021, said application No. 12/871,345 is a continuation-in-part of application No. 12/731,781, filed on Mar. 25, 2010, now Pat. No. 8,003,111, and a continuation-in-part of application No. 12/644,146, filed on Dec. 22, 2009, now Pat. No. 7,981,398, which is a division of application No. 11/925,408, filed on Oct. 26, 2007, now Pat. No. 7,666,400, which is a continuation-in-part of application No. 11/391,584, filed on Mar. 28, 2006, now Pat. No. 7,521,056, said application No. 12/871,345 is a continuation-in-part of application No. 12/544,476, filed on Aug. 20, 2009, now Pat. No. 7,901,680, and a continuation-in-part of application No. 12/537,803, filed on Aug. 7, 2009, now Pat. No. 8,491,896, which is a continuation-in-part of application No. 12/418,877, filed on Apr. 6, 2009, now Pat. No. 7,906,118, said application No. 12/871,345 is a continuation-in-part of application No. 12/479,250, filed on Jun. 5, 2009, now Pat. No. 8,192,739, which is a continuation of application No. 11/056,182, filed on Feb. 14, 2005, now Pat. No. 7,544,487, said application No. 12/871,345 is a continuation-in-part of application No. 12/418,877, and a continuation-in-part of application No. 12/468,589, filed on May 19, 2009, now Pat. No. 8,163,291, which is a division of application No. 11/389,358, said application No. 12/871,345 is a continuation-in-part of application No. 12/417,917, filed on Apr. 3, 2009, now Pat. No. 7,906,121, which is a division of application No. 11/478,021, which is a continuation-in-part of application No. PCT/US2006/010762, filed on Mar. 24, 2006, and a continuation-in-part of application No. PCT/US2006/012084, filed on Mar. 29, 2006, said application No. 12/871,345 is a continuation-in-part of application No. 12/396,965, filed on Mar. 3, 2009, now Pat. No. 7,871,622, which is a division of application No. 11/391,584, said application No. 12/871,345 is a continuation-in-part of application No. 12/396,605, which is a division of application No. 11/633,729, which is a continuation-in-part of application No. PCT/US2006/010762, and a continuation-in-part of application No. PCT/US2006/012084, and a continuation-in-part of application No. PCT/US2006/025499, filed on Jun. 29, 2006, and a continuation-in-part of application No. 11/389,358, and a continuation-in-part of application No. 11/391,584, and a continuation-in-part of application No. 11/478,021.

(60) Provisional application No. 61/168,290, filed on Apr. 10, 2009, provisional application No. 61/166,809, filed on Apr. 6, 2009, provisional application No. 61/168,715, filed on Apr. 13, 2009, provisional application No. 61/168,657, filed on Apr. 13, 2009, provisional application No. 61/168,668, filed on Apr. 13, 2009, provisional application No. 61/163,666, filed on Mar. 26, 2009, provisional application No. 60/668,603, filed on Apr. 6, 2005, provisional application No. 61/090,487, filed on Aug. 20, 2008, provisional application No. 61/104,916, filed on Oct. 13, 2008, provisional application No. 60/544,227, filed on Feb. 13, 2004, provisional application No. 61/043,932, filed on Apr. 10, 2008, provisional application No. 61/119,542, filed on Dec. 3, 2008, provisional application No. 60/782,332, filed on Mar. 14, 2005, provisional application No. 60/728,292, filed on Oct. 19, 2005, provisional application No. 60/751,196, filed on Dec. 16, 2005, provisional application No. 60/864,530, filed on Nov. 6, 2006, provisional application No. 61/238,473, filed on Aug. 31, 2009, provisional application No. 61/266,305, filed on Dec. 3, 2009, provisional application No. 61/316,996, filed on Mar. 24, 2010, provisional application No. 61/323,960, filed on Apr. 14, 2010.

(56) References Cited

U.S. PATENT DOCUMENTS

| | | |
|---|---|---|
| 5,614,610 A | 3/1997 | Hellstrom et al. |
| 5,693,762 A | 12/1997 | Queen et al. |
| 5,770,198 A | 6/1998 | Coller et al. |
| 5,789,554 A | 8/1998 | Leung et al. |
| 5,798,100 A | 8/1998 | Hansen |
| 5,859,205 A | 1/1999 | Adair et al. |
| 5,874,540 A | 2/1999 | Hansen et al. |
| 5,910,573 A | 6/1999 | Pluckthun et al. |
| 6,045,793 A | 4/2000 | Rybak et al. |
| 6,077,499 A | 6/2000 | Griffiths et al. |
| 6,132,718 A | 10/2000 | Hansen |
| 6,180,370 B1 | 1/2001 | Queen et al. |
| 6,180,377 B1 | 1/2001 | Morgan et al. |
| 6,187,287 B1 | 2/2001 | Leung et al. |
| 6,261,537 B1 | 7/2001 | Klaveness et al. |
| 6,306,393 B1 | 10/2001 | Goldenberg |
| 6,440,416 B1 | 8/2002 | Hansen et al. |
| 6,524,854 B1 | 2/2003 | Monia et al. |
| 6,617,135 B1 | 9/2003 | Gillies et al. |
| 6,730,300 B2 | 5/2004 | Leung et al. |
| 6,926,893 B1 | 8/2005 | Hansen |
| 7,022,500 B1 | 4/2006 | Queen et al. |
| 7,060,506 B2 | 6/2006 | Craig |
| 7,109,304 B2 * | 9/2006 | Hansen et al. ............ 530/387.3 |
| 7,151,164 B2 | 12/2006 | Hansen et al. |
| 7,312,318 B2 | 12/2007 | Hansen et al. |
| 7,354,587 B1 | 4/2008 | Hansen |
| 7,521,056 B2 | 4/2009 | Chang et al. |
| 7,527,787 B2 | 5/2009 | Chang et al. |
| 7,534,866 B2 | 5/2009 | Chang et al. |
| 7,541,440 B2 | 6/2009 | Goldenberg et al. |
| 7,550,143 B2 | 6/2009 | Goldenberg et al. |
| 7,666,400 B2 | 2/2010 | Chang et al. |
| 8,349,332 B2 | 1/2013 | Chang et al. |
| 8,551,480 B2 * | 10/2013 | Chang et al. ............ 424/134.1 |
| 2002/0040130 A1 | 4/2002 | Braun |
| 2003/0103979 A1 | 6/2003 | Leung et al. |
| 2003/0198956 A1 | 10/2003 | Makowski et al. |
| 2003/0228326 A1 | 12/2003 | Palomba et al. |
| 2003/0232420 A1 | 12/2003 | Braun et al. |
| 2004/0001825 A1 | 1/2004 | Govindan et al. |
| 2004/0018587 A1 | 1/2004 | Makowski et al. |
| 2005/0003403 A1 | 1/2005 | Rossi et al. |
| 2006/0210475 A1 | 9/2006 | Goldenberg et al. |
| 2006/0228300 A1 | 10/2006 | Chang et al. |
| 2007/0020259 A1 | 1/2007 | Hansen et al. |

(56) References Cited

U.S. PATENT DOCUMENTS

| | | |
|---|---|---|
| 2007/0086942 A1 | 4/2007 | Chang et al. |
| 2007/0140966 A1 | 6/2007 | Chang et al. |
| 2008/0171067 A1 | 7/2008 | Govindan et al. |
| 2009/0060862 A1 | 3/2009 | Chang et al. |
| 2009/0111143 A1 | 4/2009 | Goldenberg et al. |
| 2009/0191225 A1 | 7/2009 | Chang et al. |
| 2009/0246214 A1 | 10/2009 | Goldenberg et al. |
| 2010/0196266 A1 | 8/2010 | Goldenberg et al. |
| 2011/0158905 A1* | 6/2011 | Goldenberg et al. ........ 424/1.49 |
| 2011/0300066 A1 | 12/2011 | Chang et al. |
| 2011/0305631 A1 | 12/2011 | Govindan et al. |
| 2012/0276100 A1 | 11/2012 | Chang et al. |

FOREIGN PATENT DOCUMENTS

| | | |
|---|---|---|
| EP | 0438803 B1 | 3/1997 |
| EP | 0306995 B1 | 4/1997 |
| WO | 91/11465 A1 | 8/1991 |
| WO | 92/15322 A1 | 9/1992 |
| WO | 93/11162 A1 | 6/1993 |
| WO | 94/05329 A1 | 3/1994 |
| WO | 96/04313 A1 | 2/1996 |
| WO | 96/37224 A1 | 11/1996 |
| WO | 96/40941 A1 | 12/1996 |
| WO | 00/68248 | 11/2000 |
| WO | 03/074566 A1 | 9/2003 |
| WO | 2005/080586 | 9/2005 |
| WO | 2006/107617 | 10/2006 |
| WO | 2006/107786 | 10/2006 |
| WO | 2007/075270 | 7/2007 |
| WO | 2008/033413 | 3/2008 |
| WO | 2011025904 | 3/2011 |

OTHER PUBLICATIONS

Mecchia et al., "Type I consensus interferon (CIFN) gene transfer into human melanoma cells up-regulates p53 and enhances cisplatin-induced apoptosis: implications for new therapeutic strategies with IFN-alpha" Gene Ther. (2000) 7, 167-179.

Newlon et al., "A Novel Mechanism of PKA Anchoring Revealed by Solution Structures of Anchoring Complexes", Embo J. 2001; 20:1651-1662.

Newlon et al., "The molecular basis for protein kinase A anchoring revealed by solution NMR", Nature Struct. Biol. 1999; 3:222-227.

Ngo et al., "Computational Complexity, Protein Structure Prediction, and the Levinthal Paradox", The Protein Folding Problem and Tertiary Structure Prediction, Ch. 14, pp. 492-495, (Mertz & Le Grand, Eds.), Birkhauser Boston, 1994.

Osborn et al, "Pharmacokinetic and Pharmacodynamic Studies of a Human Serum Albumin-Interferon-α Fusion Protein in Cynomolgus Monkeys" J. Pharmacol. Exp. Ther. 303(2):540-548 (2002).

Oyen et al, "Human testis cDNA for the regulatory subunit RIIα of cAMP-dependent protein kinase encodes an alternate amino-terminal region", FEBS Letters 246:57-64, 1989.

Ozzello et al., "Conjugation of interferon alpha to a humanized monoclonal antibody (HuBrE-3vl) enhances the selective localization and antitumor effects of interferon in breast cancer xenografts" Breast Cancer Res. Treat. 48:135-147 (1998).

Paquette et al., "Interferon-α and granulocyte-macrophage colony-stimulating factor differentiate peripheral blood monocytes into potent antigen-presenting cells" J. Leukoc. Biol. 64:358-367; 1998.

Pelham et al., "Interferon-α conjugation to human osteogenic sarcoma monoclonal antibody 791T/36" Cancer Immunol. Immuother. 1983;15(3):210-216.

Pepinsky et al., "Improved Pharmacokinetic Properties of a Polyethylene Glycol-Modified Form of Interferon-β-1a with Preserved in Vitro Bioactivity" Pharmacol. Exp. Ther. 2001; 297(3):1059-1066.

Pilling et al., "Interferon-β mediates stromal cell rescue of T cells from apoptosis" Eur. J. Immunol. 29:1041-1050 (1999).

Rabjohn et al., "Molecular Cloning and Epitope Analysis of the Peanut Allergen Ara h 3" J. Clinical Investigation 103 (4):535-542 (1999).

Raefsky et al., "Studies of Interferon as a regulator of hematopoietic cells proliferation" J. Immunol. 135 (4):2507-2512 (1985).

Rose et al., "Structural basis of dimerization, coactivator recognition and MODY3 mutations in HNF-1α", Nature Struct. Biol. 2000; 7:744-748.

Rosendahl et al., "A Long-Acting, Highly Potent Interferon α-2 Conjugate Created Using Site-Specific PEGylation" Bioconjugate Chem. 2005;16:200-207.

Rossi et al., "Novel Designs of Multivalent Anti-CD20 Humanized Antibodies as Improved Lymphoma Therapeutics", Cancer Res. 68:8384-92, 2008.

Rossi et al., "Stably tethered multifunctional structures of defined composition made by the dock and lock method for use in cancer targeting" Proc. Natl. Acad. Sci. Epub Apr. 24, 2006, vol. 103, No. 18, pp. 6841-6846.

Rustandi et al., "The Ca2+-Dependent Interaction of S100B(ββ) with a Peptide Derived from p53", Biochemistry 1998; 37:1951-1960.

Sabaawy et al., "Enhancement of 5-fluorouracil cytotoxicity on human colon cancer cells by retrovirus-mediated interferon-αgene transfer" Int. J. Oncol. Jun. 1999; 14(6):1143-51.

Salles et al., "Rituximab combined with chemotherapy and interferon in follicular lymphoma patients: results of the GELA-GOELAMS FL2000 study" Blood 2008; 112:4824-4831.

Santini et al., "Type I Interferon as a Powerful Adjuvant for Monocyte-derived Dendritic Cell Development and Activity In Vivo and in Hu-PBL-SCID Mice" J. Exp. Med. 191(10):1777-1788 (2000).

Scott et al., "Type II Regulatory Subunit Dimerization Determines the Subcellular Localization of the cAMP-dependent Protein Kinase", J. Biol. Chem. 265:21561-66 (1990).

Scott et al., "Cyclic nucleotide-dependent protein kinases" Pharmacol. Ther. 1991;50(1):123-45.

Seffernick et al., "Melamine Deaminase and Atrazine Chlorohydrolase: 98 Percent Identical but Functionally Different" J. Bacteriol. 183(8):2405-2410 (2001).

Sharkey et al., "Improved Therapeutic Results by Pretargeted Radioimmunotherapy of Non-Hodgkin's Lymphoma with a New Recombinant, Trivalent, Anti-CD20, Bispecific Antibody", Cancer Res. 68:5282-90, 2008.

Sharkey et al., "Metastatic Human Colonic Carcinoma: Molecular Imaging with Pretargeted SPECT and PET in a Mouse Model", Radiology 246:497-507, 2008.

Sidky et al., "Inhibition of Angiogenesis by Interferons: Effects on Tumor- and Lymphocyte-induced Vascular Responses" Cancer Res. 47:5155-5161, Oct. 1, 1987.

Stein et al., "Characterization of a New Humanized Anti-CD20 Monoclonal Antibody, IMMU-106, and Its Use in Combination with the Humanized Anti-CD22 Antibody, Epratuzumab, for the Therapy of Non-Hodgkin's Lymphoma" Clin. Cancer Res. vol. 10, 2868-2878, Apr. 15, 2004.

Stein et al., "Characterization of a humanized IgG4 anti-HLA-DR monoclonal antibody that lacks effector cell functions but retains direct antilymphoma activity and increases the potency of rituximab" Blood 2006;108:2736-2744.

Stokka et al., "Characterization of A-kinase-anchoring disruption using a solution-based assay" Biochem. J. (2006) 400, 493-499.

Stryer et al., "Levels of Structure in Protein Architecture", Biochemistry, 3rd Ed., pp. 31-33, W.H. Freeman & Co., New York, 1988.

Takaoka et al., "Integration of interferon-α/β signalling to p53 responses in tumour suppression and antiviral defence" Nature Jul. 31, 2003;424(6948):516-23.

Taylor, S., "cAMP-dependent Protein Kinase" J. Biol. Chem. 1989;264(15):8443-8446.

Walsh et al., "An Adenosine 3', 5'-Monophosphate-dependant Protein Kinase from Rabbit Skeletal Muscle" J. Biol. Chem. 243(13):3763-3774 (1968).

(56) References Cited

OTHER PUBLICATIONS

Vanama et al., "Construction, characterization, and mammalian expression of an immunotoxin consisting of ranpirnase (Rap) fused to a humanized anti-EGP-1 antibody, hRS7, as a potential therapeutic for prostate cancer", Proc Amer Assoc Cancer Res, vol. 46, Abstr #679 (2005).
Weck et al., "Comparison of the Antiviral Activities of Various Cloned Human Interferon-α Subtypes in Mammalian Cell Cultures" J. Gen. Virol. (1981), 57, 233-237.
Winkler et al., "Changing the Antigen Binding Specificity by Single Point Mutations of an Anti-p24 (HIV-1) Antibody", J. Immunol. 165:4505-14, 2000.
Witkowski et al., "Conversion of a β-Ketoacyl Synthase to a Malonyl Decarboxylase by Replacement of the Active-Site Site Cysteine with Glutamine" Biochemistry 38(36):11643-50 (1999).
Wong et al., "AKAP Signalling Complexes: Focal Points in Space and Time", Nat. Rev. Mol. Cell Biol. 12:959-70 (2004).
Zhu et al., "Inhibition of tumor growth and metastasis by targeting tumor-associated angiogenesis with antagonists to the receptors of vascular endothelial growth factor", Invest. New Drugs 17:195-212, 1999.
Abbas et al., Cellular and Molecular Immunology, W.B. Saunders Comp. 1991, p. 43.
Alto et al., "Bioinformatic design of A-kinase anchoring protein-in silico: a potent and selective peptide antagonist of type II protein kinase A anchoring" Proc. Natl. Acad. Sci USA Apr. 15, 2003; 100(8):4445-50.
Backer et al., "Self-Assembled "Dock and Lock" System for Linking Payloads to Targeting Proteins" Bioconjugate Chem., 2006, 17(4):912-919.
Baillie et al., "Compartmentalisation of phospodiesterases and protein kinase A: opposites attract", FEBS Letters 2005; 579:3264-3270.
Banky et al., "Dimerization/Docking Domain of the Type Iα Regulatory Subunit of cAMP-dependent Protein Kinase", J. Biol. Chem. 273:35048-55, 1998.
Basu et al., "Structure-Function Engineering of Interferon-β-1b for Improving Stability, Solubility, Potency, Immunogenicity, and Pharmacokinetic Properties by Site-Selective Mono-PEGylation", Bioconjugate Chem. 2006; 17:618-630.
Belardelli et al., "Interferon-alpha in tumor immunity and immunotherapy" Cytokine Growth Factor Rev. 13(2):119-134 (2002).
Belardelli et al., "International Meeting on Cancer Vaccines: How Can We Enhance Efficacy of Therapeutic Vaccines?" Cancer Res. 64:6827-6830 (2004).
Belardelli et al., "The neglected role of type I interferon in the T-cell response: implications for its clinical use" Immunol. Today 17(8):369-72 (1996).
Biron et al., "Natural killer cells in antiviral defense: function and regulation by innate cytokines" Annu. Rev. Immunol. 17:189-220 (1999).
Brunda et al., "Modulation of Murine Natural Killer Cell Activity in Vitro and in Vivo by Recombinant Human Interferons" Cancer Res. 44:597-601 (1984).
Burns-Hamuro et al., "Distinct interaction modes of an AKAP bound to two regulatory subunit isoforms of protein kinase A revealed by amide hydrogen/deuterium exchange" Protein Science (2005), 14:2982-2992.
Carr et al., "Interaction of the Regulatory Subunit (RII) of cAMP-dependent Protein Kinase with RII-anchoring Proteins Occurs through an Amphipathic Helix Binding Motif", J. Biol. Chem. 266:14188-92 (1991).
Carr et al., "Identification of Sperm-specific Proteins That Interact with A-kinase Anchoring Proteins in a Manner Similar to the Type II Regulatory Subunit of PKA" J. Biol. Chem. 276(20):17332-17338 (2001).
Carrero et al., "Lymphocytes are detrimental during the early innate immune response against Listeria monocytogenes" J. Exp. Med. 203(4):933-940 (2006).
Chang et al., "The Dock and Lock Method: A Novel Platform Technology for Building Multivalent, Multifunctional Structures of Defined Composition with Retained Bioactivity" Clin. Cancer Res. Sep. 15, 2007;13(18 Suppl), pp. 5586-5591.
Chmura et al., "Antibodies with infinite affinity" Proc. Natl. Acad. Sci. USA 98(15):8480-8484 (2001).
Colledge et al., "AKAPs: from structure to function", Trends Cell Biol. 6:216-21 (1999).
Corbin et al., "Regulation of Adenosine 3',5'-Monophosphate-dependent Protein Kinase", J. Biol. Chem. 248:1813-21 (1973).
Dhalluin et al., "Structural and Biophysical Characterization of the 40 kDa PEG-Interferon-α2a and Its Individual Positional Isomers" Bioconjugate Chem. 2005;16:504-517.
Dodart et al., "Immunotherapy for Alzheimer's Disease: will vaccination work?" Trends Mol. Med. 9(3):85-87 (2003).
Doherty et al., "Site-Specific PEGylation of Engineered Cysteine Analogues of Recombinant Human Granulocyte-Macrophage Colony-Stimulating Factor", Bioconjugate Chem. 2005;16:1291-1298.
Ferrantini et al., "IFN-α 1 Gene Expression into a Metastatic Murine Adenocarcinoma (TS/A) Results in CD8+ T Cell-Mediated Tumor Rejection and Development of Antitumor Immunity" J. Immunol. 153:4604-15 (1994).
Ferrantini et al., "Interferon-α and cancer: Mechanisms of action and new perspectives of clinical use" Biochimie 89:884-893 (2007).
Gillies et al., "High-level expression of chimeric antibodies using adapted cDNA variable region cassettes", J. Immunol. Methods 125 (1989) 191-202.
Glennie et al., "Mechanisms of killing by anti-CD20 monoclonal antibodies" Mol. Immunol. 44:3823-3837 (2007).
Gold et al., "A Novel Bispecific, Trivalent Antibody Construct for Targeting Pancreatic Carcinoma", Cancer Res. 68:4819-26, 2008.
Gold et al., "Molecular Basis of AKAP Specificity for PKA Regulatory Subunits" Mol. Cell Nov. 3, 2006;24(3):383-95.
Goldenberg et al., "Multifunctional Antibodies by the Dock-and-Lock Method for Improved Cancer Imaging and Therapy by Pretargeting", J. Nucl. Med. 49:158-63, 2008.
Goldenberg et al., "Properties and structure-function relationships of veltuzumab (hA20), a humanized anti-CD20 monoclonal antibody" Blood 113:1062-70 (2009).
Goodson et al., "Site-Directed PEGylation of Recombinant Interleukin-2 at its Glycosylation Site", Nat. Biotechnology Apr. 1990;8(4):343-6.
Grace et al., "Site of Pegylation and Polyethylene Glycol Molecule Size Attenuate Interferon-α Antiviral and Antiproliferative Activities through the JAK/STAT Signaling Pathway" J. Biol. Chem. 2005;280(8):6327-6336.
Grimley et al., "Prolonged STAT1 Activation Related to the Growth Arrest of Malignant Lymphoma Cells by Interferon-α" Blood 91(8):3017-27 (1998).
Gutterman et al., "Leukocyte Interferon-Induced Tumor Regression in Human Metastatic Breast Cancer, Multiple Myeloma, and Malignant Lymphoma" Ann. Intern. Med. 93(3):399-406 (1980).
Gutterman et al., "Cytokine therapeutics: Lessons from interferon α" Proc. Natl. Acad. Sci. USA 91:1198-205 (1994).
Harris et al., "Effect of pegylation on pharmaceuticals" Nat. Rev. Drug. Discov. 2:214-221 (2003).
Hausken et al. "Mutational Analysis of the A-Kinase Anchoring Protein (AKAP)-binding Site on RII", J. Biol. Chem. 271:29016-22 (1996).
Hodneland et al., "Selective immobilization of proteins to self-assembled monolayers presenting active site-directed capture ligands", Proc. Natl. Acd. Sci. USA 2002; 99:5048-5052.
Huang et al., "Targeting IFN-α to B Cell Lymphoma by a Tumor-Specific Antibody Elicits Potent Antitumor Activities" J. Immunol. 179:6881-88 (2007).
Hundsrucker et al., "High-affinity AKAP7δ-protein kinase A interaction yields novel protein kinase A-anchoring disruptor peptides" Biochem. J. (2006) 396, 297-306.

(56) References Cited

OTHER PUBLICATIONS

Kimby et al., "Long-term molecular remissions in patients with indolent lymphoma treated with rituximab as a single agent or in combination with interferon alpha-2a: A randomized phase II study from the Nordic Lymphoma Group" Leuk. Lymphoma 49(1):102-112 (2008).
Kinderman et al., "A Dynamic Mechanism for AKAP Binding to RII Isoforms of cAMP-Dependent Protein Kinase" Mol. Cell 24(3):397-408 (2006).
Kinstler et al., "Characterization and Stability of N-terminally PEGylated rhG-CSF" Pharm. Res. 1996;13 (7):996-1002.
Kramer et al., "Cell and virus sensitivity studies with recombinant human alpha interferons" J. Interferon. Res. 3 (4):425-35 (1983).
Le Bon et al., "Type I Interferons Potently Enhance Humoral Immunity and Can Promote Isotype Switching by Stimulating Dendritic Cells In Vivo" Immunity 14:461-470 (2001).
Lee et al., "Solid-Phase PEGylation of Recombinant Interferon α-2a for Site-Specific Modification: Process Performance, Characterization, and in Vitro Bioactivity" Bioconjugate Chem. 2007; 18:1728-34.
Lohmann et al., "High-affinity binding of the regulatory subunit (RII) of cAMP-dependent protein kinase to microtubule-associated and other cellular proteins", Proc. Natl. Acad. Sci. USA 81:6723-27 (1984).
Luft et al., "Type I IFNs Enhance the Terminal Differentiation of Dendritic Cells" J. Immunol. 161:1947-1953 (1998).
Mason, Anthony J., "Functional Analysis of the Cysteine Residues of Activin A", Mol. Endocrinol. 8:325-32, 1994.
Matarrese et al., "Type I Interferon Gene Transfer Sensitizes Melanoma Cells to Apoptosis via a Target Activity on Mitochondrial Function" Am. J. Pathol. 2002, 160(4):1507-1520.
Altomonte et al., "Targeting of HLA-DR molecules transduces agonistic functional signals in cutaneous melanoma", J Cell Physiol. 2004;200:272-276.
Aoudjit et al., "HLA-DR signaling inhibits Fas-mediated apoptosis in A375 melanoma cells", Exp Cell Res. 2004;299:79-90.
ATCC Deposit HB55, deposited by LA Lampson on Dec. 14, 1981.
Blancheteau et al., "HLA class II signals sensitize B lymphocytes to apoptosis via Fas/CD95 by increasing FADD recruitment to activated Fas and activation of caspases", Hum Immunol. 2002;63:375-383.
Bridges et al., "Selective in vivo antitumor effects of monoclonal anti-I-A antibody on a B lymphoma", J Immunol. 1987;139:4242-4249.
Brozek et al., "Anti-DR antibodies inhibit in vitro production of human rheumatoid factor", J Clin Lab Immunol. 1990;31:105-109.
Elsasser et al., "HLA class II as potential target antigen on malignant B cells for therapy with bispecific antibodies in combination with granulocyte colony-stimulating factor", Blood 1996;87:3803-3812.
Fu et al., "HLA-DR alpha chain residues located on the outer loops are involved in non-polymorphic and polymorphic antibody-binding epitopes", Hum Immunol. 1994; 39:253-260.
Gussow et al., "Humanization of monoclonal antibodies", Method Enzymol. 203:99-121, (1991).
Kabelitz et al., "Growth inhibition of Epstein-Barr virus-transformed B cells by anti-HLA-DR antibody L243: possible relationship to L243-induced down-regulation of CD23 antigen expression", Cell Immunol. 1989;120:21-30.
Lampson et al., "Two populations of Ia-like molecules on a human B cell line", J. Immunol. (1980) 125:293-299.
Lund et al., "Expression and characterization of truncated forms of humanized L243 IgG1. Architectural features can influence synthesis of its oligosaccharide chains and affect superoxide production triggered through human Fcgamma receptor I", Eur. J. Biochem. Dec. 2000. vol. 267, No. 24, pp. 7246-7257.
Nagy et al., "Fully human, HLA-DR-specific monoclonal antibodies efficiently induce programmed death of malignant lymphoid cells", Nat Med. 2002;8:801-807.

Newton et al., "Potent and specific antitumor effects of an anti-CD22-targeted cytotoxic ribonuclease: potential for the treatment of non-Hodgkin lymphoma", Blood. Jan. 15, 2001;97(2):528-35.
Riemer et al., "Matching of trastuzumab (Herceptin) epitope mimics onto the surface of Her-2/neu—a new method of epitope definition", Mol Immunol. 2005 May;42(9):1121-4.
Roitt et al., Immunology, 3rd Ed., Mosby, London, 1993, p. 6.9.
Rosenthal et al., "Human tumor vaccines and genetic engineering of tumors with cytokine and histocompatibility genes to enhance immunogenicity", Curr. Opin. Oncol. 6:611-615 (1994).
Shan et al., "Constitutive Endocytosis and Degradation of CD22 by Human B Cells", J. Immunol. 154:4466-4475 (1995).
Stancovski et al., "Mechanistic aspects of the opposing effects of monoclonal antibodies to the ERBB2 receptor on tumor growth", Proc Natl Acad Sci USA. Oct. 1, 1991;88(19):8691-5.
Stein et al., "Neonatal administration of idiotype or antiidiotype primes for protection against *Escherichia coli* K13 infection in mice", J. Exp. Med. 160(4):1001-11 (1984).
Stein et al., "HLA-DR as a target for therapy of human and canine B-cell malignancies", Proc. Amer. Assoc. Cancer Res. 2009, 50:301, Abstr #1255.
Tedder et al., "Cloning of a complementary DNA encoding a new mouse B lymphocyte differentiation antigen, homologous to the human B1 (CD20) antigen, and localization of the gene to chromosome 19", J. Immunol. 141 (12):4388-94 (1988).
Traub et al., "Antiidiotype Antibodies in Cancer Patients Receiving Monoclonal Antibody to Carcinoembryonic Antigen", Cancer Res. 48:4002-4006 (1988).
Tsang et al., "A Recombinant CEA-Vaccinia Vaccine Induces a CEA-Specific Cytotoxic T-cell Response in Carcinoma Patients", Proc. Amer. Assoc. Cancer Res. vol. 36, p. 249, Abstract #1483 (1995).
Van Dijk et al., "Induction of tumor-cell lysis by bi-specific monoclonal antibodies recognizing renal-cell carcinoma and CD3 antigen", Int. J. Cancer 43:344-349 (1989).
Van Duk et al., "Bispecific antibodies reactive with the multidrug-resistance-related glycoprotein and CD3 induce lysis of multidrug-resistant tumor cells", Int. J. Cancer 44:738-743 (1989).
Van Kaer, L., "Accessory Proteins that Control the Assembly of MHC Molecules with Peptides", Immunologic Res. 23-2/3:205-214 (2001).
Vaswani et al., "Humanized antibodies as potential therapeutic drugs", Ann. Allergy Asthma Immunol. 1998; 81:105-119.
Waldmann et al., "Monoclonal Antibodies in Diagnosis and Therapy", Science 252:1657-1662 (1991).
Witkowski et al., "Conversion of a beta-ketoacyl synthase to a malonyl decarboxylase by replacement of the active-site cysteine with glutamine", Biochemistry. Sep. 7, 1999;38(36):11643-50.
Xu et al., "The Novelty of Antigen-Processing Compartments", J. Immunol. 155(4):1652-4 (1995).
Yu et al., "Peptide-antibody conjugates for tumour therapy: a MHC-class-II-restricted tetanus toxin peptide coupled to an anti-Ig light chain antibody can induce cytotoxic lysis of a human B-cell lymphoma by specific CD4 T cells", Int. J. Cancer 56:244-248 (1994).
Yu et al., "Interaction between bevacizumab and murine VEGF-A: a reassessment", Invest Ophthalmol Vis Sci. Feb. 2008;49(2):522-7.
Amigorena et al., "Transient accumulation of new class II MHC molecules in a novel endocytic compartment in B lymphocytes" Nature 369:113-120 (1994).
Becker et al., "Expression of a Hybrid Immunoglobulin-T Cell Receptor Protein in Transgenic Mice", Cell, 58:911-921 (Sep. 1989).
Becker, S., "Inteferon-γ Accelerates Immune Proliferation via Its Effect on Monocyte HLA-DR Expression", Cell. Immunol. Mar. 1985;91(1):301-7.
Bohlen et al., "Idiotype vaccination strategies against a murine B-cell lymphoma: Dendritic cells loaded with idiotype and bispecific idiotype x anti-class II antibodies can protect against tumor growth", Cytokines Mol. Ther. Dec. 1996;2(4):231-8.
Bolhuis et al., "T Cell Targeting in Cancer Therapy", Cancer Immunol. Immunother., 34:1-8 (1991).

(56) References Cited

OTHER PUBLICATIONS

Bolhuis et al., "Engineering T Lymphocyte Antigen Specificity", J. Cell. Biochem. 47:306-310, (1991).
Bremnes et al., "An LI and ML motif in the cytoplasmic tail of the MHC-associated invariant chain mediate rapid internalization", J. Cell. Science 107:2021-2032 (1994).
Burnett et al., " Human Monoclonal Antibodies to Defined Antigens", Human Hybridomas & Monoclonal Antibodies (Engelman et al, eds.) Plenum Press, New York, 1985, pp. 114-115.
Carayanniotis et al., "Delivery of synthetic peptides by anti-class II MHC monovalent antibodies induces specific adjuvant-free IgG responses in vivo", Mol. Immunol. 25(9):907-911 (1988).
Chen et al., "Novel strategies for improved cancer vaccines", Expert Rev. Vaccines 8(5):567-76 (2009).
Cohen et al., "Cancer Vaccines Get a Shot in the Arm", Science 262:841-843 (1993).
Durrant et al., "An idiotypic replica of carcinoembryonic antigen inducing cellular and humoral responses directed against human colorectal tumours", Int. J. Cancer 50:811-816 (1992).
Eshhar et al., "Chimeric T cell receptor which incorporates the anti-tumour specificity of a monoclonal antibody with the cytolytic activity of T cells: a model system for immunotherapeutical approach", Br. J. Cancer 62:27-29, 1990.
Eshhar et al., "Specific activation and targeting of cytotoxic lymphocytes through chimeric single chains consisting of antibody-binding domains and the γ or ζ subunits of the immunoglobulin and T-cell receptors", Proc. Natl. Acad. Sci. USA, 90:720-724 (1993).
Fagerberg et al., "Induction of an immune network cascade in cancer patients treated with monoclonal antibodies (ab1)", Cancer Immunol. Immunother. 37:264-270 (1993).
Fong et al., "Dendritic cell-based xenoantigen vaccination for prostate cancer immunotherapy", J. Immunol. 167 (12):7150-6 (2001).
Goldenberg et al., "Monoclonal Antibodies in Cancer Detection and Therapy", Am. J. Med. 94(3):297-312 (1993).
Goldenberg et al., "New Developments in Monoclonal Antibodies for Cancer Detection and Therapy", CA Cancer J. Clin. 44(1):43-64 (1994).
Goverman et al., "Chimeric immunoglobulin-T cell receptor proteins form functional receptors: implications for T cell receptor complex formation and activation", Cell 60:929-939 (1993).
Gross et al., "Generation of effector T cells expressing chimeric T cell receptor with antibody type-specificity", Transp. Proc. 21(1):127-130 (Feb. 1989).
Gross et al., "Expression of immunoglobulin-T-cell receptor chimeric molecules as functional receptors with antibody-type specificity", Proc. Natl. Acad. Sci. USA 86:10024-10028 (Dec. 1989).
Hefta et al., "Expression of Carcinoembryonic Antigen and Its Predicted Immunoglobulin-like Domains in HeLa Cells for Epitope Analysis", Cancer Res. 52:5647-5655 (1992).
Herlyn et al., "Specific detection of anti-idiotypic immune responses in cancer patients treated with murine monoclonal antibody", J. Immunol. Methods 85:27-38 (1985).
Herlyn et al., "Anti-idiotype immunization of cancer patients: Modulation of the immune response", Proc. Natl. Acad. Sci. USA 84:8055-8059 (1987).
Ikeda et al., "Epitope mapping of the carcinoembryonic antigen with various related recombinant proteins expressed in chinese hamster ovary cells and 25 distinct monoclonal antibodies", Mol. Immunol. 29(2):229-240 (1992).
Ioannides et al., "T cell recognition of human tumors: implications for molecular immunotherapy of cancer", Clin. Immunol. Immunopath. 66:91-106 (Feb. 1993).
Irvine et al., "Comparison of CEA-Recombinant Vaccinia Virus, Purified CEA, and an Anti-Idiotype Antibody Bearing the Image of a CEA Epitope in the Treatment and Prevention of CEA-Expressing Tumors", Vaccine Res. 2(2):79-94 (1993).

Kennedy et al., "Antibody to Hepatitis B Virus Induced by Injecting Antibodies to the Idiotype", Science 223:930-931 (1984).
Kos et al., "Requirement for Natural Killer Cells in the Induction of Cytotoxic T Cells", J. Immunol. 155:578-584 (1995).
Kresina et al., "Antiidiotypic Antibody Vaccine in Murine Schistosomiasis mansoni Comprising the Internal Image of Antigen", J. Clin. Invest. 83:912-920 (1989).
Lanzavecchia et al., "The use of hybrid hybridomas to target human cytotoxic T lymphocytes", Eur. J. Immun. 17:105-111 (1987).
Losman et al., "Baboon anti-idiotype antibodies mimic a carcinoembryonic antigen epitope", Int. J. Cancer 46:310-314 (1990).
Losman et al., "Human response against NP-4, a mouse antibody to carcinoembryonic antigen: Human anti-idiotype antibodies mimic an epitope on the tumor antigen", Proc. Natl. Acad. Sci. USA 88:3421-3425 (Apr. 1991).
Losman et al., "Mimicry of a carcinoembryonic antigen epitope by a rat monoclonal anti-idiotype antibody", Int. J. Cancer 56:580-584 (1994).
Machy et al., "Endocytosis and recycling of MHC-encoded class II molecules by mouse B lymphocytes", J. Immunol. 145(5):1350-1355 (1990).
McNamara et al., "Monoclonal Idiotype Vaccine Against *Streptococcus pneumoniae* Infection", Science 226:1325-1326 (1984).
Mittelman et al., "Kinetics of the immune response and regression of metastatic lesions following development of humoral anti-high molecular weight-melanoma associated antigen immunity in three patients with advanced malignant melanoma immunized with mouse antiidiotypic monoclonal antibody MK2-23", Cancer Res. 54:415-421(1994).
Moldenhauer et al., "Surface-expressed invariant chain (CD74) is required for internalization of human leucocyte antigen-DR molecules to early endosomal compartments", Immunol. 96:473-484 (1999).
Monestier et al., "Syngeneic Anti-idotype Monoclonal Antibodies to Murine Anticarcinoembryonic Antigen Monoclonal Antibodies", Cancer Res. 49:123-126 (1989).
Morton et al., Delivery of Nascent MHC Class II-Invariant Chain Complexes to Lysosomal Compartments and Proteolysis of Invariant Chain by Cysteine Proteases Preceded Peptide Binding in B-Lymphoblastoid Cells, J. Immunol. 154:137-150 (1995).
Nepom et al., "Induction of immunity to a human tumor marker by in vivo administration of anti-idiotypic antibodies in mice", Proc. Natl. Acad. Sci. USA 81:2864-2867 (1984).
Nohria et al., "Cytokines as potential vaccine adjuvants", Biotherapy 7:261-269 (1994).
Pathak et al., "Endocytic Recycling is Required for the Presentation of an Exogenous Peptide via MHC Class II Molecules", Traffic 1:561-569 (2000).
Paul, W., (ed.), Fundamental Immunology, 3rd Ed., Raven Press, New York, 1993, p. 242.
Pawlak-Byczkowska et al. "Two New Monoclonal Antibodies, EPB-1 and EPB-2, Reactive with Human Lymphoma", Cancer Res. 49:4568-4577 (1989).
Powell et al., "Induction of effective immunity to moloney murine sarcoma virus using monoclonal anti-idiotypic antibody as immunogen", J. Immunol. 142(4):1318-1324 (1989).
Primus et al., "Immunological Heterogeneity of Carcinoembryonic Antigen: Antigenic Determinants on Carcinoembryonic Antigen Distinguished by Monoclonal Antibodies", Cancer Res. 43:686-692 (1983).
Pupa et al., "Activation of mononuclear cells to be used for hybrid monoclonal antibody-induced lysis of human ovarian carcinoma cells", Int. J. Cancer 42:455-459 (1988).
Renner et al., "Cure of xenografted human tumors by bispecific monoclonal antibodies and human T cells", Science 264:833-835 (1994).
Roche et al., "Cell surface HLA-DR-invariant chain complexes are targeted to endosomes by rapid internalization", Proc. Natl. Acad. Sci. USA 90:8581-8585 (1993).

(56) References Cited

OTHER PUBLICATIONS

Cardillo et al., "Abstract 5346: A novel immunotoxin comprising quadruple RNase tethered to an internalizing anti-TROP-2 humanized MAb shows potent cytotoxicity against diverse solid tumors in vitro", Cancer Res., Apr. 15, 2010, Retrieved from the Internet: URL:http://cancerres.aacrjournals.org/content/70/8_Supplement/5346.abstract.

Rossi et al., "A Novel Ribonuclease-Based Immunotoxin Comprising Quadruple Ranpirnase (Rap) Site-Specifically Conjugated to an Anti-CD22 IgG Showing Ptent Anti-Lymphoma Activity", Blood, American Society of Hematology, U.S., vol. 114, No. 22, p. 1433, Nov. 1, 2009.

Rossi et al., "Abstract 5345: Potent ribonuclease-based immunotoxins comprising quadruple ranpirnase (Rap) site-specifically conjugated to B-cell lymphoma-targeting antibodies", Cancer Res, Apr. 15, 2010, Retrieved from the Internet: URL:http://cancerres.aacrjournals.org/content/70/8_Supplement/5345.abstract.

\* cited by examiner

COMPOSITIONS AND METHODS OF USE OF IMMUNOTOXINS COMPRISING RANPIRNASE (RAP) SHOW POTENT CYTOTOXIC ACTIVITY

CROSS REFERENCE TO RELATED APPLICATIONS

This application is a continuation of U.S. patent application Ser. No. 12/871,345, filed Aug. 30, 2010, which was a continuation-in-part of U.S. patent application Ser. No. 12/754,740, filed Apr. 6, 2010; Ser. No. 12/754,140, filed Apr. 5, 2010; Ser. No. 12/752,649 (now U.S. Pat. No. 8,034,352), filed Apr. 1, 2010; Ser. No. 12/731,781 (now U.S. Pat. No. 8,003,111), filed Mar. 25, 2010; Ser. No. 12/644,146 (now U.S. Pat. No. 7,981,398) (which was a divisional of U.S. Pat. No. 7,666,400), filed Dec. 22, 2009; 12/544,476 (now U.S. Pat. No. 7,901,680), filed Aug. 20, 2009; Ser. No. 12/537,803 (now U.S. Pat. No. 8,491,896), filed Aug. 7, 2009; Ser. No. 12/479,250 (now U.S. Pat. No. 8,192,739) (which was a continuation of U.S. Pat. No. 7,544,487), filed Jun. 5, 2009; Ser. No. 12/468,589 (now U.S. Pat. No. 8,163,291) (which was a divisional of U.S. Pat. No. 7,550,143), filed May 19, 2009; Ser. No. 12/418,877 (now U.S. Pat. No. 7,906,118), filed Apr. 6, 2009; Ser. No. 12/417,917 (now U.S. Pat. No. 7,906,121) (which was a divisional of U.S. Pat. No. 7,534,866), filed Apr. 3, 2009; Ser. No. 12/396,965 (now U.S. Pat. No. 7,871,622) (which was a divisional of U.S. Pat. No. 7,521,056), filed Mar. 3, 2009; and Ser. No. 12/396,605 (now U.S. Pat. No. 7,858,070) (which was a divisional of U.S. Pat. No. 7,527,787), filed Mar. 3, 2009. Those applications claimed the benefit under 35 U.S.C. 119(e) of provisional U.S. Patent Applications 61/168,715, filed Apr. 13, 2009; 61/168,668, filed Apr. 13, 2009; 61/168,657, filed Apr. 13, 2009; 61/168,290, filed Apr. 10, 2009; 61/166,809, filed Apr. 6, 2009; 61/163,666, filed Mar. 26, 2009; 61/119,542, filed Dec. 3, 2008; 61/104,916, filed Oct. 13, 2008; 61/090,487, filed Aug. 20, 2008; 61/043,932, filed Apr. 10, 2008; 60/864,530, filed Nov. 6, 2006; 60/782,332, filed Mar. 14, 2006; 60/751,196, filed Dec. 16, 2005; 60/728,292, filed Oct. 19, 2005; 60/668,603, filed Apr. 6, 2005; and 60/544,227, filed Feb. 13, 2004. This application claims the benefit under 35 U.S.C. 119(e) of U.S. Provisional Patent Application Nos. 61/238,473, filed Aug. 31, 2009; 61/266,305, filed Dec. 3, 2009; 61/316,996, filed Mar. 24, 2010; and 61/323,960, filed Apr. 14, 2010. Each priority application is incorporated herein by reference in its entirety.

GOVERNMENT FUNDING

This work was supported in part by grant 2R44CA108083-02A2 from the National Cancer Institute, National Institutes of Health. The federal government may have certain rights in the invention.

SEQUENCE LISTING

The instant application contains a Sequence Listing which has been submitted in ASCII format via EFS-Web and is hereby incorporated by reference in its entirety. Said ASCII copy, created on Sep. 15, 2010, is named IMM321US.txt and is 42,529 bytes in size

FIELD

The present invention relates to compositions and methods of use of toxin-antibody constructs (immunotoxins), preferably comprising ranpirnase (Rap), although the skilled artisan will realize that a wide variety of toxins and other cytotoxic agents are known in the art and any such toxin or cytotoxic agent may be utilized in the claimed compositions and methods. In other preferred embodiments, the constructs comprise anti-tumor antibodies, such as anti-EGP-1 (anti-Trop-2), anti-CD74, anti-CD22 or anti-CD20. However, the compositions and methods are not so limited and the antibody or antibody fragment may bind to an antigen associated with any target tissue, such as a cancer cell, a B cell, a T cell, an autoimmune disease cell, a pathogen, or any other disease-associated target cell for which antibodies are known in the art.

In more preferred embodiments, the immunotoxins are dock-and-lock (DNL) constructs, preferably comprising four copies of ranpirnase attached to an antibody or antibody fragment. Even more preferably, the toxins or other cytotoxic agents are fusion proteins, each comprising a DDD (dimerization and docking domain) moiety and the antibody or antibody fragment is a fusion protein comprising two AD (anchoring domain) moieties. The DDD moieties spontaneously form dimers which bind to an AD moiety, producing a DNL construct comprising four copies of the cytotoxin conjugated to one antibody or antibody fragment. The resulting immunotoxins show highly potent cytotoxic activity and may be administered to a subject with a disease to kill disease associated cells. The immunotoxins show greater potency against target cells than the parent antibody alone, the cytotoxin alone, a non-conjugated combination of antibody and cytotoxin or cytotoxin conjugated to a control antibody.

BACKGROUND

Ribonucleases, in particular, Rap (Lee, Exp Opin Biol Ther 2008; 8:813-27) and its more basic variant, amphinase (Ardelt et al., Curr Pharm Biotechnol 2008:9:215-25), are potential anti-tumor agents (Lee and Raines, Biodrugs 2008; 22:53-8). Rap is a single-chain ribonuclease of 104 amino acids originally isolated from the oocytes of *Rana pipiens*. Rap exhibits cytostatic and cytotoxic effects on a variety of tumor cell lines in vitro, as well as antitumor activity in vivo. The amphibian ribonuclease enters cells via receptor-mediated endocytosis and once internalized into the cytosol, selectively degrades tRNA, resulting in inhibition of protein synthesis and induction of apoptosis.

Rap has completed a randomized Phase IIIb clinical trial, which compared the effectiveness of Rap plus doxorubicin with that of doxorubicin alone in patients with unresectable malignant mesothelioma, with the interim analysis showing that the MST for the combination was 12 months, while that of the monotherapy was 10 months (Mutti and Gaudino, Oncol Rev 2008; 2:61-5). Rap can be administered repeatedly to patients without an untoward immune response, with reversible renal toxicity reported to be dose-limiting (Mikulski et al., J Clin Oncol 2002; 20:274-81; Int J Oncol 1993; 3:57-64).

Rap and other toxins or cytotoxins may be conjugated to antibodies or antibody fragments for targeted delivery to selected disease-associated cells, such as cancer cells or autoimmune disease cells. An exemplary tumor-associated antigen is EGP-1, also known as Trop-2.

Trop-2 is a type-I transmembrane protein and has been cloned from both human (Formaro et al., Int J Cancer 1995; 62:610-8) and mouse cells (Sewedy et al., Int J Cancer 1998; 75:324-30). In addition to its role as a tumor-associated calcium signal transducer (Ripani et al., Int J Cancer 1998;

76:671-6), the expression of human Trop-2 was shown to be necessary for tumorigenesis and invasiveness of colon cancer cells, which could be effectively reduced with a polyclonal antibody against the extracellular domain of Trop-2 (Wang et al., Mol Cancer Ther 2008; 7:280-5).

The growing interest in Trop-2 as a therapeutic target for solid cancers (Cubas et al., Biochim Biophys Acta 2009; 1796:309-14) is attested by further reports that documented the clinical significance of overexpressed Trop-2 in breast (Huang et al., Clin Cancer Res 2005; 11:4357-64), colorectal (Ohmachi et al., Clin Cancer Res 2006; 12:3057-63; Fang et al., Int J Colorectal Dis 2009; 24:875-84), and oral squamous cell (Fong et al., Modern Pathol 2008; 21:186-91) carcinomas. The latest evidence that prostate basal cells expressing high levels of Trop-2 are enriched for in vitro and in vivo stem-like activity is particularly noteworthy (Goldstein et al., Proc Natl Acad Sci USA 2008; 105:20882-7).

The murine anti-Trop-2 mAb, mRS7, was generated by hybridoma technology using a crude membrane preparation derived from a surgically removed human primary squamous cell carcinoma of the lung as immunogen (Stein et al., Cancer Res 1990; 50:1330-6). Immunoperoxidase staining of frozen tissue sections indicated that the antigen defined by mRS7 is present in tumors of the lung, stomach, bladder, breast, ovary, uterus, and prostate, with most normal human tissues being unreactive (Stein et al., Int J Cancer 1993; 55:938-46). The antigen recognized by mRS7 was later shown to be a 46-48 kDa glycoprotein and named epithelial glycoprotein-1, or EGP-1 (Stein et al., Int J Cancer 1994; 8:98-102), which is also referred to in the literature as Trop-2 (Ripani et al., Int J Cancer 1998; 76:671-6). Upon binding to the target cells, mRS7 is rapidly internalized within 2 h (Stein et al., Int J Cancer 1993; 55:938-46).

Radiolabeled mRS7 has been shown to effectively target and treat cancer xenografts in nude mice in several earlier studies (Stein et al., Antibody Immunoconj Radiopharm 1991; 4:703-12; Stein et al., Cancer 1994; 73:816-23; Shih et al., Cancer Res 1995; 55:5857s-63s; Stein et al., J Nucl Med 2001; 42:967-74; Stein et al., Crit. Rev Oncol Hematol 2001; 39:173-80). However, a need exists in the field for immunoconjugates ("immunotoxins") of RS7 or other disease-targeting antibodies that may be attached to Rap or other cytotoxins to provide a more efficacious agent for disease therapy.

SUMMARY

The present invention concerns compositions and methods of use of immunotoxins comprising Ranpirnase (Rap) or other toxins, conjugated to a disease-targeting antibody or antigen-binding antibody fragment. In certain preferred embodiments, the immunotoxin may be of a structure as illustrated in FIG. 1, referred to as 2L-Rap(Q)-hRS7 or 2L-Rap-hRS7, comprising two copies of Rap attached to the N-terminal ends of a humanized anti-Trop-2 antibody (hRS7). However, the skilled artisan will realize that the immunotoxins are not so limited and antibodies against other tumor-associated or disease-associated antigens known in the art may be utilized. Such immunotoxins exhibit potent cytotoxicity and improved pharmacokinetics, while minimizing the toxic side effects of Rap.

In alternative embodiments, the subject immunotoxin may be made using the dock-and-lock (DNL) technology and may comprise conjugates of antibodies or antigen-binding antibody fragments with Rap or other toxins or cytotoxins. As used herein below, the term "immunotoxin" may refer to an immunotoxin made by the DNL technique, or an immunotoxin as illustrated in FIG. 1. In preferred embodiments, the DNL constructs comprise Rap conjugated to an anti-Trop-2 antibody, such as hRS7. However, the skilled artisan will be aware that the DNL constructs are not so limited and the subject DNL constructs may comprise an antibody or fragment thereof against any disease-associated antigen, conjugated to ranpirnase or other toxins or cytotoxins known in the art.

In particular embodiments, the immunotoxin may comprise a humanized anti-Trop-2 antibody or fragment thereof, such as an hRS7 antibody comprising the heavy chain CDR sequences CDR1 (NYGMN, SEQ ID NO:1), CDR2 (WIN-TYTGEPTYTDDFKG, SEQ ID NO:2) and CDR3 (GGF-GSSYWYFDV, SEQ ID NO:3) and the light chain CDR sequences CDR1 (KASQDVSIAVA, SEQ ID NO:4), CDR2 (SASYRYT, SEQ ID NO:5), and CDR3 (QQHYITPLT, SEQ ID NO:6), attached to human antibody framework (FR) and constant region sequences (see, e.g., U.S. Pat. No. 7,238,785, incorporated herein by reference from Col. 34, line 6 to Col. 44, line 37).

In other particular embodiments, the immunotoxin may comprise a humanized anti-CD20 antibody or fragment thereof, such as veltuzumab, comprising light chain variable region CDR1 (RASSSVSYIH, SEQ ID NO:7); CDR2 (ATSNLAS, SEQ ID NO:8); and CDR3 (QQWTSNPPT, SEQ ID NO:9); and heavy chain variable region CDR1 (SYNMH, SEQ ID NO:10); CDR2 (AIYPGNGDTSYNQK-FKG, SEQ ID NO:11); and CDR3 (STYYGGDWYFDV (SEQ ID NO: 95) or VVYYSNSYWYFDV, SEQ ID NO:12) (see, e.g., U.S. Pat. No. 7,435,803, incorporated herein by reference from Col. 38, line 15 to Col. 46, line 52).

In more particular embodiments, the immunotoxin may comprise a ranpirnase (Rap) amino acid sequence, as is known in the art (see, e.g. NCBI protein database Accession No. 1PU3_A, see also Gorbatyuk et al., J Biol Chem 279:5772-80, 2004).

In various embodiments, the immunotoxins may comprise one or more antibodies or fragments thereof which bind to an antigen other than Trop-2 or CD20. In preferred embodiments, the antigen(s) may be selected from the group consisting of carbonic anhydrase IX, CCL19, CCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, AFP, PSMA, CEACAM5, CEACAM-6, B7, ED-B of fibronectin, Factor H, FHL-1, Flt-3, folate receptor, GROB, HMGB-1, hypoxia inducible factor (HIF), HM1.24, insulin-like growth factor-1 (ILGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-1A, MIP-1B, MIF, MUC1, MUC2, MUC3, MUC4, MUC5, PAM4 antigen, NCA-95, NCA-90, Ia, HM1.24, EGP-1, EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, P1GF, complement factors C3, C3a, C3b, C5a, C5, and an oncogene product.

Exemplary antibodies that may be utilized include, but are not limited to, hR1 (anti-IGF-1R, U.S. patent application Ser. No. 12/722,645, filed Mar. 12, 2010), hPAM4 (anti-mucin, U.S. Pat. No. 7,282,567), hA20 (anti-CD20, U.S. Pat. No. 7,151,164), hA19 (anti-CD19, U.S. Pat. No. 7,109, 304), hIMMU31 (anti-AFP, U.S. Pat. No. 7,300,655), hLL1 (anti-CD74, U.S. Pat. No. 7,312,318), hLL2 (anti-CD22, U.S. Pat. No. 6,187,287), hMu-9 (anti-CSAp, U.S. Pat. No. 7,387,772), hL243 (anti-HLA-DR, U.S. Pat. No. 7,612,180), hMN-14 (anti-CEACAM5, U.S. Pat. No. 6,676,924), hMN-15 (anti-CEACAM6, U.S. Pat. No. 7,541,440), hRS7 (anti-EGP-1, U.S. Pat. No. 7,238,785) and hMN-3 (anti-CEACAM6, U.S. Pat. No. 7,541,440) the Examples section of each cited patent or application incorporated herein by reference. The skilled artisan will realize that this list is not limiting and that any known antibody may be used, as discussed in more detail below.

Exemplary toxins that may be incorporated into the immunotoxins include but are not limited to a bacterial toxin, a plant toxin, ricin, abrin, alpha toxin, saporin, ribonuclease (RNase), DNase 1, Staphylococcal enterotoxin-A, pokeweed antiviral protein, gelonin, diphtheria toxin, *Pseudomonas* exotoxin, *Pseudomonas* endotoxin, Ranpirnase (Rap) and Rap (N69Q). The sequences of each of the recited toxins is known in the art (see for example NCBI database) and clones encoding many of the exemplary toxins are commercially available from Invitrogen, the American Type Culture Collection and other sources known in the art.

Various embodiments may concern use of the subject immunotoxins to treat or diagnose a disease, including but not limited to non-Hodgkin's lymphomas, B cell acute and chronic lymphoid leukemias, Burkitt lymphoma, Hodgkin's lymphoma, hairy cell leukemia, acute and chronic myeloid leukemias, T cell lymphomas and leukemias, multiple myeloma, glioma, Waldenstrom's macroglobulinemia, carcinomas, melanomas, sarcomas, gliomas, and skin cancers. The carcinomas may be selected from the group consisting of carcinomas of the oral cavity, gastrointestinal tract, colon, stomach, pulmonary tract, lung, breast, ovary, prostate, uterus, endometrium, cervix, urinary bladder, pancreas, bone, liver, gall bladder, kidney, skin, and testes. In addition, the subject immunotoxins may be used to treat an autoimmune disease, for example acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, or fibrosing alveolitis. In certain embodiments, the subject antibodies may be used to treat leukemia, such as chronic lymphocytic leukemia, acute lymphocytic leukemia, chronic myeloid leukemia or acute myeloid leukemia.

In one embodiment, a pharmaceutical composition of the present invention may be use to treat a subject having a metabolic disease, such amyloidosis, or a neurodegenerative disease, such as Alzheimer's disease. In addition, a pharmaceutical composition of the present invention may be used to treat a subject having an immune-dysregulatory disorder.

The compositions of the present invention also are useful for the therapeutic treatment of infections, where the immunoglobulin component of the immunotoxin specifically binds to a disease-causing microorganism. In the context of the present invention a disease-causing microorganism includes pathogenic bacteria, viruses, fungi and diverse parasites, and the antibody can target these microorganisms, their products or antigens associated with their lesions. Examples of microorganisms include, but are not limited to: *Streptococcus agalactiae, Legionella pneumophilia, Streptococcus pyogenes, Escherichia coli, Neisseria gonorrhoeae, Neisseria meningitidis, Pneumococcus, Hemophilis influenzae B, Treponema pallidum, Lyme disease spirochetes, Pseudomonas aeruginosa, Mycobacterium leprae, Brucella abortus, Mycobacterium tuberculosis, Tetanus toxin*, HIV-1, -2, -3, Hepatitis A, B, C, D, Rabies virus, Influenza virus, Cytomegalovirus, Herpes simplex I and II, Human serum parvo-like virus, Papilloma viruses, Polyoma virus, Respiratory syncytial virus, Varicella-Zoster virus, Hepatitis B virus, Papilloma virus, Measles virus, Adenovirus, Human T-cell leukemia viruses, Epstein-Barr virus, Murine leukemia virus, Mumps virus, Vesicular stomatitis virus, Sindbis virus, Lymphocytic choriomeningitis virus, Wart virus, Blue tongue virus, Sendai virus, Feline leukemia virus, Reo virus, Polio virus, Simian virus 40, Mouse mammary tumor virus, Dengue virus, Rubella virus, protozoans, *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M. salivarium*, and *M. pneumoniae*. Monoclonal antibodies that bind to these pathogenic microorganisms are well known in the art.

BRIEF DESCRIPTION OF THE DRAWINGS

The following drawings form part of the present specification and are included to further demonstrate certain embodiments of the present invention. The embodiments may be better understood by reference to one or more of these drawings in combination with the detailed description of specific embodiments presented herein.

DETAILED DESCRIPTION

Definitions

Figure 1:
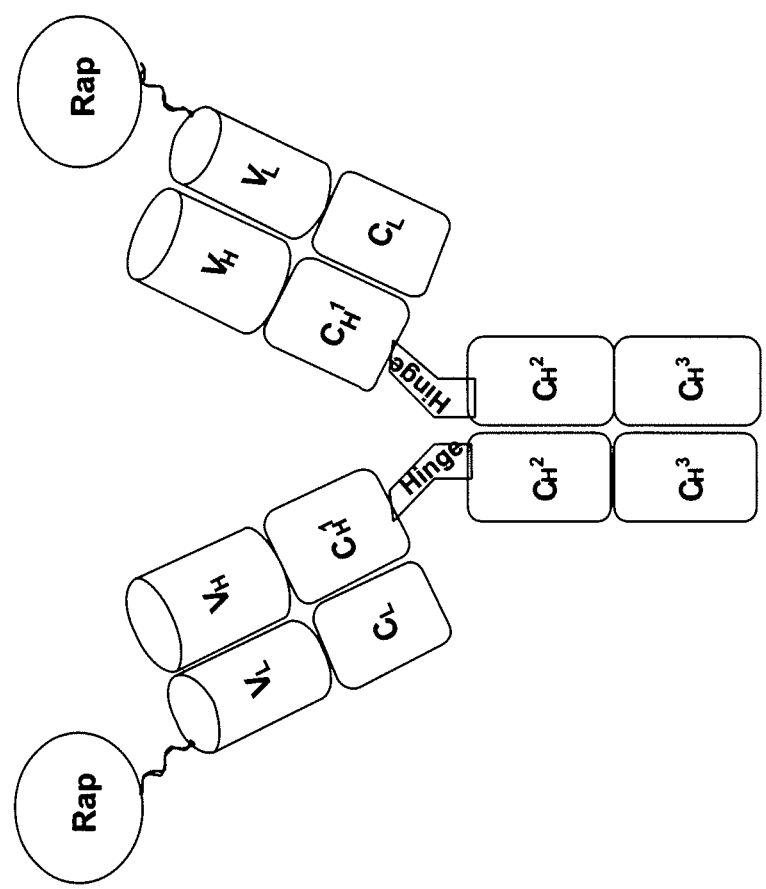
FIG. 1. Molecular design and size of (Q)-hRS7. Schematic structure of 2L-Rap-X, where X is an IgG and Rap can be Rap(Q)

Unless otherwise specified, "a" or "an" means "one or more".

As used herein, the terms "and" and "or" may be used to mean either the conjunctive or disjunctive. That is, both terms should be understood as equivalent to "and/or" unless otherwise stated.

A "therapeutic agent" is an atom, molecule, or compound that is useful in the treatment of a disease. Examples of therapeutic agents include antibodies, antibody fragments, peptides, drugs, toxins, enzymes, nucleases, hormones, immunomodulators, antisense oligonucleotides, small interfering RNA (siRNA), chelators, boron compounds, photoactive agents, dyes, and radioisotopes.

A "diagnostic agent" is an atom, molecule, or compound that is useful in diagnosing a disease. Useful diagnostic agents include, but are not limited to, radioisotopes, dyes (such as with the biotin-streptavidin complex), contrast agents, fluorescent compounds or molecules, and enhancing agents (e.g., paramagnetic ions) for magnetic resonance imaging (MRI).

An "antibody" as used herein refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment. An "antibody" includes monoclonal, polyclonal, bispecific, multispecific, murine, chimeric, humanized and human antibodies.

A "naked antibody" is an antibody or antigen binding fragment thereof that is not attached to a therapeutic or diagnostic agent. The Fc portion of an intact naked antibody can provide effector functions, such as complement fixation and ADCC (see, e.g., Markrides, *Pharmacol Rev* 50:59-87, 1998). Other mechanisms by which naked antibodies induce cell death may include apoptosis. (Vaswani and Hamilton, *Ann Allergy Asthma Immunol* 81: 105-119, 1998.)

An "antibody fragment" is a portion of an intact antibody such as F(ab')$_2$, F(ab)$_2$, Fab', Fab, Fv, sFv, scFv, dAb and the like. Regardless of structure, an antibody fragment binds with the same antigen that is recognized by the full-length antibody. For example, antibody fragments include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). "Single-chain antibodies", often abbreviated as "scFv" consist of a polypeptide chain that comprises both a $V_H$ and a $V_L$ domain which interact to form an antigen-binding site. The $V_H$ and $V_L$ domains are usually linked by a peptide of 1 to 25 amino acid residues. Antibody fragments also include diabodies, triabodies and single domain antibodies (dAb).

An antibody or immunotoxin preparation, or a composition described herein, is said to be administered in a "therapeutically effective amount" if the amount administered is physiologically significant. An agent is physiologically significant if its presence results in a detectable change in the physiology of a recipient subject. In particular embodiments, an antibody preparation is physiologically significant if its presence invokes an antitumor response or mitigates the signs and symptoms of an autoimmune disease state. A physiologically significant effect could also be the evocation of a humoral and/or cellular immune response in the recipient subject leading to growth inhibition or death of target cells.

Antibodies and Antibody Fragments

Techniques for preparing monoclonal antibodies against virtually any target antigen are well known in the art. See, for example, Kohler and Milstein, *Nature* 256: 495 (1975), and Coligan et al. (eds.), CURRENT PROTOCOLS IN IMMUNOLOGY, VOL. 1, pages 2.5.1-2.6.7 (John Wiley & Sons 1991). Briefly, monoclonal antibodies can be obtained by injecting mice with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

After the initial raising of antibodies to the immunogen, the antibodies can be sequenced and subsequently prepared by recombinant techniques. Humanization and chimerization of murine antibodies and antibody fragments are well known to those skilled in the art. The use of antibody components derived from humanized, chimeric or human antibodies obviates potential problems associated with the immunogenicity of murine constant regions.

Chimeric Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. General techniques for cloning murine immunoglobulin variable domains are disclosed, for example, in Orlandi et al., *Proc. Nat'l Acad. Sci. USA* 86: 3833 (1989). Techniques for constructing chimeric antibodies are well known to those of skill in the art. As an example, Leung et al., *Hybridoma* 13:469 (1994), produced an LL2 chimera by combining DNA sequences encoding the $V_K$ and $V_H$ domains of murine LL2, an anti-CD22 monoclonal antibody, with respective human κ and $IgG_1$ constant region domains.

Humanized Antibodies

Techniques for producing humanized MAbs are well known in the art (see, e.g., Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993)). A chimeric or murine monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., *Biotechnology* 9:266 (1991) and Verhoeyen et al., *Science* 239: 1534 (1988). Generally, those human FR amino acid residues that differ from their murine counterparts and are located close to or touching one or more CDR amino acid residues would be candidates for substitution.

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Phamacol.* 3:544-50). A fully human antibody also can be constructed by genetic or chromosomal transfection methods, as well as phage display technology, all of which are known in the art. See for example, McCafferty et al., *Nature* 348:552-553 (1990). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the μ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J. Mol. Biol.* 222:581-97). Library construction was performed according to Andris-Widhopf et al. (2000, In: *Phage Display Laboratory Manual*, Barbas et al. (eds), $1^{st}$ edition, Cold Spring Harbor Laboratory Press, Cold Spring Harbor, N.Y. pp. 9.1 to 9.22). The final Fab fragments were digested with restriction endonucleases and inserted into the bacteriophage genome to make the phage display library. Such libraries may be screened by standard phage display methods, as known in the art (see, e.g., Pasqualini and Ruoslahti, 1996, *Nature* 380:364-366; Pasqualini, 1999, *The Quart. J. Nucl. Med.* 43:159-162).

Phage display can be performed in a variety of formats, for their review, see e.g. Johnson and Chiswell, *Current Opinion in Structural Biology* 3:5564-571 (1993). Human antibodies may also be generated by in vitro activated B cells. See U.S. Pat. Nos. 5,567,610 and 5,229,275, incorporated herein by reference in their entirety. The skilled artisan will realize that these techniques are exemplary and any known method for making and screening human antibodies or antibody fragments may be utilized.

In another alternative, transgenic animals that have been genetically engineered to produce human antibodies may be used to generate antibodies against essentially any immunogenic target, using standard immunization protocols. Methods for obtaining human antibodies from transgenic mice are disclosed by Green et al., *Nature Genet.* 7:13 (1994), Lonberg et al., *Nature* 368:856 (1994), and Taylor et al., *Int. Immun.* 6:579 (1994). A non-limiting example of such a system is the XenoMouse® (e.g., Green et al., 1999, *J. Immunol. Methods* 231:11-23) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along accessory genes and regulatory sequences. The human variable region repertoire may be used to generate antibody producing B cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Antibody Fragments

Antibody fragments which recognize specific epitopes can be generated by known techniques. Antibody fragments are antigen binding portions of an antibody, such as F(ab')$_2$, Fab', F(ab)$_2$, Fab, Fv, sFv and the like. F(ab')$_2$ fragments can be produced by pepsin digestion of the antibody molecule and Fab' fragments can be generated by reducing disulfide bridges of the F(ab')$_2$ fragments. Alternatively, Fab' expression libraries can be constructed (Huse et al., 1989, Science, 246:1274-1281) to allow rapid and easy identification of monoclonal Fab' fragments with the desired specificity. F(ab)$_2$ fragments may be generated by papain digestion of an antibody.

A single chain Fv molecule (scFv) comprises a VL domain and a VH domain. The VL and VH domains associate to form a target binding site. These two domains are further covalently linked by a peptide linker (L). Methods for making scFv molecules and designing suitable peptide linkers are described in U.S. Pat. No. 4,704,692, U.S. Pat. No. 4,946,778, R. Raag and M. Whitlow, "Single Chain Fvs." FASEB Vol 9:73-80 (1995) and R. E. Bird and B. W. Walker, "Single Chain Antibody Variable Regions," TIBTECH, Vol 9: 132-137 (1991).

Techniques for producing single domain antibodies (DABs) are also known in the art, as disclosed for example in Cossins et al. (2006, Prot Express Purif 51:253-259), incorporated herein by reference.

An antibody fragment can be prepared by proteolytic hydrolysis of the full length antibody or by expression in E. coli or another host of the DNA coding for the fragment. An antibody fragment can be obtained by pepsin or papain digestion of full length antibodies by conventional methods. These methods are described, for example, by Goldenberg, U.S. Pat. Nos. 4,036,945 and 4,331,647 and references contained therein. Also, see Nisonoff et al., Arch Biochem. Biophys. 89: 230 (1960); Porter, Biochem. J. 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

Known Antibodies

Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,155; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040, 6,451,310; 6,444,206; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338, the Examples section of each of which is incorporated herein by reference. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Immunoconjugates

In certain embodiments, the antibodies or fragments thereof may be conjugated to one or more therapeutic or diagnostic agents. The therapeutic agents do not need to be the same but can be different, e.g. a drug and a radioisotope. For example, $^{131}$I can be incorporated into a tyrosine of an antibody or fusion protein and a drug attached to an epsilon amino group of a lysine residue. Therapeutic and diagnostic agents also can be attached, for example to reduced SH groups and/or to carbohydrate side chains. Many methods for making covalent or non-covalent conjugates of therapeutic or diagnostic agents with antibodies or fusion proteins are known in the art and any such known method may be utilized.

A therapeutic or diagnostic agent can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., Int. J. Cancer 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic or diagnostic agent can be conjugated via a carbohydrate moiety in the Fc region of the antibody. The carbohydrate group can be used to increase the loading of the same agent that is bound to a thiol group, or the carbohydrate moiety can be used to bind a different therapeutic or diagnostic agent.

Methods for conjugating peptides to antibody components via an antibody carbohydrate moiety are well-known to those of skill in the art. See, for example, Shih et al., *Int. J. Cancer* 41: 832 (1988); Shih et al., *Int. J. Cancer* 46: 1101 (1990); and Shih et al., U.S. Pat. No. 5,057,313, incorporated herein in their entirety by reference. The general method involves reacting an antibody component having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody used as the antibody component of the immunoconjugate is an antibody fragment. However, it is possible to introduce a carbohydrate moiety into the light chain variable region of a full length antibody or antibody fragment. See, for example, Leung et al., *J. Immunol.* 154: 5919 (1995); Hansen et al., U.S. Pat. No. 5,443,953 (1995), Leung et al., U.S. Pat. No. 6,254,868, incorporated herein by reference in their entirety. The engineered carbohydrate moiety is used to attach the therapeutic or diagnostic agent.

In some embodiments, a chelating agent may be attached to an antibody, antibody fragment or fusion protein and used to chelate a therapeutic or diagnostic agent, such as a radionuclide. Exemplary chelators include but are not limited to DTPA (such as Mx-DTPA), DOTA, TETA, NETA or NOTA. Methods of conjugation and use of chelating agents to attach metals or other ligands to proteins are well known in the art (see, e.g., U.S. Pat. No. 7,563,433, the Examples section of which is incorporated herein by reference).

In certain embodiments, radioactive metals or paramagnetic ions may be attached to proteins or peptides by reaction with a reagent having a long tail, to which may be attached a multiplicity of chelating groups for binding ions. Such a tail can be a polymer such as a polylysine, polysaccharide, or other derivatized or derivatizable chains having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose.

Chelates may be directly linked to antibodies or peptides, for example as disclosed in U.S. Pat. No. 4,824,659, incorporated herein in its entirety by reference. Particularly useful metal-chelate combinations include 2-benzyl-DTPA and its monomethyl and cyclohexyl analogs, used with diagnostic isotopes in the general energy range of 60 to 4,000 keV, such as $^{125}$I, $^{131}$I, $^{123}$I, $^{124}$I, $^{62}$Cu, $^{64}$Cu, $^{18}$F, $^{111}$In, $^{67}$Ga, $^{68}$Ga, $^{99m}$Tc, $^{11}$C, $^{13}$N, $^{15}$O, $^{76}$Br, for radioimaging. The same chelates, when complexed with non-radioactive metals, such as manganese, iron and gadolinium are useful for MRI. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT are encompassed.

More recently, methods of $^{18}$F-labeling of use in PET scanning techniques have been disclosed, for example by reaction of F-18 with a metal or other atom, such as aluminum. The $^{18}$F-Al conjugate may be complexed with chelating groups, such as DOTA, NOTA or NETA that are attached directly to antibodies or used to label targetable constructs in pre-targeting methods. Such F-18 labeling techniques are disclosed in U.S. Pat. No. 7,563,433, the Examples section of which is incorporated herein by reference.

Immunotoxins Comprising Ranpirnase (Rap)

Conjugation or fusion of Rap to a tumor-targeting antibody or antibody fragment is a promising approach to enhance its potency, as first demonstrated for LL2-onconase (Newton et al., Blood 2001; 97:528-35), a chemical conjugate comprising Rap and a murine anti-CD22 monoclonal antibody (mAb), and subsequently for 2L-Rap-hLL1-γ4P (see, e.g., Example 2 below), a fusion protein comprising Rap and a humanized anti-CD74 mAb (Stein et al., Blood 2004; 104:3705-11).

The method used to generate 2L-Rap-hLL1-γ4P allowed us to develop a series of structurally similar immunotoxins, referred to in general as 2L-Rap-X, all of which consist of two Rap molecules, each connected via a flexible linker to the N-terminus of one L chain of an antibody of interest (X). We have also generated another series of immunotoxins of the same design, referred to as 2LRap(Q)-X, by substituting Rap with its non-glycosylation form of Rap, designated as Rap(Q) to denote that the potential glycosylation site at Asn69 is changed to Gln (or Q, single letter code). For both series, we made the IgG as either IgG1(γ1) or IgG4(γ4), and to prevent the formation of IgG4 half molecules (Aalberse and Schuurman, Immunology 2002; 105:9-19), we converted the serine residue in the hinge region (S228) of IgG4 to proline (γ4P). The schematic structure of 2L-Rap-X or 2L-Rap(Q)-X is shown in FIG. 1. This design is dictated by the requirement of a pyroglutamate residue at the N-terminus of Rap for the RNase to be fully functional (Liao et al., Nucleic Acids Res 2003; 31:5247-55).

To explore the utility of mRS7 as a potential therapeutic for solid cancers expressing Trop-2, humanized RS7 (hRS7) was made by grafting the complementarity-determining regions of mRS7 onto human IgG1 frameworks (Qu et al., Methods 2005; 36:84-95) and fused to Rap(Q), resulting in 2L-Rap(Q)-hRS7, which is abbreviated (Q)-hRS7 hereafter.

In the work described in the Examples below, we show that the N-terminal fusion of Rap or Rap(Q) to a tumor-targeting mAb is a valid and versatile approach to generate novel immunotoxins by showing that (Q)-hRS7 (i) can be produced in a mammalian host and purified to homogeneity, (ii) retains the binding specificity and affinity of hRS7, as well as the RNase activity of Rap, (iii) suppresses the proliferation of various Trop-2-expressing cancer cell lines at nanomolar concentrations in vitro, and (iv) inhibits the growth of a human lung tumor xenograft in vivo.

The skilled artisan will recognize that the cytotoxic RNase moieties suitable for use in the present invention include polypeptides having a native ranpirnase structure and all enzymatically active variants thereof. These molecules advantageously have an N-terminal pyroglutamic acid resides that appears essential for RNase activity and are not substantially inhibited by mammalian RNase inhibitors. Nucleic acid that encodes a native cytotoxic RNase may be prepared by cloning and restriction of appropriate sequences, or using DNA amplification with polymerase chain reaction (PCR). The amino acid sequence of Rana Pipiens ranpirnase can be obtained from Ardelt et al., J. Biol. Chem., 256: 245 (1991), and cDNA sequences encoding native ranpirnase, or a conservatively modified variation thereof, can be gene-synthesized by methods similar to the en bloc V-gene assembly method used in hLL2 humanization. (Leung et al., Mol. Immunol., 32: 1413, 1995). Methods of making cytotoxic RNase variants are known in the art and are within the skill of the routineer.

Alternatively, nucleic acid that encodes a cytotoxic RNase or variant thereof may be synthesized in vitro. Chemical synthesis produces a single-stranded oligonucleotide. This may be converted to a double-stranded DNA by hybridization with a complementary sequence, or by polymerization with a DNA polymerase using a short primer and the single strand as a template. While chemical synthesis is most suited to sequences of about 100 bases, longer sequences may be obtained by ligating shorter sequences. Example 2, infra, provides one illustrative method for obtaining a cytotoxic RNase gene.

Dock and Lock (DNL) Method

The "dock-and-lock" (DNL) method exploits specific protein/protein interactions that occur between the regulatory (R) subunits of cAMP-dependent protein kinase (PKA) and the anchoring domain (AD) of A-kinase anchoring proteins (AKAPs) (Baillie et al., FEBS Letters. 2005; 579: 3264. Wong and Scott, Nat. Rev. Mol. Cell. Biol. 2004; 5: 959). PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (R1 and RID, and each type has α and β isoforms (Scott, Pharmacol. Ther. 1991; 50:123). The R subunits have been isolated only as stable dimers and the dimerization domain has been shown to consist of the first 44 amino-terminal residues (Newlon et al., Nat. Struct. Biol. 1999; 6:222). Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561)

Since the first AKAP, microtubule-associated protein-2, was characterized in 1984 (Lohmann et al., Proc. Natl. Acad. Sci. USA. 1984; 81:6723), more than 50 AKAPs that localize to various subcellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell. Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RII dimers ranging from 2 to 90 nM (Alto et al., Proc. Natl. Acad. Sci. USA. 2003; 100:4445). Interestingly, AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

DDD of Human RIIα and AD of AKAPs as Linker Modules

We have developed a platform technology to utilize the DDD of human PKA RIIα and the AD of AKAP proteins as an excellent pair of linker modules for docking any combination of entities, referred to hereafter as A and B, into a noncovalent complex, which could be further locked into a stably tethered structure through the introduction of cysteine residues into both the DDD and AD at strategic positions to facilitate the formation of disulfide bonds. The general methodology of the "dock-and-lock" approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., Proc. Natl. Acad. Sci. USA. 2001; 98:8480) to ligate site-specifically. In certain embodiments the $a_2$ subunit may contain two identical effector moieties, such as an antibody, antibody fragment or cytotoxin, each attached to an identical DDD sequence. The trimeric $a_2b$ complex may comprise two copies of a first effector moieties and one copy of a second effector moiety.

By attaching the DDD and AD away from the functional groups of the precursors, such site-specific ligations are expected to preserve the original activities of the precursors. This approach is modular in nature and potentially can be applied to link, site-specifically and covalently, a wide range of substances. The DNL method was disclosed in U.S. Pat. Nos. 7,550,143; 7,521,056; 7,534,866; 7,527,787 and 7,666, 400, the Examples section of each incorporated herein by reference. Although in a preferred embodiment the DNL complex may comprise a trimeric structure, in alternative embodiments other stoichiometries are possible, such as four copies of a toxin moiety and one copy of an antibody or antibody fragment.

In preferred embodiments, the effector moiety is a protein or peptide, more preferably an antibody, antibody fragment or toxin, which can be linked to a DDD or AD moiety to form a fusion protein or peptide. A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. In a most preferred embodiment, attachment of AD or DDD moieties to an antibody or antibody fragment occurs at the C-terminal end of the heavy chain subunit, at the opposite end of the molecule from the antigen-binding site. However, as discussed below, N-terminal attachment to antibodies or antibody fragments may also be utilized while retaining antigen-binding activity. Site-specific attachment of a variety of effector moieties may be performed using techniques known in the art, such as the use of bivalent cross-linking reagents and/or other chemical conjugation techniques.

DDD and AD Sequence Variants

In certain embodiments, the AD and DDD sequences incorporated into the immunotoxin DNL construct comprise the amino acid sequences of DDD1 and AD1 below. In more preferred embodiments, the AD and DDD sequences comprise the amino acid sequences of DDD2 and AD2, which are designed to promote disulfide bond formation between the DDD and AD moieties.

```
DDD1
                                        (SEQ ID NO: 13)
SHIQIPPGLTELLQGYTVEVLRQQPPDLVEFAVEYFTRLREARA

DDD2
                                        (SEQ ID NO: 14)
CGHIQIPPGLTELLQGYTVEVLRQQPPDLVEFAVEYFTRLREARA

AD1
                                        (SEQ ID NO: 15)
QIEYLAKQIVDNAIQQA

AD2
                                        (SEQ ID NO: 16)
CGQIEYLAKQIVDNAIQQAGC
```

The skilled artisan will realize that DDD1 and DDD2 comprise the DDD sequence of the human RIIα form of protein kinase A. However, in alternative embodiments, the DDD and AD moieties may be based on the DDD sequence of the human RIα form of protein kinase A and a corresponding AKAP sequence, as exemplified in DDD3, DDD3C and AD3 below.

```
DDD3
                                        (SEQ ID NO: 17)
SLRECELYVQKHNIQALLKDSIVQLCTARPERPMAFLREYFERLEKEEA
K

DDD3C
                                        (SEQ ID NO: 18)
MSCGGSLRECELYVQKHNIQALLKDSIVQLCTARPERPMAFLREYFERL
EKEEAK

AD3
                                        (SEQ ID NO: 19)
CGFEELAWKIAKMIWSDVFQQGC
```

Still other alternative DDD moieties based on the known human RIβ and Rβ amino acid sequences may be designed and utilized (see, e.g., NCBI Accession Nos. NP_001158233 and NP_002727, sequences below).

```
Human PKA RIβ Amino Acid Sequence
                                        (SEQ ID NO: 20)
MASPPACPSE EDESLKGCEL YVQLHGIQQV LKDCIVHLCI

SKPERPMKFL REHFEKLEKE ENRQILARQK SNSQSDSHDE

EVSPTPPNPV VKARRRGGV SAEVYTEEDA VSYVRKVIPK

DYKTMTALAK AISKNVLFAH LDDNERSDIF DAMFPVTHIA

GETVIQQGNE GDNFYVVDQG EVDVYVNGEW VTNISEGGSF

GELALIYGTP RAATVKAKTD LKLWGIDRDS YRRILMGSTL

RKRKMYEEFL SKVSILESLE KWERLTVADA LEPVQFEDGE

KIVVQGEPGD DFYIITEGTA SVLQRRSPNE EYVEVGRLGP

SDYFGEIALL LNRPRAATVV ARGPLKCVKL DRPRFERVLG

PCSEILKRNI QRYNSFISLT V

Human PKA RIβ Amino Acid Sequence
                                        (SEQ ID NO: 21)
MSIEIPAGLT ELLQGFTVEV LRHQPADLLE FALQHFTRLQ

QENERKGTAR FGHEGRTWGD LGAAAGGGTP SKGVNFAEEP
```

```
MQSDSEDGEE EEAAPADAGA FNAPVINRFT RRASVCAEAY

NPDEEEDDAE SRIIHPKTDD QRNRLQEACK DILLFKNLDP

EQMSQVLDAM FEKLVKDGEH VIDQGDDGDN FYVIDRGTFD

IYVKCDGVGR CVGNYDNRGS FGELALMYNT PRAATITATS

PGALWGLDRV TFRRIIVKNN AKKRKMYESF IESLPFLKSL

EFSERLKVVD VIGTKVYNDG EQIIAQGDSA DSFFIVESGE

VKITMKRKGK SEVEENGAVE IARCSRGQYF GELALVTNKP

RAASAHAIGT VKCLAMDVQA FERLLGPCME IMKRNIATYE

EQLVALFGTN MDIVEPTA
```

In other alternative embodiments, different sequence variants of AD and/or DDD moieties may be utilized in construction of the immunotoxin DNL constructs. The structure-function relationships of the AD and DDD domains have been the subject of investigation. (See, e.g., Burns-Hamuro et al., 2005, Protein Sci 14:2982-92; Carr et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400:493-99; Gold et al., 2006, Mol Cell 24:383-95; Kinderman et al., 2006, Mol Cell 24:397-408, the entire text of each of which is incorporated herein by reference.)

For example, Kinderman et al. (2006) examined the crystal structure of the AD-DDD binding interaction and concluded that the human DDD sequence contained a number of conserved amino acid residues that were important in either dimer formation or AKAP binding, underlined in the sequence below. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding. Thus, a potential alternative DDD sequence of use for construction of DNL constructs is shown in SEQ ID NO:22, wherein "X" represents a conservative amino acid substitution. Conservative amino acid substitutions are discussed in more detail below, but could involve for example substitution of an aspartate residue for a glutamate residue, or a leucine or valine residue for an isoleucine residue, etc. Such conservative amino acid substitutions are well known in the art.

```
Human DDD sequence from protein kinase A
                                        (SEQ ID NO: 13)
SHIQIPPGLTELLQGYTVEVLRQQPPDLVEFAVEYFTRLREARA (SEQ ID NO: 22)
XXIXIXXXLXXLLXXYXVXVLXXXXXXLVXFXVXYFXXLXXXXX
```

Alto et al. (2003) performed a bioinformatic analysis of the AD sequence of various AKAP proteins to design an RII selective AD sequence called AKAP-IS shown below, with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in the sequence below. Therefore, the skilled artisan will realize that variants which may function for DNL constructs are indicated by SEQ ID NO:23, where "X" is a conservative amino acid substitution.

```
AKAP-IS sequence
                        (SEQ ID NO: 15)
QIEYLAKQIVDNAIQQA (SEQ ID NO: 23)
XXXXXAXXIVXXAIXXX
```

Similarly, Gold (2006) utilized crystallography and peptide screening to develop a SuperAKAP-IS sequence shown below, exhibiting a five order of magnitude higher selectivity for the RII isoform of PKA compared with the RI isoform. Underlined residues indicate the positions of amino acid substitutions, relative to the AKAP-IS sequence that increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare cytotoxic DNL constructs. Other alternative sequences that might be substituted for the AKAP-IS AD sequence are shown below. Substitutions relative to the AKAP-IS sequence are underlined. It is anticipated that, as with the AKAP-IS sequence, the AD moiety may also include the additional N-terminal residues cysteine and glycine and C-terminal residues glycine and cysteine.

```
SuperAKAP-IS
                        (SEQ ID NO: 24)
QIEYVAKQIVDYAIHQA

Alternative AKAP sequences
                        (SEQ ID NO: 25)
QIEYKAKQIVDHAIHQA (SEQ ID NO: 26)
QIEYHAKQIVDHAIHQA (SEQ ID NO: 27)
QIEYVAKQIVDHAIHQA
```

Figure 2:
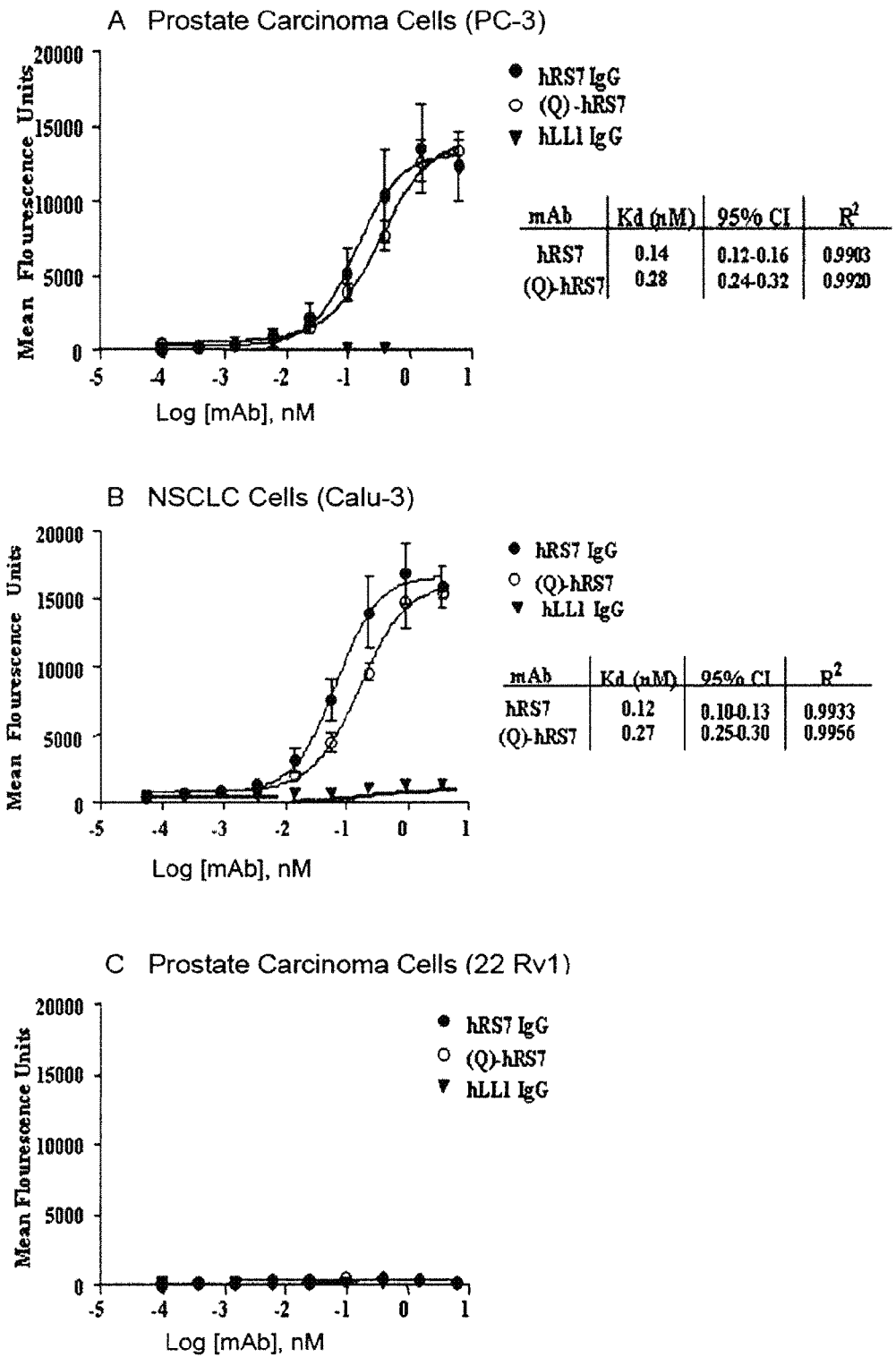
FIG. 2. Cell binding curves obtained for PC-3 (A), Calu-3 (B) and 22Rv1 (C) from ELISA using the luminol substrates. The mean fluorescence units were plotted against concentrations and the resulting data were analyzed by Prism software to obtain the values of $K_D$.

FIG. 2 of Gold et al. disclosed additional DDD-binding sequences from a variety of AKAP proteins, shown below.

```
RII-Specific AKAPs
AKAP-KL
                        (SEQ ID NO: 28)
PLEYQAGLLVQNAIQQAI

AKAP79
                        (SEQ ID NO: 29)
LLIETASSLVKNAIQLSI

AKAP-Lbc
                        (SEQ ID NO: 30)
LIEEAASRIVDAVIEQVK

RI-Specific AKAPs
AKAPce
                        (SEQ ID NO: 31)
ALYQFADRFSELVISEAL

RIAD
                        (SEQ ID NO: 32)
LEQVANQLADQIIKEAT

PV38
                        (SEQ ID NO: 33)
FEELAWKIAKMIWSDVF
```

```
Dual-Specificity AKAPs
AKAP7
                        (SEQ ID NO: 34)
ELVRLSKRLVENAVLKAV

MAP2D
                        (SEQ ID NO: 35)
TAEEVSARIVQVVTAEAV

DAKAP1
                        (SEQ ID NO: 36)
QIKQAAFQLISQVILEAT

DAKAP2
                        (SEQ ID NO: 37)
LAWKIAKMIVSDVMQQ
```

Stokka et al. (2006) also developed peptide competitors of AKAP binding to PKA, shown below. The peptide antagonists were designated as Ht31, RIAD and PV-38. The Ht-31 peptide exhibited a greater affinity for the RII isoform of PKA, while the RIAD and PV-38 showed higher affinity for R1.

```
Ht31
                        (SEQ ID NO: 38)
DLIEEAASRIVDAVIEQVKAAGAY

RIAD
                        (SEQ ID NO: 39)
LEQYANQLADQIIKEATE

PV-38
                        (SEQ ID NO: 40)
FEELAWKIAKMIWSDVFQQC
```

Hundsrucker et al. (2006) developed still other peptide competitors for AKAP binding to PKA, with a binding constant as low as 0.4 nM to the DDD of the RII form of PKA. The sequences of various AKAP antagonistic peptides are provided in Table 1 of Hundsrucker et al., reproduced below.

TABLE 1

AKAP Peptide sequences
AKAPIS represents a synthetic RII subunit-binding peptide.
All other peptides are derived from the RII-binding domains of the indicated AKAPs.

| Peptide | Sequence |
|---|---|
| AKAPIS | QIEYLAKQIVDNAIQQA (SEQ ID NO: 15) |
| AKAPIS-P | QIEYLAKQIPDNAIQQA (SEQ ID NO: 41) |
| Ht31 | KGADLIEEAASRIVDAVIEQVKAAG (SEQ ID NO: 42) |
| Ht31-P | KGADLIEEAASRIPDAPIEQVKAAG (SEQ ID NO: 43) |
| AKAP7δ-wt-pep | PEDAELVRLSKRLVENAVLKAVQQY (SEQ ID NO: 44) |
| AKAP7δ-L304T-pep | PEDAELVRTSKRLVENAVLKAVQQY (SEQ ID NO: 45) |
| AKAP7δ-L308D-pep | PEDAELVRLSKRDVENAVLKAVQQY (SEQ ID NO: 46) |
| AKAP7δ-P-pep | PEDAELVRLSKRLPENAVLKAVQQY (SEQ ID NO: 47) |

TABLE 1-continued

AKAP Peptide sequences
AKAPIS represents a synthetic RII
subunit-binding peptide.
All other peptides are derived from the
RII-binding domains of the indicated AKAPs.

| | Peptide Sequence |
|---|---|
| AKAP7δ-PP-pep | PEDAELVRLSKRLPENAPLKAVQQY (SEQ ID NO: 48) |
| AKAP7δ-L314E-pep | PEDAELVRLSKRLVENAVEKAVQQY (SEQ ID NO: 49) |
| AKAP1-pep | EEGLDRNEEIKRAAFQIISQVISEA (SEQ ID NO: 50) |
| AKAP2-pep | LVDDPLEYQAGLLVQNAIQQAIAEQ (SEQ ID NO: 51) |
| AKAP5-pep | QYETLLIETASSLVKNAIQLSIEQL (SEQ ID NO: 52) |
| AKAP9-pep | LEKQYQEQLEEEVAKVIVSMSIAFA (SEQ ID NO: 53) |
| AKAP10-pep | NTDEAQEELAWKIAKMIVSDIMQQA (SEQ ID NO: 54) |
| AKAP11-pep | VNLDKKAVLAEKIVAEAIEKAEREL (SEQ ID NO: 55) |
| AKAP12-pep | NGILELETKSSKLVQNIIQTAVDQF (SEQ ID NO: 56) |
| AKAP14-pep | TQDKNYEDELTQVALALVEDVINYA (SEQ ID NO: 57) |
| Rab32-pep | ETSAKDNINIEEAARFLVEKILVNH (SEQ ID NO: 58) |

Figure 4:
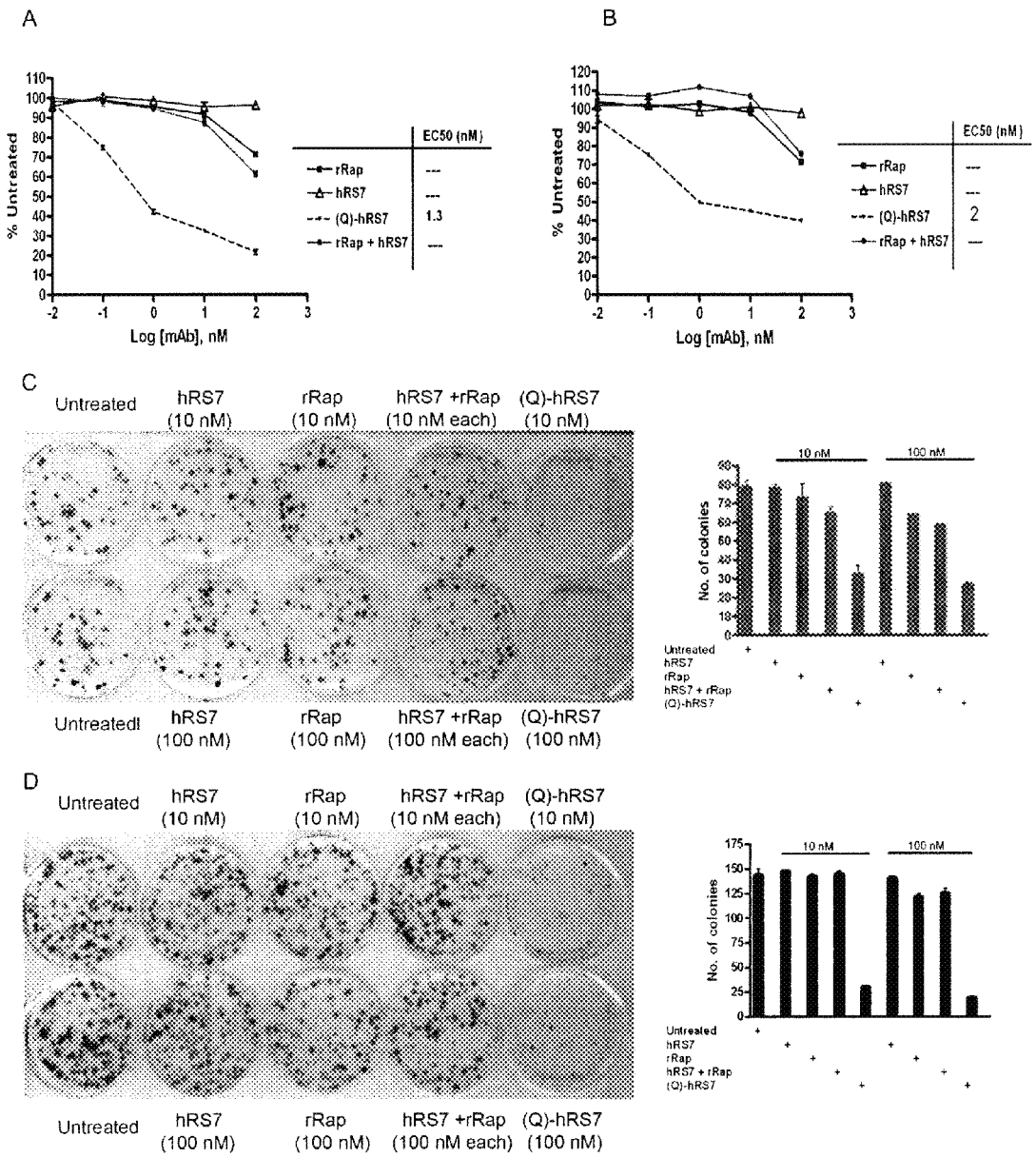
FIG. 4. In vitro cytotoxicity of (Q)-hRS7 as evidenced by the MTS assay shown for ME-180 (A) and T-47D (B), and the colony formation assay shown for (C) DU-145 and (D) PC-3. The data in (A) and (B) were analyzed by Prism software to obtain the values of EC50.

Residues that were highly conserved among the AD domains of different AKAP proteins are indicated below by underlining with reference to the AKAP IS sequence below. The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence were those of AKAP-IS, AKAP7δ-wt-pep, AKAP7δ-L304T-pep and AKAP7δ-L308D-pep.

```
                AKAP-IS
                                       (SEQ ID NO: 15)
         QIEYLAKQIVDNAIQQA
```

Carr et al. (2001) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence. Residues that were particularly conserved are further indicated by italics. The residues overlap with, but are not identical to those suggested by Kinderman et al. (2006) to be important for binding to AKAP proteins. Thus, a potential DDD sequence is indicated in SEQ ID NO:59, wherein "X" represents a conservative amino acid substitution.

```
                                            (SEQ ID NO: 13)
         SHIQIPPGLTELLQGYTVEVLRQQPPDLVEFAVEYFTRLREARA
```

```
                                            (SEQ ID NO: 59)
         XHIXIPXGLXELLQGYTXEVLRXQPXDLVEFAXXYFXXLXEXRX
```

The skilled artisan will realize that in general, those amino acid residues that are highly conserved in the DDD and AD sequences from different proteins are ones that it may be preferred to remain constant in making amino acid substitutions, while residues that are less highly conserved may be more easily varied to produce sequence variants of the AD and/or DDD sequences described herein.

In addition to sequence variants of the DDD and/or AD moieties, in certain embodiments it may be preferred to introduce sequence variations in the antibody moiety or the linker peptide sequence joining the antibody with the AD sequence. In one illustrative example, three possible variants of fusion protein sequences, are shown below.

```
         (L)
                                            (SEQ ID NO: 60)
         QKSLSLSPGLGSGGGGSGGCG (A)
                                            (SEQ ID NO: 61)
         QKSLSLSPGAGSGGGGSGGCG (-)
                                            (SEQ ID NO: 62)
         QKSLSLSPGGSGGGGSGGCG
```

Amino Acid Substitutions

In certain embodiments, the disclosed methods and compositions may involve production and use of proteins or peptides with one or more substituted amino acid residues. The structural, physical and/or therapeutic characteristics of native, chimeric, humanized or human antibodies, or AD or DDD sequences may be optimized by replacing one or more amino acid residues. For example, it is well known in the art that the functional characteristics of humanized antibodies may be improved by substituting a limited number of human framework region (FR) amino acids with the corresponding FR amino acids of the parent murine antibody. This is particularly true when the framework region amino acid residues are in close proximity to the CDR residues.

In other cases, the therapeutic properties of an antibody, such as binding affinity for the target antigen, the dissociation- or off-rate of the antibody from its target antigen, or even the effectiveness of induction of CDC (complement-dependent cytotoxicity) or ADCC (antibody dependent cellular cytotoxicity) by the antibody, may be optimized by a limited number of amino acid substitutions.

In alternative embodiments, the DDD and/or AD sequences used to make the subject DNL constructs may be further optimized, for example to increase the DDD-AD binding affinity. Potential sequence variations in DDD or AD sequences are discussed above.

The skilled artisan will be aware that, in general, amino acid substitutions typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within ±2 is preferred, within ±1 are more preferred, and within ±0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (O) glu, asn; Glu (E) gln, asp; Gly (G) ala; H is (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL website at rockefeller.edu) For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded protein sequence are well known and a matter of routine experimentation for the skilled artisan, for example by the technique of site-directed mutagenesis or by synthesis and assembly of oligonucleotides encoding an amino acid substitution and splicing into an expression vector construct.

Therapeutic Agents

In alternative embodiments, therapeutic agents such as cytotoxic agents, anti-angiogenic agents, pro-apoptotic agents, antibiotics, hormones, hormone antagonists, chemokines, drugs, prodrugs, toxins, enzymes or other agents may be used, either conjugated to the subject immunotoxins or separately administered before, simultaneously with, or after the immunotoxin. Drugs of use may possess a pharmaceutical property selected from the group consisting of antimitotic, antikinase, alkylating, antimetabolite, antibiotic, alkaloid, anti-angiogenic, pro-apoptotic agents and combinations thereof.

Exemplary drugs of use may include 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, estramustine, epipodophyllotoxin, estrogen receptor binding agents, etoposide (VP 16), etoposide glucuronide, etoposide phosphate, floxuridine (FUdR), 3',5'-O-dioleoyl-FudR (FUdR-dO), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosourea, plicomycin, procarbazine, paclitaxel, pentostatin, PSI-341, raloxifene, semustine, streptozocin, tamoxifen, taxol, temazolomide (an aqueous form of DTIC), transplatinum, thalidomide, thioguanine, thiotepa, teniposide, topotecan, uracil mustard, vinorelbine, vinblastine, vincristine and vinca alkaloids.

Toxins of use may include ricin, abrin, alpha toxin, saporin, ribonuclease (RNase), e.g., onconase, DNase I, *Staphylococcal* enterotoxin-A, pokeweed antiviral protein, gelonin, diphtheria toxin, *Pseudomonas* exotoxin, and *Pseudomonas* endotoxin.

Chemokines of use may include RANTES, MCAF, MIP1-alpha, MIP1-Beta and IP-10.

In certain embodiments, anti-angiogenic agents, such as angiostatin, baculostatin, canstatin, maspin, anti-VEGF antibodies, anti-P1GF peptides and antibodies, anti-vascular growth factor antibodies, anti-Flk-1 antibodies, anti-Flt-1 antibodies and peptides, anti-Kras antibodies, anti-cMET antibodies, anti-MIF (macrophage migration-inhibitory factor) antibodies, laminin peptides, fibronectin peptides, plasminogen activator inhibitors, tissue metalloproteinase inhibitors, interferons, interleukin-12, IP-10, Gro-β, thrombospondin, 2-methoxyoestradiol, proliferin-related protein, carboxiamidotriazole, CM101, Marimastat, pentosan polysulphate, angiopoietin-2, interferon-alpha, herbimycin A, PNU145156E, 16K prolactin fragment, Linomide (roquinimex), thalidomide, pentoxifylline, genistein, TNP-470, endostatin, paclitaxel, accutin, angiostatin, cidofovir, vincristine, bleomycin, AGM-1470, platelet factor 4 or minocycline may be of use.

Immunomodulators of use may be selected from a cytokine, a stem cell growth factor, a lymphotoxin, a hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-α, -β or -γ, and stem cell growth factor, such as that designated "S1 factor". Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-25, LIF, kit-ligand or FLT-3, angiostatin, thrombospondin, endostatin, tumor necrosis factor and LT.

Radionuclides of use include, but are not limited to-$^{111}$In, $^{177}$Lu, $^{212}$Bi, $^{213}$Bi, $^{211}$At $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. The therapeutic radionuclide preferably has a decay-energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, 1-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like. Some useful diagnostic nuclides may include $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94}$Tc, $^{94m}$Tc, $^{99m}$Tc, or $^{111}$In.

Therapeutic agents may include a photoactive agent or dye. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy. See Joni et al. (eds.), PHOTODYNAMIC THERAPY OF TUMORS AND OTHER DISEASES (Libreria Progetto 1985); van den Bergh, Chem. Britain (1986), 22:430. Moreover, monoclonal antibodies have been coupled with photoactivated dyes for achieving phototherapy. See Mew et al., J. Immunol. (1983), 130:1473; idem., Cancer Res. (1985), 45:4380; Oseroff et al., Proc. Natl. Acad. Sci. USA (1986), 83:8744; idem., Photochem. Photobiol. (1987), 46:83; Hasan et al., Prog. Clin. Biol. Res. (1989), 288:471; Tatsuta et al., Lasers Surg. Med. (1989), 9:422; Pelegrin et al., Cancer (1991), 67:2529.

Other useful therapeutic agents may comprise oligonucleotides, especially antisense oligonucleotides that preferably are directed against oncogenes and oncogene products, such as bcl-2 or p53. A preferred form of therapeutic oligonucleotide is siRNA.

Diagnostic Agents

Diagnostic agents are preferably selected from the group consisting of a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters. Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III). Ultrasound contrast agents may comprise liposomes, such as gas filled liposomes. Radiopaque diagnostic agents may be selected from compounds, barium compounds, gallium compounds, and thallium compounds. A wide variety of fluorescent labels are known in the art, including but not limited to fluorescein isothiocyanate, rhodamine, phycoerytherin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

Methods of Therapeutic Treatment

Various embodiments concern methods of treating a cancer in a subject, such as a mammal, including humans, domestic or companion pets, such as dogs and cats, comprising administering to the subject a therapeutically effective amount of a cytotoxic immunoconjugate.

In one embodiment, immunological diseases which may be treated with the subject immunotoxins may include, for example, joint diseases such as ankylosing spondylitis, juvenile rheumatoid arthritis, rheumatoid arthritis; neurological disease such as multiple sclerosis and myasthenia gravis; pancreatic disease such as diabetes, especially juvenile onset diabetes; gastrointestinal tract disease such as chronic active hepatitis, celiac disease, ulcerative colitis, Crohn's disease, pernicious anemia; skin diseases such as psoriasis or scleroderma; allergic diseases such as asthma and in transplantation related conditions such as graft versus host disease and allograft rejection.

The administration of the cytotoxic immunoconjugates can be supplemented by administering concurrently or sequentially a therapeutically effective amount of another antibody that binds to or is reactive with another antigen on the surface of the target cell. Preferred additional MAbs comprise at least one humanized, chimeric or human MAb selected from the group consisting of a MAb reactive with CD4, CD5, CD8, CD14, CD15, CD16, CD19, IGF-1R, CD20, CD21, CD22, CD23, CD25, CD30, CD32b, CD33, CD37, CD38, CD40, CD40L, CD45, CD46, CD52, CD54, CD70, CD74, CD79a, CD80, CD95, CD126, CD133, CD138, CD154, CEACAM5, CEACAM6, B7, AFP, PSMA, EGP-1, EGP-2, carbonic anhydrase IX, PAM4 antigen, MUC1, MUC2, MUC3, MUC4, MUC5, Ia, MIF, HM1.24, HLA-DR, tenascin, Flt-3, VEGFR, P1GF, ILGF, IL-6, IL-25, tenascin, TRAIL-R1, TRAIL-R2, complement factor C5, oncogene product, or a combination thereof. Various antibodies of use, such as anti-CD19, anti-CD20, and anti-CD22 antibodies, are known to those of skill in the art. See, for example, Ghetie et al., *Cancer Res.* 48:2610 (1988); Hekman et al., *Cancer Immunol. Immunother.* 32:364 (1991); Longo, *Curr. Opin. Oncol.* 8:353 (1996), U.S. Pat. Nos. 5,798,554; 6,187,287; 6,306,393; 6,676,924; 7,109,304; 7,151,164; 7,230,084; 7,230,085; 7,238,785; 7,238,786; 7,282,567; 7,300,655; 7,312,318; 7,501,498; 7,612,180; 7,670,804; and U.S. Patent Application Publ. Nos. 20080131363; 20070172920; 20060193865; and 20080138333, the Examples section of each incorporated herein by reference.

The immunotoxin therapy can be further supplemented with the administration, either concurrently or sequentially, of at least one therapeutic agent. For example, "CVB" (1.5 g/m² cyclophosphamide, 200-400 mg/m² etoposide, and 150-200 mg/m² carmustine) is a regimen used to treat non-Hodgkin's lymphoma. Patti et al., *Eur. I Haematol.* 51: 18 (1993). Other suitable combination chemotherapeutic regimens are well-known to those of skill in the art. See, for example, Freedman et al., "Non-Hodgkin's Lymphomas," in CANCER MEDICINE, VOLUME 2, 3rd Edition, Holland et al. (eds.), pages 2028-2068 (Lea & Febiger 1993). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate, bendamustine, and bryostatin-1.

The subject immunotoxins can be formulated according to known methods to prepare pharmaceutically useful compositions, whereby the immunotoxin is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The subject immunotoxins can be formulated for intravenous administration via, for example, bolus injection or continuous infusion. Preferably, the immunotoxin is infused over a period of less than about 4 hours, and more preferably, over a period of less than about 3 hours. For example, the first 25-50 mg could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the immunotoxins. Control release preparations can be prepared through the use of polymers to complex or adsorb the immunotoxins. For example, biocompatible polymers include matrices of poly (ethylene-co-vinyl acetate) and matrices of a polyanhydride copolymer of a stearic acid dimer and sebacic acid. Sherwood et al., *Bio/Technology* 10: 1446 (1992). The rate of release from such a matrix depends upon the molecular weight of the immunotoxin, the amount of immunotoxin within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunotoxin may also be administered to a mammal subcutaneously or even by other parenteral routes. Moreover, the administration may be by continuous infusion or by single or multiple boluses. Preferably, the immunotoxin is infused over a period of less than about 4 hours, and more preferably, over a period of less than about 3 hours.

More generally, the dosage of an administered immunotoxin for humans will vary depending upon such factors as the patient's age, weight, height, sex, general medical condition and previous medical history. It may be desirable to provide the recipient with a dosage of immunotoxin that is in the range of from about 1 mg/kg to 25 mg/kg as a single intravenous infusion, although a lower or higher dosage also may be administered as circumstances dictate. A dosage of 1-20 mg/kg for a 70 kg patient, for example, is 70-1,400 mg, or 41-824 mg/m² for a 1.7-m patient. The dosage may be repeated as needed, for example, once per week for 4-10 weeks, once per week for 8 weeks, or once per week for 4 weeks. It may also be given less frequently, such as every other week for several months, or monthly or quarterly for many months, as needed in a maintenance therapy.

Alternatively, an immunotoxin may be administered as one dosage every 2 or 3 weeks, repeated for a total of at least 3 dosages. Or, the construct may be administered twice per week for 4-6 weeks. If the dosage is lowered to approximately 200-300 mg/m² (340 mg per dosage for a 1.7-m patient, or 4.9 mg/kg for a 70 kg patient), it may be administered once or even twice weekly for 4 to 10 weeks. Alternatively, the dosage schedule may be decreased, namely every 2 or 3 weeks for 2-3 months. It has been determined, however, that even higher doses, such as 20 mg/kg once weekly or once every 2-3 weeks can be administered by slow i.v. infusion, for repeated dosing cycles. The dosing schedule can optionally be repeated at other intervals and dosage may be given through various parenteral routes, with appropriate adjustment of the dose and schedule.

In preferred embodiments, the immunotoxins are of use for therapy of cancer. Examples of cancers include, but are not limited to, carcinoma, lymphoma, glioblastoma, melanoma, sarcoma, and leukemia, myeloma, or lymphoid malignancies. More particular examples of such cancers are noted below and include: squamous cell cancer (e.g., epithelial squamous cell cancer), Ewing sarcoma, Wilms tumor, astrocytomas, lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma multiforme, cervical cancer, ovarian cancer, liver cancer, bladder cancer, hepatoma, hepatocellular carcinoma, neuroendocrine tumors, medullary thyroid cancer, differentiated thyroid carcinoma, breast cancer, ovarian cancer, colon cancer, rectal cancer, endometrial cancer or uterine carcinoma, salivary gland carcinoma, kidney or renal cancer, prostate cancer, vulvar cancer, anal carcinoma, penile carcinoma, as well as head-and-neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor). Cancers conducive to treatment methods of the present invention involves cells which express, over-express, or abnormally express IGF-1R.

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Polycythemia vera, Parathyroid Cancer, Penile Cancer, Pheochromocytoma, Pituitary Tumor, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be treated include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis.

In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

Expression Vectors

Still other embodiments may concern DNA sequences comprising a nucleic acid encoding an antibody, antibody fragment, toxin or constituent fusion protein of an immunotoxin, such as a DNL construct. Fusion proteins may comprise an antibody or fragment or toxin attached to, for example, an AD or DDD moiety.

Various embodiments relate to expression vectors comprising the coding DNA sequences. The vectors may contain sequences encoding the light and heavy chain constant regions and the hinge region of a human immunoglobulin to which may be attached chimeric, humanized or human variable region sequences. The vectors may additionally contain promoters that express the encoded protein(s) in a selected host cell, enhancers and signal or leader sequences. Vectors that are particularly useful are pdHL2 or GS. More preferably, the light and heavy chain constant regions and hinge region may be from a human EU myeloma immunoglobulin, where optionally at least one of the amino acid in the allotype positions is changed to that found in a different IgG1 allotype, and wherein optionally amino acid 253 of the heavy chain of EU based on the EU number system may be replaced with alanine. See Edelman et al., *Proc. Natl. Acad. Sci. USA* 63: 78-85 (1969). In other embodiments, an IgG1 sequence may be converted to an IgG4 sequence.

The skilled artisan will realize that methods of genetically engineering expression constructs and insertion into host cells to express engineered proteins are well known in the art and a matter of routine experimentation. Host cells and methods of expression of cloned antibodies or fragments have been described, for example, in U.S. Pat. Nos. 7,531,327 and 7,537,930, the Examples section of each incorporated herein by reference.

Kits

Various embodiments may concern kits containing components suitable for treating or diagnosing diseased tissue in a patient. Exemplary kits may contain one or more immunotoxins as described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used. In certain embodiments, a therapeutic agent may be provided in the form of a prefilled syringe or autoinjection pen containing a sterile, liquid formulation or lyophilized preparation.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

EXAMPLES

The following examples are provided to illustrate, but not to limit, the claims of the present invention.

Example 1

Ranpirnase (Frog RNase) Targeted with a Humanized, Internalizing, Anti-Trop-2 Antibody Has Potent Cytotoxicity Against Diverse Human Epithelial Cancer Cells A novel immunotoxin comprising an amphibian ribonuclease recombinantly tethered to a humanized anti-Trop-2 antibody is shown herein to exhibit broad and potent antiproliferative activity against diverse human epithelial cancer cell lines in vitro, such as cervical, breast, colon, pancreatic, ovarian, and prostate cancer, as well as a human lung cancer xenograft in vivo.

Abstract

We describe herein the generation of a novel IgG-based immunotoxin, designated 2L-Rap(Q)-hRS7, comprising Rap(Q), a mutant form of Rap with the putative N-glycosylation site removed, and hRS7, an internalizing, humanized antibody against Trop-2, a cell-surface glycoprotein overexpressed in a variety of epithelial cancers. Various tests, including size-exclusion HPLC, SDS-PAGE, flow cytometry, RNase activity, internalization, cell viability and colony formation, demonstrated this immunotoxin's purity, molecular integrity, comparable affinity to hRS7 for binding to several different Trop-2-expressing cell lines, and potency to inhibit growth of these cell lines at nanomolar concentrations. 2L-Rap(Q)-hRS7 also suppressed tumor growth in a prophylactic model of nude mice bearing Calu-3 human non-small cell lung cancer xenografts, with an increase in the median survival time (MST) from 55 to 96 days ($P<0.01$). These results demonstrate the superior efficacy of 2L-Rap(Q)-hRS7 as a therapeutic for various Trop-2-expressing cancers, such as cervical, breast, colon, pancreatic, ovarian, and prostate cancers.

Material and Methods

Cell Lines and Cell Culture Cervical cancer line (ME-180), breast cancer lines (T-47D, MDA-MB-468, SK-BR-3), prostate cancer lines (DU-145, PC-3, 22R$^{v1}$), lung adenocarcinoma line (Calu-3), pancreatic cancer lines (Capan-1, BxPC-3, and AsPc-1), and ovarian cancer line (SK-OV-3) were obtained from American Type Culture Collection (Manassas, Va.), and cultured at 37o C in 5% $CO_2$ in RPMI 1640 medium supplemented with 10% heat-inactivated fetal bovine serum (FBS), 2 mM L-glutamine, 200 units/mL penicillin, and 100 μg/mL streptomycin.

Antibodies and Reagents

Milatuzumab (hLL1, anti-CD74), hRS7, recombinant ranpirnase (rRap), and a mouse anti-Rap IgG were from Immunomedics. Fluorescein isothiocynate (FITC)-, phycoerythrin (PE)-, or horseradish peroxidase (HRP)-conjugated goat anti-human (GAH) or goat anti-mouse (GAM) IgG, Fc-specific, antibodies were purchased from Jackson ImmunoResearch Labs (West Grove, Pa.). GAH IgG conjugated to Alexa Fluor 488, human transferrin conjugated to Alexa Fluor 568, and Hoechst 33258 were acquired from Molecular Probes (Invitrogen, Carlsbad, Calif.). All restriction enzymes were obtained from New England Biolabs (Beverly, Mass.).

Vector Construction

The construction of the plasmidpdHL2-Rap-L-hLL1-γ4P for expressing 2L-Rap-hLL1-γ4P was as described in Example 2 below. The expression vector pdHL2-Rap (Q)-L-hLL1-γ4P was derived from pdHL2-Rap-L-hLL1-γ4P by replacing Rap with Rap(Q) and the plasmid pdHL2-Rap(Q)-L-hRS7-γ1 for expressing (Q)-hRS7 was constructed by subcloning Rap(Q) gene from pdHL2-Rap(Q)-L-hLL1-γ4P into pdHL2-hRS7-γ1 vector. Briefly, an EcoRV restriction site was introduced at the N-terminal (5') side of the hRS7 VL gene using suitable primers by PCR. The XbaI-EcoRV fragment of pdHL2-Rap(Q)-L-hLL1-γ4P containing Leader peptide-Rap-Linker was ligated with the EcoRV-BamHI fragment generated by PCR containing hRS7 VL gene into an intermediate vector, pBS-Rap(Q)-L-hRS7. The Xba-BamHI fragment of pdHL2-hRS7-γ1 was replaced with Xba-BamHI fragment of pBS-Rap(Q)-L-hRS7.

Transfection and Selection

The pdHL2-Rap(Q)-L-hRS7-γ1 vector (30 μg) was linearized with SalI and transfected by electroporation into Sp2/0 cells, which were grown in complete hybridoma serum-free medium supplemented with 10% Low-IgG FBS, 100 units/mL penicillin and 100 μg/mL streptomycin, 2 mM L-glutamine, 1 μM sodium pyruvate, 100 μM essential amino acids, and 0.05 μM methotrexate (MTX). Culture supernatants from wells of surviving cells were analyzed for the expression of the fusion protein by ELISA using HRP-conjugated GAH IgG, Fc-specific, antibody. Positive clones were expanded and frozen for future use.

Expression and Purification

Cells were grown in roller bottles to terminal culture (10-20% viability). The supernatant was filtered and applied to a Protein A column, previously equilibrated with a pH 8.5 buffer containing 20 mM Tris-HCl and 100 mM NaCl. Following loading, the column was washed with a 100-mM sodium citrate buffer (pH 7.0) and eluted with 100 mM sodium citrate buffer (pH 3.5) to obtain the fusion protein. The peak containing the product was adjusted to pH 7.0 using 3 M Tris-HCl, pH 8.5, and dialyzed against 40 mM phosphate-buffered saline (PBS). Following concentration, the product was filtered through 0.22 μm filters and stored at 2-8° C.

Size-Exclusion HPLC and SDS-PAGE Analyses

The purity and molecular integrity of (O)-hRS7 was assessed by size-exclusion HPLC using a Zorbax column purchased from BioRad (Hercules, Calif.), and by SDS-PAGE under reducing conditions using 4-20% Tris-glycine gels (PAGEr® Gold Precast Gels, Cambrex, Rockland, Me.).

In Vitro Transcription and Translation (IVTT) Assay

RNase activity was determined in a cell-free system by measuring the activity of de novo synthesized luciferase using the TNT® Quick Coupled Transcription/Translation System (Promega, Madison, Wis.) per manufacturer's instructions. Briefly, various test samples at concentrations ranging from 10 μM to 100 nM in 2 μL were added to 8 μL of the TNT® Quick Master Mix containing methionine and luciferase-control DNA and incubated for 2 h at 30° C. in a 96-well, round-bottom plate from which 2 μL were removed for analysis with 50 μL, Bright-Glo substrate in a black 96-well, flat-bottom plate. Plates were read on an Envision chemiluminescence reader. Relative luciferase units (RLU) were plotted against the concentration of test samples.

Yeast tRNA Degradation Assay

RNase activity was also determined by measuring the amount of perchloric acid-soluble nucleotides formed using yeast tRNA (Invitrogen) as substrate (Newton et al., Blood 2001; 97:528-35). Each sample was prepared with RNase-free water (Ambion, Austin, Tex.) in a 1.5-mL RNase-free Eppendorf tube to contain, in a final volume of 100 μL, 5 nM (Q)-hRS7 or rRap; 10 mM HEPES, pH 6.0; 200 μg/mL human serum albumin; and a predetermined concentration of tRNA ranging from 100 μg/mL (3.09 μM) to 600 μg/mL (18.54 μM). The enzymatic reaction was performed at 37° C. for 2 h and terminated by adding 233 μL of 3.4% ice-cold perchloric acid to each sample on ice. After 10 min, samples were centrifuged in a microcentrifuge at 12,000 rpm for 10 min in the cold room. An aliquot was removed from the supernatant of each sample and diluted 10-fold with water, from which the optical density (OD) at 260 nm was measured against water as blank. The initial rates were calculated for each substrate concentration by dividing the corresponding OD value with the reaction time (7200 sec) and plotted against the substrate concentrations to determine kcat/Km, which under the conditions of Km>>[S] according to the Michaelis-Menten equation, should equal to the slope of the resulting least square line divided by the total enzyme concentration (5 nM for rRap and 10 nM for (Q)-hRS7).

Cell Binding Measurements

An ELISA-based method was used to evaluate binding of (Q)-hRS7 to select cell lines as follows. Cells were plated into a black 96-well, flat-bottom plate ($1\times10^5$ cells/well; 100 µL/well) and incubated overnight at 37° C. in a 5% $CO_2$ humidified incubator. The next day, plates containing the cells were removed from the incubator and the media flicked out of the wells followed by gentle patting dry on paper towels. Each well then received 50 µL of fresh growth media. Serial 1:4 dilutions (200 nM through $1.9\times10^{-4}$ nM) of (Q)-hRS7 were made in assay media (RPMI 1640; 10% FBS complete media), and added (50 µL/well) in triplicates to corresponding wells (final concentrations 100 nM through $0.95\times10^4$ nM). After incubation for 1.5 h at 4° C., the plates were centrifuged at 600×g for 2 min, blotted dry on paper towels after removal of the media, and washed by adding 150 µL of ice-cold media into each well followed by centrifugation at 600×g for 2 min. The media was removed and plates were blotted dry. HRP-conjugated GAH antibody was used at a 1:20,000 dilution and was then added to all the wells (100 µL/well). For background control, one set of wells received only cells plus the secondary antibody. The plate was incubated for 1 h at 4° C. Afterwards, the plate was centrifuged and blotted dry. The cells were then washed twice with ice-cold media followed by a third wash with ice-cold PBS. The procedures of centrifugation, media removal and plate-blotting were repeated following each wash.

After the last washing step, LumiGLO (KPL, Gaithersburg, Md.) was added to all wells (100 µL/well) and the plate read for luminescence using an Envision plate reader. Data were analyzed using GraphPad Prism software to determine the apparent affinity, which is the concentration corresponding to half-maximal saturation. In each experiment, hRS7 and hLL1 were included as positive and isotype controls, respectively. Alternatively, binding of (Q)-hRS7 to human cancer cell lines was determined by flow cytometry on a Guava PCA (Guava Technologies, Inc., Hayward, Calif.), using the manufacturer's reagents, protocols, and software. Similar studies were performed in parallel for each cell line with hRS7 and hLL1. Briefly, about $5\times10^5$ cells of the various lines to be analyzed were obtained and resuspended in PBS/1% BSA (bovine serum albumin). Cells were centrifuged, resuspended in 100 µL of PBS/1% BSA containing 10 µg/mL (Q)-hRS7, hRS7, or hLL1, and incubated at 4° C. for 45 min. After washing twice with PBS/1% BSA, with each wash followed by centrifugation, cells were resuspended in 50 µL of FITC-conjugated GAH, Fc specific, antibody (1:25 dilution) and incubated for 30 min at 4° C. Cells were analyzed by flow cytometry after washing twice with PBS/1% BSA and resuspended in 0.5 mL of PBS/1% BSA. To separate dead from viable cells 1 µg/mL of propidium iodide was added. For each analysis 10,000 cells were acquired.

Cell Proliferation Assay

Tumor cells were seeded in 96-well plates ($1\times10^4$ cells per well) and incubated with test articles at 0.01 to 100 nM for 72 h. The number of living cells was then determined using the soluble tetrazolium salt, MTS [3-(4,5-dimethylthiazol-2-yl)-5-(3-carboxymethoxyphenyl)-2-(4-sulfophenyl)-2H-tetrazolium], following the manufacturer's protocol. The data from the dose-response curves were analyzed using GraphPad Prism software to obtain EC50 values (the concentration at which 50% inhibition occurs).

Colony-Formation Assay

Tumor cells were trypsinized and plated in 60-mm dishes ($1\times10^3$ cells). Cells were treated with each test article and allowed to form colonies. Fresh media containing the test article were added every 4 days, and after 2 weeks of incubation, colonies were fixed in 4% formaldehyde and stained with Giemsa. Colonies>50 cells were enumerated under a microscope.

Internalization Studies by Fluorescence Microscopy

ME-180 cells were placed (2000 cells in 500 µL per well) in 8-well, Lab-Tek™ II chamber slides (Nalge Nunc International, Naperville, Ill.) and incubated with (Q)-hRS7 (10 µg/mL) or hRS7 (6 µg/mL) at 37° C. for 16 h. All subsequent steps were performed at room temperature. After washing twice with PBS/2% BSA or twice with PBS/2% BSA followed by twice washing with 0.1 M glycine, pH 2.5 (500 µL, 2 min), cells were fixed in 4% formalin for 15 min, washed twice with PBS, then probed with a mouse anti-Rap mAb followed by PE-conjugated GAM, Fc-specific, antibody, or directly with FITC-conjugated GAH, Fc specific, antibody to reveal the location of (Q)-hRS7 or hRS7 using a fluorescence microscope.

A second study to address the subcellular location of (Q)-hRS7 was performed as follows. Alexa Fluor 568-conjugated human transferrin (hTf) was added with (Q)-hRS7 (10 µg/mL) or hRS7 (6 µg/mL) to MDA-MB-468 human breast cancer cells placed (3000 cells in 500 µL per well) in 8-well chamber slides. After incubation at 37° C. for 2 h, cells were washed and fixed as described above, then treated with Alexa Fluor 488-conjugated GAH IgG for 15 min at room temperature. After washing twice with PBS, cells were treated with Hoechst 33258 for 15 min at room temperature, washed, and examined under a fluorescence microscope.

In Vivo Toxicity

Naïve BALB/c mice (female, 7 weeks old, Taconic Farms, Germantown, N.Y.) were injected intravenously with various doses of (Q)-hRS7 ranging from 25 to 400 µg per mouse and were monitored daily for visible signs of toxicity and body weight change. The maximum tolerated dose (MTD) was defined as the highest dose at which no deaths occurred and the body weight loss was 20% or less of pretreatment animal weight (approximately 20 g). Animals that experienced toxic effects were euthanized.

Therapeutic Efficacy in Tumor-Bearing Mice

Female NCr homozygous athymic nu/nu mice of approximately 20 g (5 weeks old when received from Taconic Farms) were inoculated s.c. with $1\times10^7$ Calu-3 human NSCLC cells and monitored for tumor growth by caliper measurements of length×width of the tumor. Tumor volume was calculated as (L×W2)/2. Once tumors reached approximately 0.15 $cm^3$ in size, the animals were divided into treatment groups of five per group. Therapy consisted of either a single i.v. injection of 50 µg of (O)-hRS7 or two injections of 25 µg administered seven days apart. A control group received saline. Animals were monitored daily for signs of toxicity and were humanely euthanized and deemed to have succumbed to disease progression if tumors reached greater than 2.0 cm$^3$ in size or became ulcerated. Additionally, if mice lost more than 20% of initial body weight or otherwise became moribund, they were euthanized. Survival data were analyzed using Kaplan-Meier plots (log-rank analysis) with GraphPad Prism software. Differences were considered statistically significant at P<0.05.

Results

Purity and Molecular Integrity (Q)-hRS7 was shown by size-exclusion HPLC to consist of a single peak (not shown) with the observed retention time (7.8 min) indicating a larger molecular size than IgG. The purity of (Q)-hRS7 was also supported by the observation of only two bands on reducing SDS-PAGE, one of ~50 kDa attributed to the heavy chain of hRS7 and the other of 37 KDa attributed to the Rap(Q)-fused L chain (not shown).

Binding Analysis

The reactivity of (Q)-hRS7 with Trop-2-expressing cell lines was initially assessed by ELISA and demonstrated for PC-3 (FIG. 2A) and Calu-3 (FIG. 2B), both yielding an apparent dissociation constant ($K_D$) about two-fold higher than that of hRS7 (0.28 nM vs. 0.14 nM). No binding was observed for the Trop-2-negative 22Rv1 (FIG. 2C). Subsequent studies were performed by flow cytometry in a total of 10 Trop-2-expressing cell lines, and the results (not shown), indicate that there was virtually no difference in the binding property of (Q)-hRS7 from that of hRS7.

RNase Activity

Figure 3:
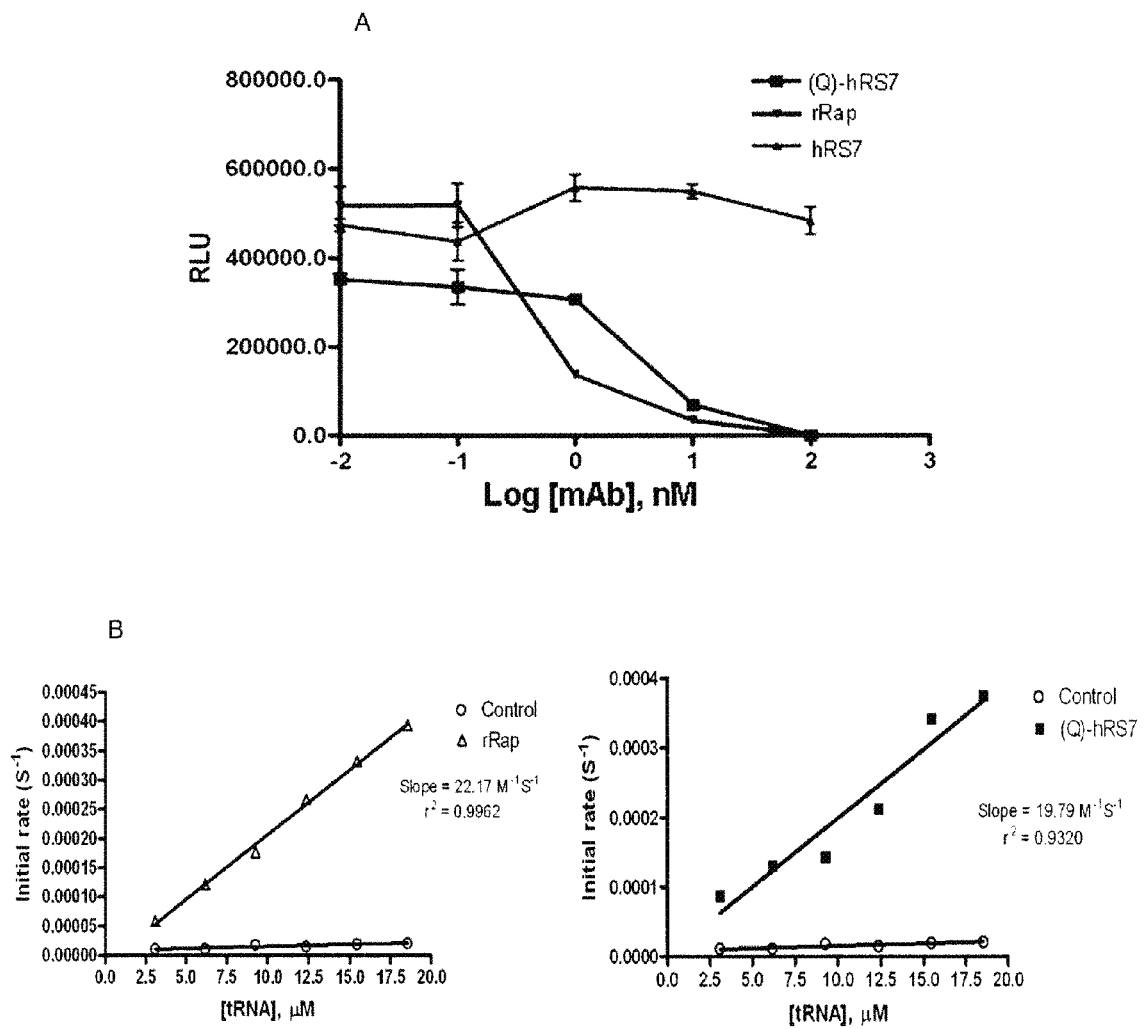
FIG. 3. Representative data of the IVTT assay (A) showing (Q)-hRS7 and rRap have comparable RNase activity; and (B) plotting the initial rates of rRap (left) and (O)-hRS7 (right) activity against the concentrations of yeast tRNA to determine kcat/Km.

The IVTT assay measures inhibition of protein synthesis due to mRNA degradation by RNase. As shown in FIG. 3A, (Q)-hRS7 and rRap have comparable RNase activity in this cell-free assay, whereas no enzymatic activity was observed for hRS7. Using yeast tRNA as substrate, we estimated the kcat/Km ($10^9 M^{-1} s^{-1}$) of rRap and (Q)-hRS7 to be 4.10 (±0.42) and 1.98, respectively. Thus the catalytic efficiency of (Q)-hRS7 based on the concentration of Rap is about 50% of rRap, which was similar to the reported 40% catalytic efficiency of LL2-onconase as compared to the native Rap (Newton et al., Blood 2001; 97:528-35). A plot of the initial rates versus the concentrations of tRNA from a representative set of experiments is shown in FIG. 3B.

In Vitro Cytotoxicity

Based on the results of the MTS assay, (Q)-hRS7 is most potent against ME-180 (FIG. 4A), T-47D (FIG. 4B), MDA-MB-468, and Calu-3, with EC50 values of 1.5, 2.0, 3.8, and 8.5 nM, respectively. For those cell lines showing less than <50% growth inhibition at 100 nM of (Q)-hRS7 with the MTS assay, we also performed colony-formation assays to confirm that (Q)-hRS7 was cytotoxic at 10 or 100 nM to DU-145, PC-3, MCF7, SK-BR-3, BxPC-3, Capan-1, and SK-OV-3 (not shown). Representative results are shown for DU-145 (FIG. 4C) and PC-3 (FIG. 4D). In both assays, hRS7, rRap, and the combination of hRS7 and rRap showed little, if any, toxicity at 100 nM in all the cell lines evaluated. The Trop-2-negative AsPC-1 was resistant to (Q)-hRS7 in both assays.

Internalization and Subcellular Location

The internalization of (Q)-hRS7 into ME-180 cells was clearly revealed for samples that were fixed after washing with PBS/0.2% BSA or with a low pH glycine buffer to strip membrane-bound proteins (not shown). The distribution pattern of intracellular (Q)-hRS7 in ME-180, as detected directly by FITC conjugated GAH or indirectly by PE-conjugated GAM via mouse anti-Rap IgG, appeared to be nearly identical, suggesting that (Q)-hRS7 remains intact following entry into these cells (not shown). The subcellular location of (Q)-hRS7 was further probed in MDA-MB-468 cells using fluorescence-labeled hTf as a marker for the recycling endosome and Hoechst 33258, which stains the nucleus. It was apparent from the results that (Q)-hRS7 and hTf occupy the same subcellular location in MDA-MB-468 when examined after incubation at 37° C. for 2 h (not shown). In both cell lines, hRS7 exhibited internalization characteristics similar to (Q)-hRS7, except that it was not visualized by PE-GAM/anti-Rap, as expected (data not shown).

MTD in Mice

We determined the MTD of (Q)-hRS7 in normal BALB/c mice given a single intravenous injection to be between 50 μg and 100 μg. Other 2L-Rap-X or 2L-Rap(Q)-X fusion proteins made to date have a similar MTD range. In addition, we determined the MTD of (Q)-hRS7 for multiple injections in naïve SCID mice to be 80 μg by giving 20 μg every five days four times (q5dx4).

Therapeutic Efficacy in Tumor-Bearing Mice

Figure 5:
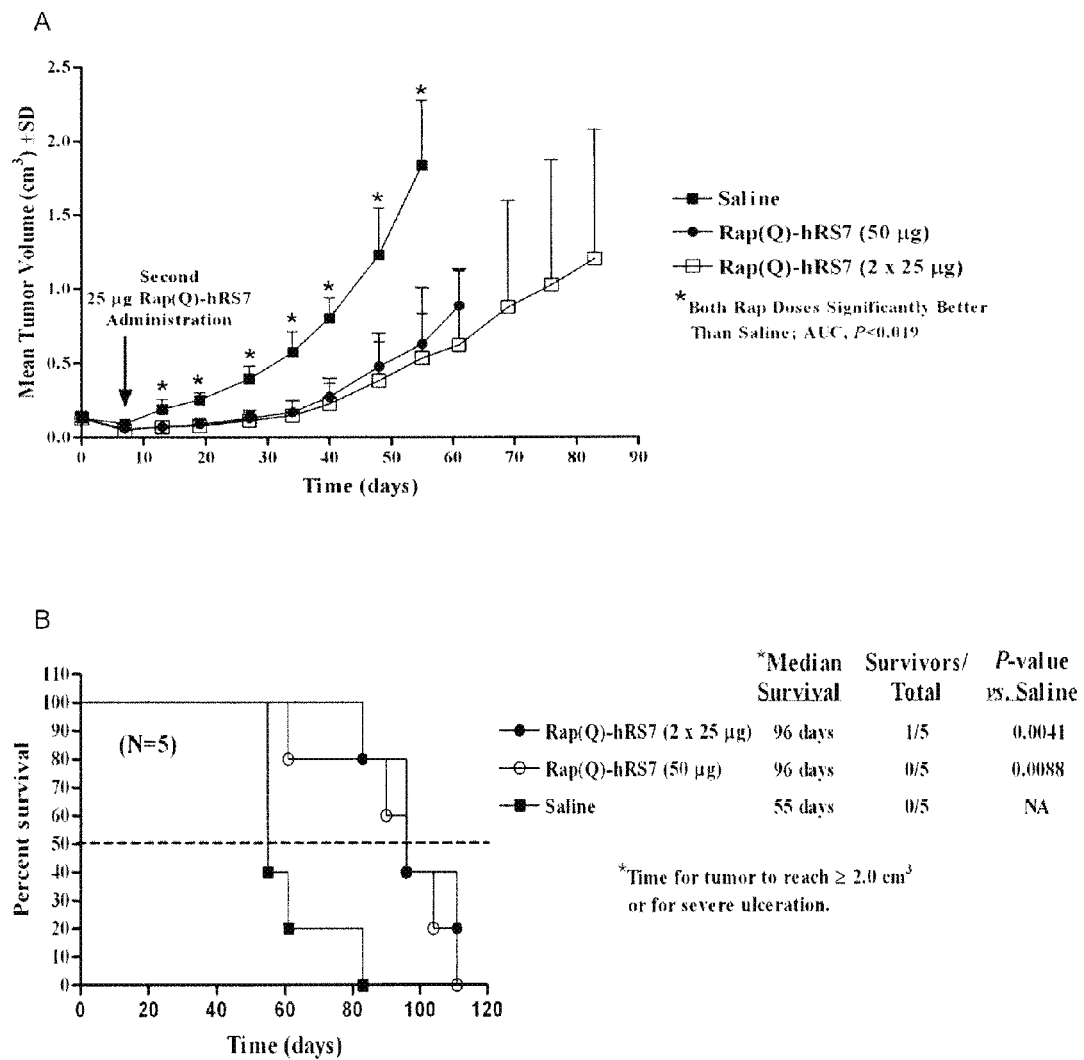
FIG. 5. Therapeutic efficacy of (Q)-hRS7 demonstrated in a Calu-3 human xenograft model to inhibit tumor growth (A) and increase MST (B). Nude mice were inoculated subcutaneously with $1 \times 10^7$ Calu-3 cells. When tumors reached approximately 0.15 cm$^3$, mice were treated with either a single intravenous dose of 50 µg or two injections of 25 µg administered seven days apart. Control animals received saline.

As shown in FIG. 5A, either treatment (single dose, 50 μg or two doses of 25 μg given 5 days apart) with (Q)-hRS7 significantly inhibited the growth of Calu-3 xenografts compared to untreated controls (P<0.019), with the median survival time increased from 55 days to 96 days (P<0.01; FIG. 5B).

Discussion

Compared to immunotoxins made from toxins of plant or bacterial origin (Kreitman, AAPS J 2006; 8:E532-51), for which clinical trials in cancer therapy have been completed or are ongoing for quite a few (Pastan et al., Nat Rev Cancer 2006; 6:559-65; Pastan et al., Annu Rev Med 2007; 58:221-37; Kreitman, BioDrugs 2009; 23:1-13), the advancement of antibody-targeted RNases, referred to as ImmunoRNases (De Lorenzo et al., FEBS Lett 2002; 516:208-12; Cancer Res 2004; 64:4870-4), is relatively moderate, with the majority developed for treating hematological malignancies and the targeting components conferred by some forms of scFv (Schirrmann et al., Exp Opin Biol Ther 2009; 9:79-95). To date, ImmunoRNases have not been evaluated in patients with any cancer.

Two difficulties noted in the clinical development of other plant or microbial immunotoxins are undesirable toxicity and immunogenicity. Normal tissue toxicity observed with these immunotoxins includes vascular leak syndrome (VLS), hemolytic uremic syndrome (HUS), and hepatotoxicity (Kreitman, BioDrugs 2009; 23:1-13). The structural motif (x)D(y) identified to be responsible for the binding of ricin A-chain or IL-2 to endothelial cells is absent in the native sequence of Rap(Q), and hRS7 is not crossreactive with human endothelial cells. We therefore consider the likelihood of (Q)-hRS7 causing VLS to be remote. The large size of (Q)-hRS7 (~180 kDa), which poses a potential concern for less rapid penetration of tumors (Yokota et al., Cancer Res 1992; 52:3402-8), should prevent its clearance via kidneys and mitigate the risk for HUS. As for hepatotoxicity, we note that BL22, a recombinant anti-CD22 immunotoxin composed of the disulfide-stabilized Fv of RFB4 fused to PE38, and similar immunotoxins such as LMB-2 (anti-Tac(Fv)-PE38), also had a very low MTD in mice due to nonspecific liver toxicity, yet BL22 has been reported to be safe and efficacious in clinical trials of patients with hairy-cell leukemia (Kreitman et al., N Engl J Med 2001; 345:241-7). Thus, the dose-limiting hepatotoxicity commonly observed in mice may be rarely manifested in humans (Kreitman, BioDrugs 2009; 23:1-13). Immunogenicity, on the other hand, is a more general problem. Most genetically-engineered immunotoxins that have been evaluated in cancer patients induced a strong humoral immune response, which shortens the serum half-life and prevents further administration. Several approaches to reduce the immune response have been tested in experimental animals, with some success reported for deoxyspergualin (Pai et al., Cancer Res 1990; 50:7750-3) and CTLA4Ig (Sieall et al., J Immunol 1997; 159:5168-73), and clinical testing of these and other immunosuppressive agents in combination with immunotoxins has been proposed (Frankel, Clin Cancer Res 2004; 10:13-5). (Q)-hRS7 will be less immunogenic, because it comprises the fusion of a humanized antibody to a toxin that appears to induce little antibody response in patients (Mikulski et al., J Clin Oncol 2002; 20:274-81).

The cytotoxicity of an immunotoxin requires its entry into the target cell with subsequent translocation to the cytosol. Although the intracellular pathways following internalization have been reported for ranpirnase (Rodriguez et al., J Cell Sci 2007; 120:1405-11; Haigis and Raines, J Cell Sci 2003; 116:313-24; Wu et al., J Biol Chem 1995; 270:17476-81) and other RNases (Wu et al., J Biol Chem 1995; 270:17476-81; Leich et al., J Biol Chem 2007; 282:27640-6; Bracale et al., Biochem J 2002; 362:553-60), as well as for ImmunoRNases comprising human pancreatic RNase fused to either a human anti-ErbB2 scFv (De Lorenzo et al., Cancer Res 2004; 64:4870-4; FEBS Lett 2007; 581:296-300) or a human anti-CD30 scFv-Fc (Menzel et al., Blood 2008; 111:3830-7), a complete understanding is yet to emerge. Our internalization experiments indicate that (Q)-hRS7 is co-localized with hTf when examined at 2 h after adding to MDA-MB-468, suggesting that (Q)-hRS7 may exit directly from endosomes into the cytosol, as proposed for ranpirnase (Haigis and Raines, J Cell Sci 2003; 116:313-24). The close resemblance of the fluorescence images observed in ME-180 for intracellular (Q)-hRS7 between anti-Rap and anti-human Fc further suggests the ability of (Q)-hRS7 to resist degradation by proteases during the endocytic process.

Although the in vitro potency of (Q)-hRS7 was found to vary among Trop-2-expressing cell lines when measured by the 3-day MTS assay, which may be partially attributed to differential intracellular routing, the cytotoxicity of (Q)-hRS7 was unequivocally demonstrated at 10 nM for all cell lines using the 14-day colony-formation assay. In addition to its potent cytotoxicity against diverse cancer cell lines in vitro, (Q)-hRS7 was shown to be effective in inhibiting the growth of Calu-3 human lung cancer xenografts in nude mice, thus validating the antitumor activity and stability of (Q)-hRS7 in vivo, as well as confirming the suitability of adding Trop-2 to the current list of antigens on solid cancers targeted by immunotoxins (Kreitman, AAPS J 2006; 8:E532-51; Pastan et al., Nat Rev Cancer 2006; Pastan et al., Annu Rev Med 2007; 58:221-37; Schirrmann et al., Exp Opin Biol Ther 2009; 9:79-95).

In conclusion, we have demonstrated that an amphibian RNase recombinantly fused with a humanized anti-Trop-2 antibody shows selective and potent cytotoxicity against a variety of epithelial cancers, both in vitro and in vivo.

Example 2

Expression, and Characterization of 2L-Rap-hLL1-γ4P

As used below, rap represents ranpirnase.
Construction of pdHL-IgG4P Variant:
B13-24 cells containing an IgG4 gene were purchased from ATCC (ATCC Number CRL-11397) and genomic DNA was isolated. Cells were washed with PBS, resuspended in digestion buffer (100 mM NaCl, 10 mM Tris-HCl pH 8.0, 25 mM EDTA, 0.5% SDS, 0.1 mg/ml proteinase K) and incubated at 50° C. for 18 h. The sample was extracted with an equal volume of phenol/chloroform/isoamyl alcohol and precipitated with 7.5 M $NH_4Ac$/100% EtOH. Genomic DNA was recovered by centrifugation and dissolved in TE buffer. Using genomic DNA as template, the IgG4 gene was amplified by PCR.

Amplified PCR product was cloned into a TOPO-TA sequencing vector (Invitrogen) and confirmed by DNA sequencing. The SacII-EagI fragment containing the heavy chain constant region of IgG1 in pdHL-hLL2 was replaced with SacII-EagI of the TOPO-TA-IgG4 plasmid to produce the pdHL2-hLL2-IgG4 (pdHL2-hLL2-γ4) vector.

$IgG_4$-Proline Mutation

A Ser228Pro mutation was introduced in the hinge region of IgG4 to avoid formation of half-molecules. A mutated hinge region 56 bp fragment (PstI-StuI) was synthesized, annealed and replaced with the PstI-StuI fragment of $IgG_4$. This construction resulted in a final vector pdHL2-hLL2-γ4P Construction of pdHL2-hLL1-γ4P The XbaI-HindIII fragment of pdHL2-hLL2-γ4P was replaced with the Xba-HindIII fragment of pdHL2-hLL1 containing Vk and VH regions to generate the hLL1-γ4P construct.

Construction of pdHL2-2L-rap-hLL1-γ4P

A flexible linker comprising three copies of a four glycine-one serine monomer was used to attach the C-terminus of Rap to the N-terminus of Vk of hLL1. One rap molecule was attached at the N-terminus of each light chain. Construction of the DNA for this molecule was done by PCR. The Xba-BamHI fragment of pdHL2-hLL1-γ4P was replaced with the Xba-BamHI (Xba-Leader-rap-Linker-Vk-BamHI) fragment of pBS-2L-rap-hLL1 to complete the final vector pdHL2-2L-rap-hLL1-γ4P.

Transfection

The vector DNA (30 μg) was linearized with SalI enzyme and transfected into NSO ($4 \times 10^6$ cells/mL) or Sp2/0-Ag14 ($5 \times 10^6$ cells/mL) myeloma cells by electroporation (450 V). Cells were grown in complete Hybridoma-SFM medium supplemented with low-IgG FBS (10%), penicillin (100 units/mL), streptomycin (100 μg/mL), L-glutamine (2 mM), sodium pyruvate (1 mM), non-essential amino acids (100 μM), and methotrexate (0.1 μM). Positive clones were screened by ELISA. Briefly, plates were coated with 50 μl of an anti-rap antibody at 5 μg/mL in PBS medium and incubated at 4° C. over night. After washing the plate with PBS and blocking with 2% BSA cell culture supernatants were added. HRP-conjugated goat anti-human IgG.sub.4 antibodies were used for detection and OPD was used as a substrate for color development. Plates were read at 490 nm. Positive clones were expanded and frozen for future use. Clone C6 was identified as the best producer and used for further development.

Expression and Purification

Cells were grown in 2 roller bottles with 500 ml media in each to terminal culture (10-20% viability) and the cells were removed by centrifugation. Culture supernatant was filtered and applied to a Protein A column, equilibrated with a 20 mM Tris-HCl/100 mM NaCl buffer (pH 8.5). Following the loading, the column was washed with a 100 mM sodium citrate buffer (pH 7.0) and eluted with 100 mM sodium citrate buffer (pH 3.5) to obtain the fusion protein. The peak containing the product was adjusted to pH 7.0 using 3 M Tris-HCl, pH 8.0 and dialyzed against 10 mM PBS buffer. Following concentration, the product was filtered through 0.22 μm filters and stored at 2-8° C. From the 1-L culture, 16 mg were recovered after purification.

Characterization of 2L-rap-hLL1-γ4P

HPLC:

Protein purity and concentration were checked on HPLC. A sharp single peak was observed at 7.7 min (not shown), with the retention time indicating the molecule was larger than IgG.

SDS-PAGE:

SDS-PAGE was performed under reducing conditions using 4-20% Tris-Glycine gels. A band related to the heavy chain of expected size about 50 kD and two bands of molecular mass about 37 and 39 kD, both larger than the light chain of hLL1 (about 25 kD), were observed (not shown). The presence of the two light chains was shown to be due to glycosylation of rap on the fusion protein (see below).

Mass Spectrometry:

Mass spectrometry was performed at The Scripps Research Institute, CA, by the MALDI-TOF method. Two samples were sent for analysis, one in the native state (1.6 mg/mL in 10 mM PBS) and the other in reduced state (1.6 mg/mL in 1 mM HEPES/10 mM DTT, pH 7.5 buffer). The native sample showed one major peak of mass 177150, which is in good agreement with the MW of one IgG plus two raps (not shown). The reduced sample showed three major peaks at 50560 (corresponding to the heavy chain), 38526 and 36700 (corresponding to the two light chains containing rap) (not shown).

Western Blotting:

To confirm the presence of rap in the purified protein, western blotting was performed. Samples from SDS-PAGE gels under reducing condition were electro-transferred onto PVDF membranes. After blocking with 5% BSA, mouse anti-rap antibodies were added at 1:10,000 dilution or 10 ng/ml and incubated for 1 hr. After washing, HRP-conjugated goat anti-mouse Fc antibodies were added and incubated for 1 hr. After washing six times, LumiGlo™ (Kirkegaard & Perry Laboratories) substrate was added and Kodak film was developed. Both bands corresponding to the fused light chains were detected on the film confirming the presence of rap on both light chains (not shown).

Treatment with N-glycosidase:

As rap has a potential N-glycosylation site, Asn-X-Thr/Ser, Asn69-Val70-Thr71, the observation of two light chains with a molecular mass, difference of 2 kD might be the result of uneven glycosylation of rap. To investigate this possibility rap-hLL1 antibody was incubated with N-glycosidase (New England Biolabs) under denatured condition according to supplier's recommendations. After N-glycosidase treatment the two bands corresponding to the two light chains converged into one (the faster migrating band), thus confirming that uneven distribution of carbohydrate was the reason for observation of two bands on SDS-PAGE (not shown). Further support was provided by the observation of only one Rap-fused light chain when Rap(N69Q), a variant of Rap with the glycosylation site removed, is substituted for Rap in the recombinant construct (data not shown).

Figure 6:
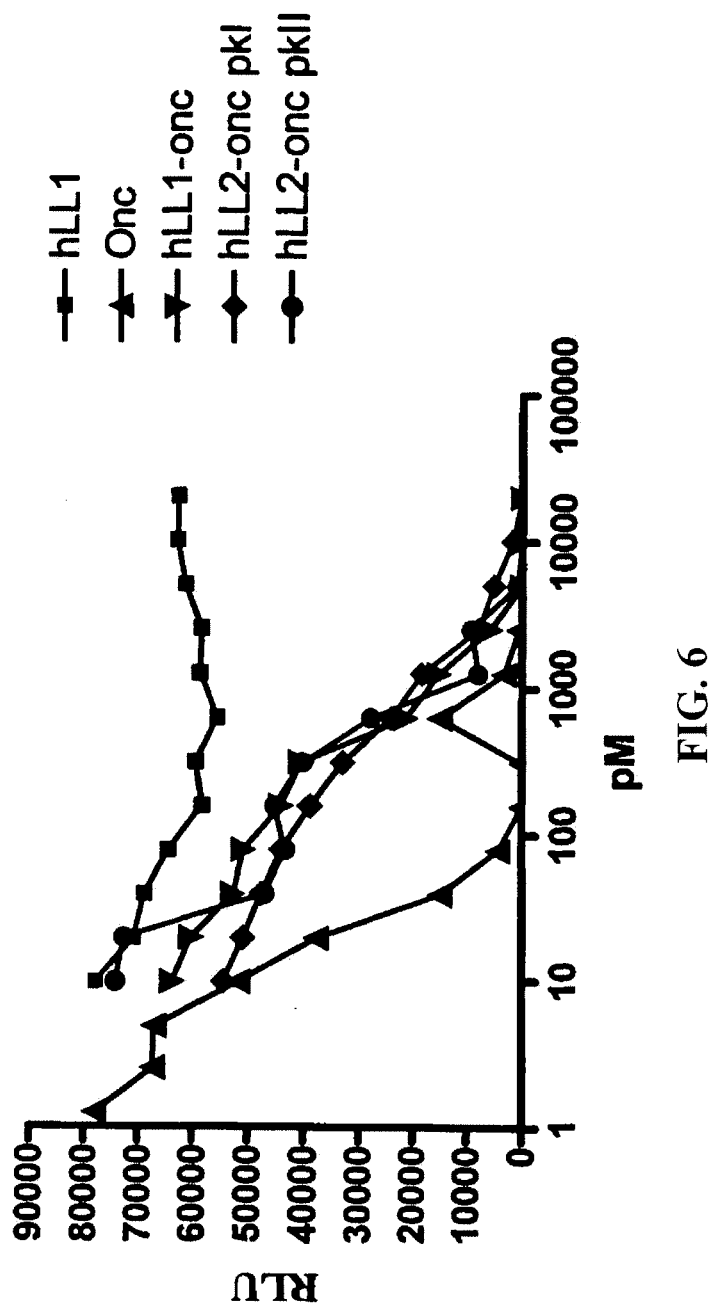
FIG. 6 shows RNase Activity by in-vitro transcription translation assay.

Activity of Rap:

RNase activity was tested by TNT® Quick Coupled Transcription/Translation System (Promega) using Bright-Glo™ Luciferase Reporter Assay system (Promega) according to supplier's recommendations. The principle for this assay was measurement of inhibition of protein synthesis (mRNA degradation) as a result of RNase activity using luciferase reporter system. Samples were prepared in different dilutions, free rap (0.001-2.5 nM), hLL1-rap (0.01-20 nM) or chemical conjugates of hLL2-rap, represented as PK1-LL2-One and PKII-LL2-One (0.01-20 nM). Each sample (5 uL) was mixed with 20 μl of TNT master mix, incubated for 2 hr at 30° C. in a 96-well plate, from which 1 μl was removed for analysis with 50 μl of Bright-Glo™ substrate. The results are shown in FIG. 6, using Excel or Prism Pad software. $EC_{50}$ values were about 300 pM for rap-hLL1 and chemical conjugates of hLL2-One, and 30 μM for free rap.

Competition Binding for WP

Figure 7:
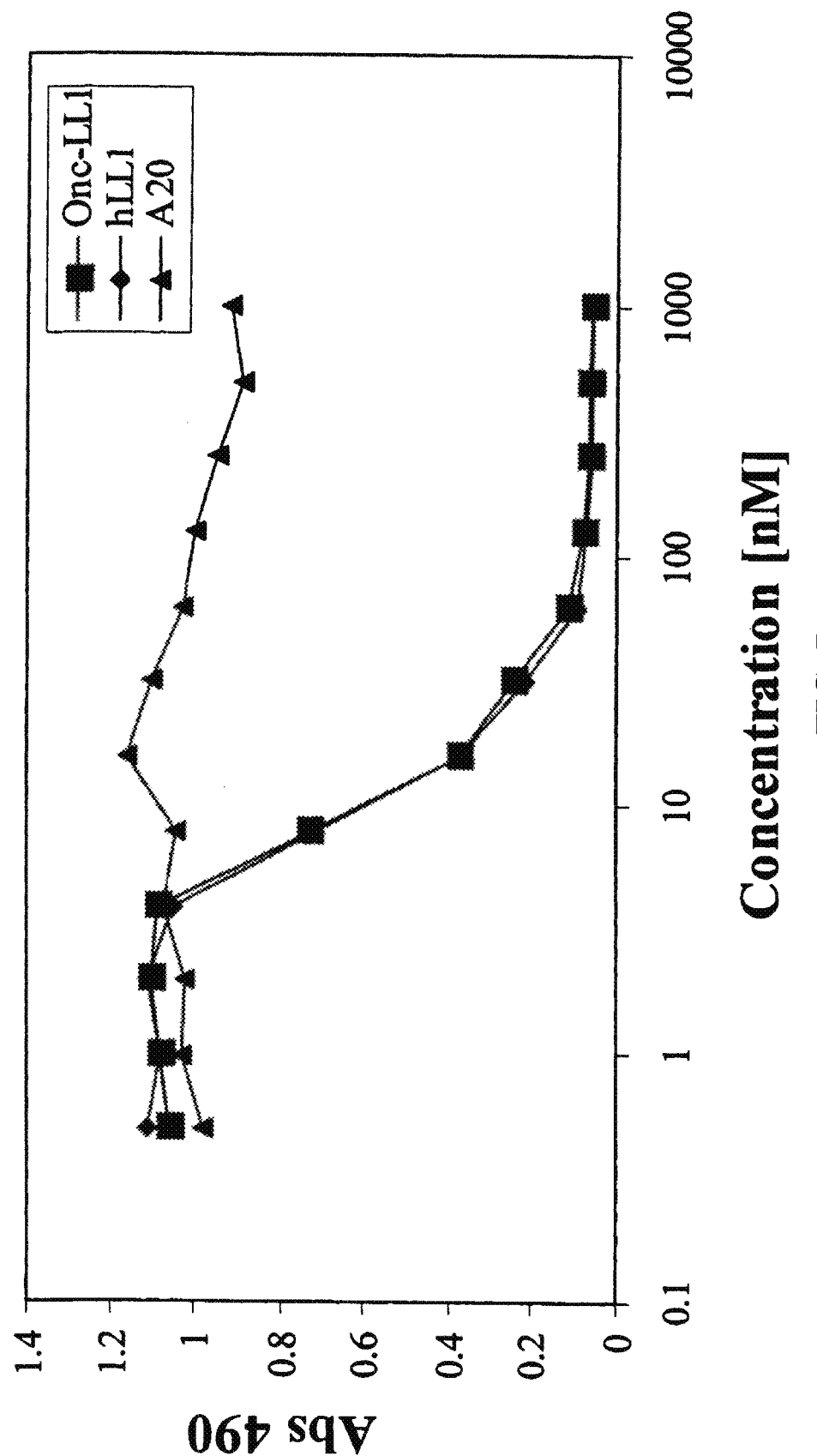
FIG. 7 shows a competition binding assay, demonstrating that hLL1 and rap-hLL1 fusion protein both have the same affinity for WP, an anti-idiotype antibody of hLL1.

WP is an anti-idiotype antibody of hLL1. The affinity of rap-hLL1 antibody in comparison with hLL1 antibody against WP was evaluated by competition binding assay. Briefly, 96-well plates were coated with 50 μl of WP at 5 μg/mL and incubated at 4° C. over night. Three types of protein samples, hLL1, rap-hLL1 or hA20 were prepared in different 2× dilutions (final concentrations range between 0.49-1000 nM), mixed with an equal volume of 2×HRP-conjugated mLL1 antibody (final dilution is 1/20,000). 50 μL of protein samples mixed with HRP-conjugated-mLL1 as described above was added to each well and incubated for 1 hr. After washing, OPD substrate containing $H_2O_2$ was added and plates were read at 490 nm. As shown in FIG. 7, protein concentration against absorbance was plotted using Excel or Prism Pad graph software. hA20 (humanized anti-CD20 antibody) was used as negative control. From FIG. 7, it is apparent that rap-hLL1 has a similar binding affinity to hLL1 and the negative control, hA20, has no affinity at all. Similar results were obtained using Raji cells as the source of antigens.

In vitro Cytotoxicity

Figure 8:
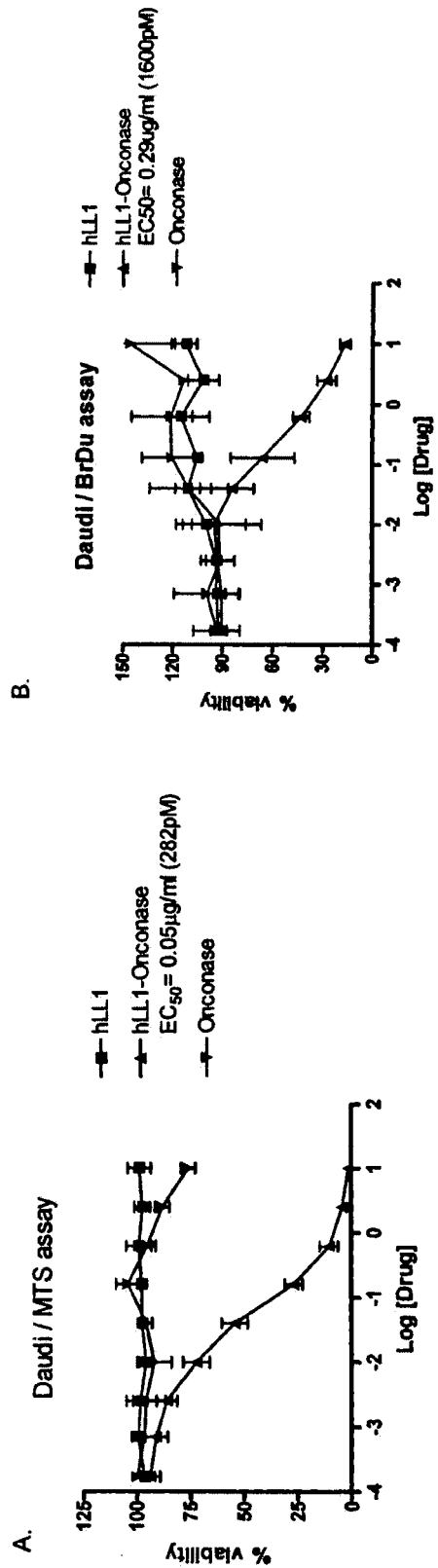
FIG. 8 shows in vitro cytotoxicity of the fusion protein in Daudi cells: (A) Cytotoxicity measured by MTS assay; (B) Cytotoxicity measured by BRdU assay method.
Figure 9:
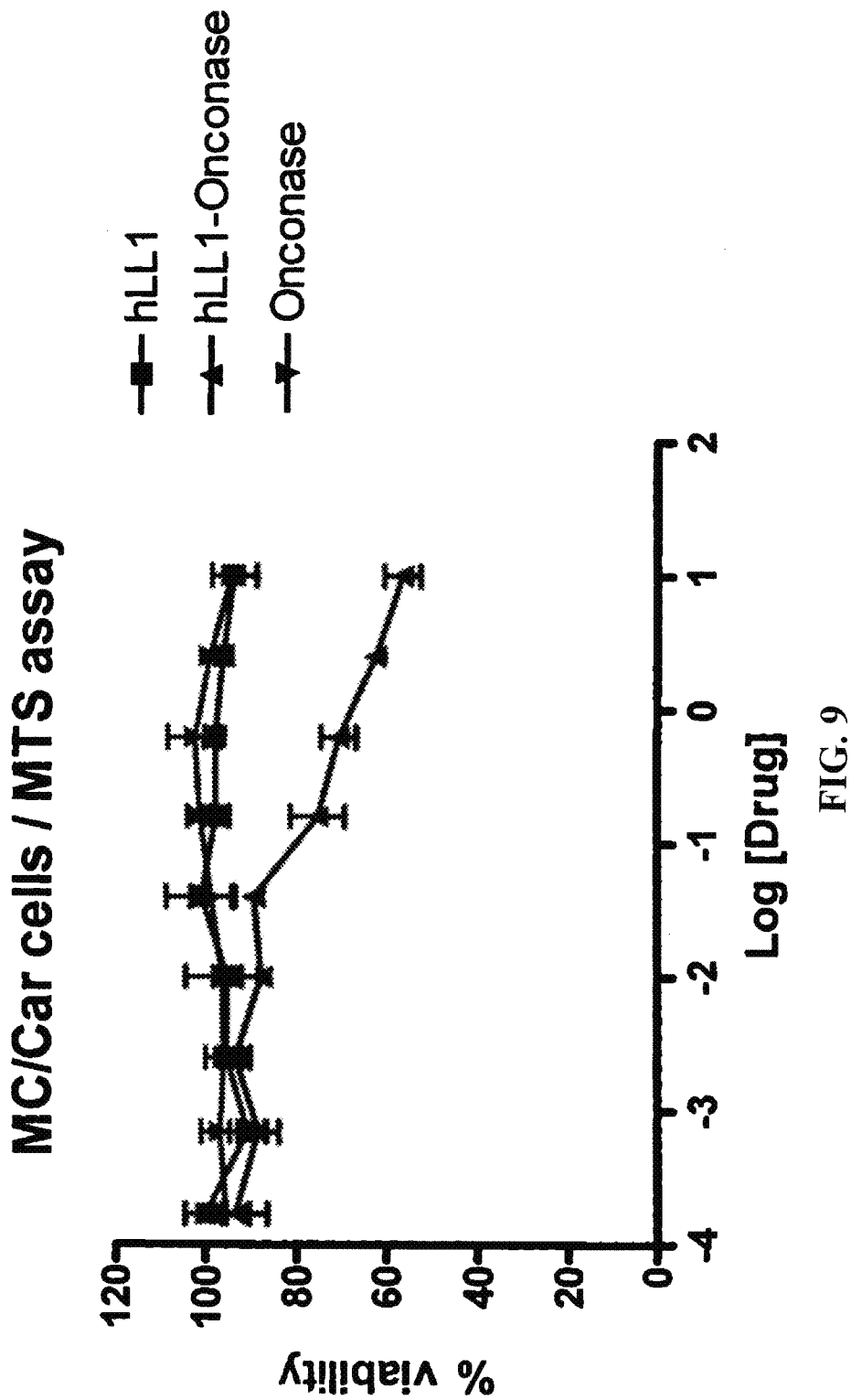
FIG. 9 shows in vitro cytotoxicity of the fusion protein in MC/CAR cells by MTS Assay.

In vitro cytotoxicity was determined in a B-cell lymphoma cell line (Daudi), and a multiple myeloma cell line (MC/CAR). Cells (10,000 in 0.1 ml) were placed in each well of a 96-well plate. After 24 h, free hLL1, free rap or rap-hLL1 (10 μl) were added to appropriate wells, and the cells were incubated for 3 days at 37° C. in incubator. Cell proliferation was determined using the MTS tetrazolium dye reduction assay or the BrDU colorimetric assays. Results are expressed as $EC_{50}$, which was obtained graphically using Prism Pad software. It is evident from FIG. 8-9 that rap-hLL1 was sensitive on both a B-cell lymphoma cell line (Daudi) and a multiple myeloma cell line (MC/CAR). rap-hLL1 was significantly more potent (cytotoxic) on Daudi cells compared to MC/CAR cells, as reflected by the $EC_{50}$ values (FIG. 8 and FIG. 9). For MC/CAR cells, an $EC_{50}$ value was not achieved at the concentrations tested. At the highest concentration (56 nM), cell viability was 57%. hLL1 or free rap, by itself did not demonstrate cytotoxicity in either cell line.

Pharmacokinetics and Biodistribution Methods hLL1 or 2L-Rap-hLL1-γ4P was conjugated to diethylenetriaminepentaacetic acid (DTPA) using 2-(4-isothiocyanatobezyl)DTPA (Macrocyclics, Dallas, Tex.), as described by Sharkey et al., (Int J. Cancer. 1990; 46:79-85). to obtain DTPA-hLL1 or DTPA-2L-Rap-hLL1-γ4P, which was labeled with $^{88}$Y chloride (Los Alamos National Laboratory (Los Alamos, N. Mex.) or $^{111}$In chloride (Perkin Elmer Life Sciences, Boston, Mass.), respectively, for pharmacokinetics and biodistribution studies. Naive female SCID mice (8 weeks old, 18-22 g) were injected intravenously with a mixture of 0.001 mCi $^{88}$Y-DTPA-hLL1 and 0.02 mCi of $^{111}$In-DTPA-2L-Rap-hLL1-γ4P, supplemented with unlabeled DTPA conjugates of hLL1 or 2L-Rap-hLL1-γ4P, so that each animal received a total dose of 10 μg each of hLL1 and 2L-Rap-hLL1-γ4P. At selected times after dosing (1, 2, 4, 16, 48, 72, 168 h), groups of 5 mice were anesthetized and a blood sample was withdrawn by cardiac puncture. Major tissues were removed, weighed, and placed in containers. Blood samples and tissues were counted in a calibrated gamma counter for $^{111}$In (channels 120-480) and $^{88}$Y (channels 600-2000). A crossover curve was generated to correct for the back-scatter of $^{88}$Y energy into the $^{111}$In counting window.

In Vivo Toxicity

Naive SCID or BALB/c mice were injected intravenously with various doses of 2L-Rap-hLL1-γ4P ranging from 25 to 400 μg/mouse, and monitored daily for visible signs of toxicity and body weight loss. The maximum tolerated dose (MTD) was defined as the highest dose at which no death occurred, and body weight loss was <20% of pretreatment animal weight (approximately 20 g). Animals that experienced toxic effects were sacrificed, harvested and subjected to histopathological analysis. In naive SCID mice, a single intravenous dose of 100, 150, 200, 250, 300 or 400 μg of 2L-Rap-hLL1-γ4P resulted in severe weight loss and death of the animals, but all mice survived a dose of 25 or 50 μg (not shown). In BALB/c mice, all mice survived a single intravenous dose of 30 or 50 μg of 2L-Rap-hLL1-γ4P, but not 100 or 200 μg (not shown). In another experiment, a 75 μg-dose of 2L-Rap-hLL1-γ4P was found toxic to SCID mice (data not shown). Therefore, the MTD of 2L-Rap-hLL1-γ4P given as a single bolus injection is between 50 and 75 μg in SCID mice and between 50 and 100 μg in BALB/c mice. Gross pathological examination of the dead or sacrificed mice indicated severe liver and spleen toxicity. The liver was pale in color and the spleen was shriveled and smaller than the usual size. Histopathologic examination revealed hepatic and splenic necrosis. Serum samples of the representative mice had elevated levels of alanine aminotransferase (ALT), asparatate aminotransferase (AST) and total bilirubin, suggesting significant liver toxicity at these high doses.

Data Analysis

For in vitro cytotoxicity studies, dose-response curves were generated from the mean of triplicate determinations, and 50% inhibitory concentration ($IC_{50}$) values were obtained using the GraphPad Prism software (Advanced Graphics Software, Encinitas, Calif.). Pharmacokinetic data were analyzed using the standard algorithms of noncompartmental analysis program WinNonlin, Version 4.1 (Pharsight, Mountain View, Calif.). The program calculates area under the curve (AUC) using the linear trapezoidal rule with a linear interpolation. The elimination rate constant ($k_\beta$) was computed from the terminal half-life ($t_{1/2\ \beta}$) assuming first order kinetics. Survival studies were analyzed using Kaplan-Meier plots (log-rank analysis) with GraphPad Prism software. Differences were considered significant at P<0.05.

Pharmacokinetic and Biodistribution Data

Figure 10:
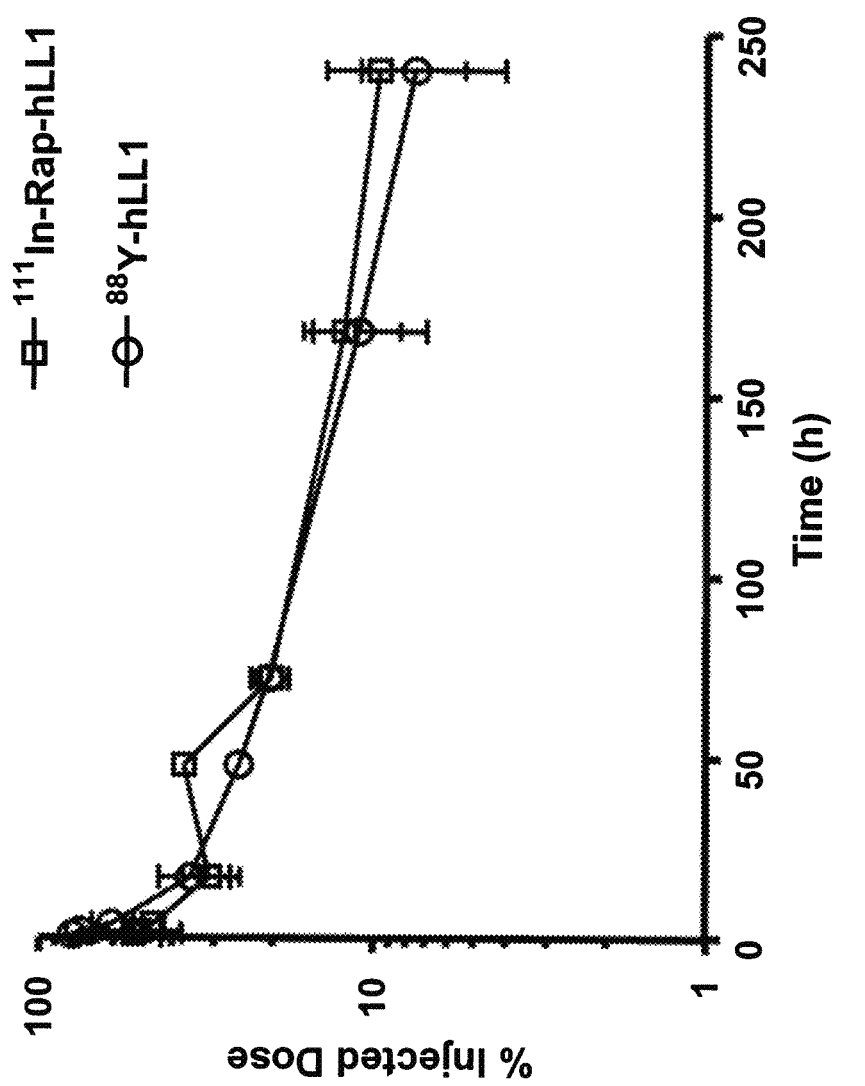
FIG. 10 shows blood clearance of 2L-Rap-hLL1-γ4P in naive SCID mice. Naive SCID mice were co-injected intravenously with $^{88}$Y-DTPA-hLL1 (O) and $^{111}$In-DTPA-2L-Rap-hLL1-γ4P (□). At selected times after dosing, mice were bled by cardiac puncture and a blood sample was counted for radioactivity. Data represent mean±S.D. of injected dose in blood (n=3).

The pharmacokinetics and biodistribution of radiolabeled hLL1 and 2L-Rap-hLL1-γ4P were determined in naive SCID mice. hLL1 and 2L-Rap-hLL1-γ4P were conjugated with DTPA and traced labeled with $^{88}$Y and $^{111}$In, respectively. As shown in FIG. 10, $^{111}$In-labeled 2L-Rap-hLL1-γ4P exhibits similar biphasic clearance from blood as $^{88}$Y-labeled hLL1, characterized by an initial rapid redistribution (α) and a later slower elimination (β) phases. A slightly shorter a half-life was observed for 2L-Rap-hLL1-γ4P (5.1 h), compared with hLL1 (4 h). Data points beyond 5 h were used to compute $t_{1/2\ \beta}$, $k_\beta$,AUC, mean residence time (MRT), apparent volume of distribution ($V_d$), and rate of clearance (CO, and the values of these parameters are shown in Table 2. Tissue uptake of $^{111}$In-labeled 2L-Rap-hLL1-γ4P was similar to that of $^{88}$Y-labeled hLL1 (data not shown).

TABLE 2

Pharmacokinetic parameters for 2L-Rap-hLL1-γ4P and hLL1 in SCID mice using radiolabeled DTPA-conjugates

| Parameter | Unit | $^{88}$Y-DTPA-hLL1 | $^{111}$In-DTPA-2L-Rap-hLL1-γ4P |
|---|---|---|---|
| $T_{1/2,\ \beta}$ | h | 103 | 113 |
| $k_\beta$ | 1/h | 0.0067 | 0.0061 |
| Cl | mL/h | 0.025 | 0.024 |
| Vd | mL | 3.8 | 3.9 |
| MRT | h | 140 | 156 |
| AUC | h * μg/mL | 393 | 418 |

Therapeutic Efficacy in Tumor-Bearing Mice

Therapeutic efficacy in tumor-bearing mice: Female SCID mice (8 weeks old, 18-22 g), 8 to 9 per group, were injected intravenously with 1.5×10$^7$ Daudi cells and received treatments one day later. Mice were examined daily for hind leg paralysis and were weighed weekly. The animals were euthanized when they developed hind leg paralysis or lost 20% of their pretreatment weight. Each set of therapy experiments ended after 180 days.

Figure 11:
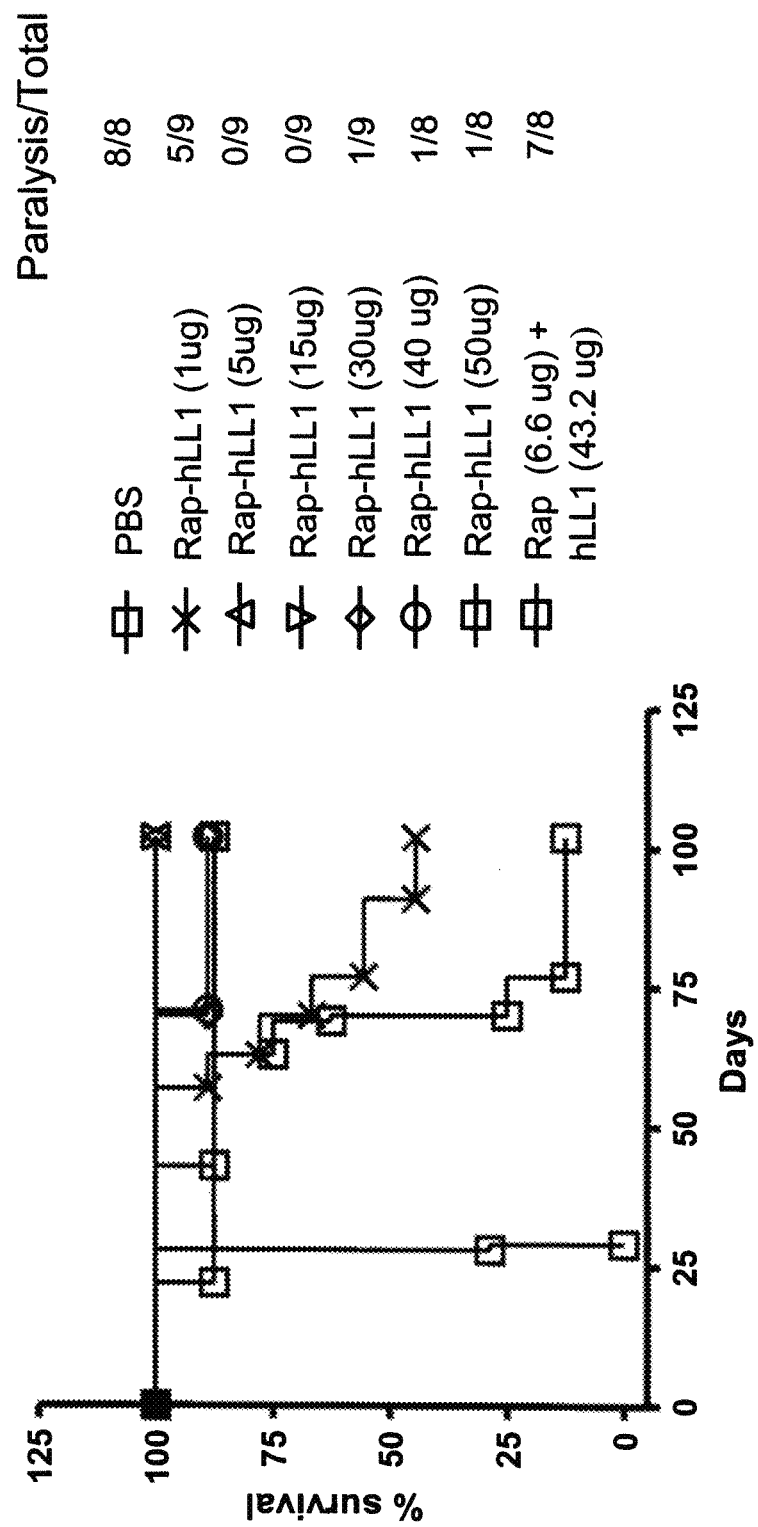
FIG. 11 shows treatment of aggressive minimal Daudi lymphoma with 2L-Rap-hLL1-γ 4P or component proteins. SCID mice (8-10 mice/group) were inoculated intravenously with 1.5×10$^7$ Daudi cells. After 1 day, mice were treated with a single bolus injection of 2L-Rap-hLL1-γ4P at the indicated dosages. Control groups were injected with component proteins equivalent to 50 µg of the immunotoxin or PBS only.
Figure 12:
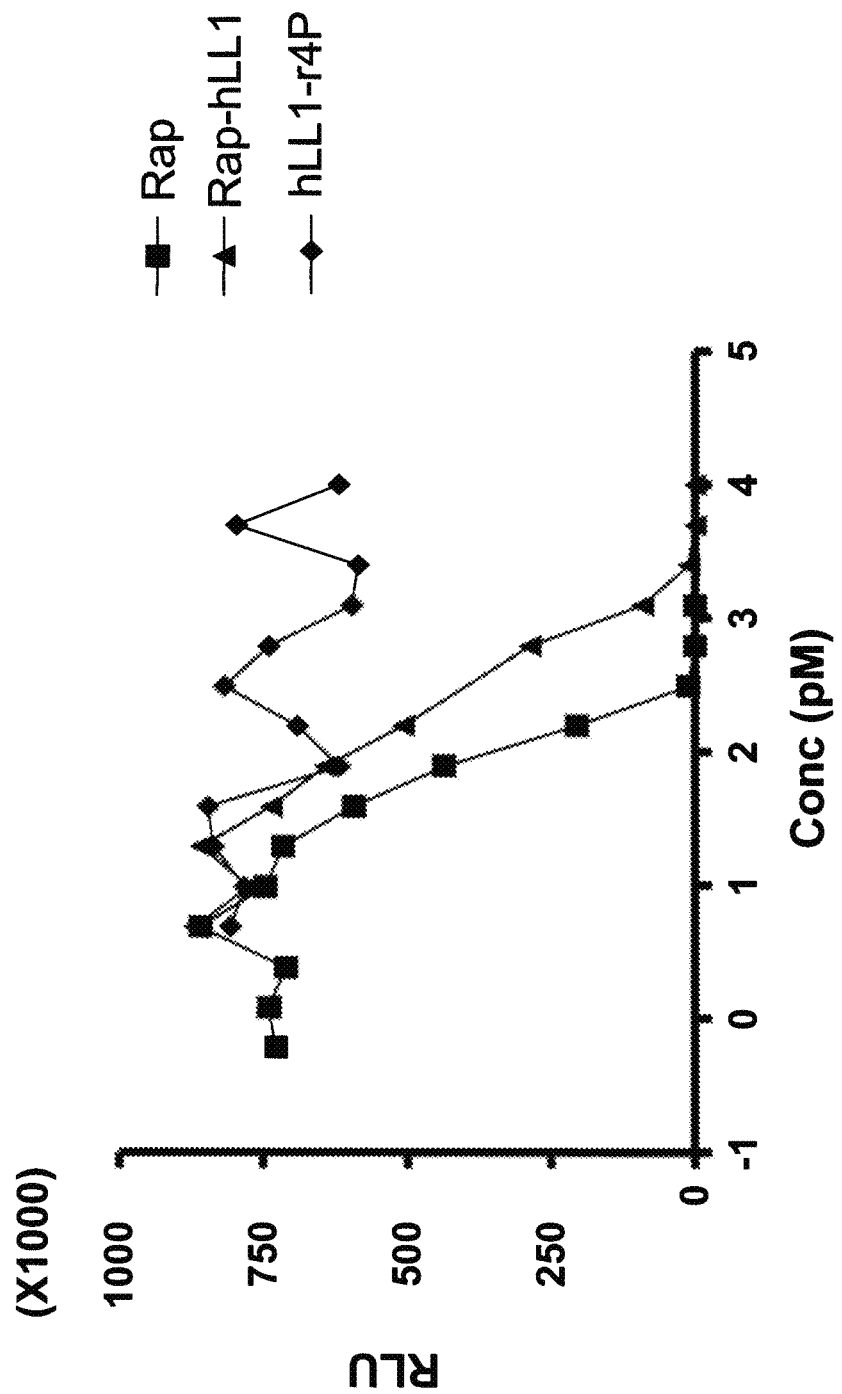
FIG. 12 shows RNase activity as measured by the in vitro transcription/translation assay. Concentrations of rRap (■), 2L-Rap-hLL1-γ4P (▲), and hLL1-γ4P (♦) were plotted against relative luminescence units (RLU).

As shown in FIG. 11, untreated mice (PBS group) all died within 30 days, with a median survival time (MST) of 28 days. The MST of the control group, which received a mixture of hLL1-γ4P (43.2 μg) and Rap (6.6 μg), representing the composition of the component proteins in 50 μg 2L-Rap-hLL1-γ4P, was 70 days (P<0.0001 vs. the PBS group). In contrast, all mice that received a single injection of either 5 or 15 μg of 2L-Rap-hLL1-γ4P were alive for more than 100 days (MST>180 days; P=0.0005 vs. components-treated group), and only one mouse was lost from each group near the end of the study. When the study was terminated after 180 days, 90% of mice receiving a single injection of 5, 15, 30, 40 or 50 μg of 2L-Rap-hLL1-γ4P were cured. It is noteworthy that the MST of mice receiving a single injection of 1 μg was 92 days, compared with 28 days of the untreated group (P<0.0001), representing a 230% increase.

Synthesis of PCR-Amplified DNA Encoding a Cytotoxic RNase

A 139-mer DNA nucleotide, ONCO—N, with the sense strand sequence:

(SEQ ID NO: 88)
```
5'-TGG CTA ACG TTT CAG AAG AAA CAT ATC ACG AAT ACA CGA GAT GTA GAC

TGG GAC AAT ATA ATG TCT ACG AAT CTG TTT CAC TGT AAG GAT AAG AAT ACC

TTT ATA TAC AGT CGG CCA GAG CCT GTA AAG GCT ATC TGT A-3'
``` encoding an N-terminal sequence (46 amino acids) of a recombinant cytotoxic RNase was synthesized by an automated DNA synthesizer and used as the template for PCR-amplification with the primers below.

ONNBACK
(SEQ ID NO: 89)
5'-AAG CTT CAT ATG CAG GAT TGG CTA ACG TTT CAG AAG AAA-3'

ONNFOR
(SEQ ID NO: 90)
5'-CTT ACT CGC GAT AAT GCC TTT ACA GAT AGC CTT TAC AGG CTC TG-3'

The resultant double-stranded PCR product contains cDNA sequence that encodes for 54 amino acid residues of the N-terminal half of the cytotoxic RNase. ONNBACK contains the restriction sites HindIII and NdeI to facilitate subcloning into either a staging vector or for in-frame ligation (NdeI site) into the bacterial expression vector. The NruI site is incorporated in the ONNFOR primer to facilitate in-frame ligation with the cDNA encoding the C-terminal half of the cytotoxic RNase.

Similarly, a 137-mer DNA nucleotide, ONCO—C, with the sense-strand sequence:

(SEQ ID NO: 91)
5'-TGC TGA CTA CTT CCG AGT TCT ATC TGT CCG ATT GCA ATG TGA CTT CAC

GGC CCT GCA AAT ATA AGC TGA AGA AAA GCA CTA ACA AAT TTT GCG TAA CTT

GCG AGA ACC AGG CTC CTG TAC ATT TCG TTG GAG TCG GG-3' encoding the C-terminal sequence (46 amino acids) of the cytotoxic RNase was synthesized and PCR-amplified by the following primers.

ONCBACK
(SEQ ID NO: 92)
5'-ATT ATC GCG AGT AAG AAC GTG CTG ACT ACT TCC GAG TTC TAT-3'

ONCFOR
(SEQ ID NO: 93)
5'-TTA GGA TCC TTA GCA GCT CCC GAC TCC AAC GAA ATG TAC-3'

The final double-stranded PCR product contained a cDNA sequence that encoded 51 amino acids of the rest of the C-terminal half of the cytotoxic RNase. An NruI site allowed in-frame ligation with the N-terminal half of the PCR-amplified DNA incorporated in ONCBACK. A stop codon and BamHI restriction sites for subcloning into staging or expression vectors were included in the ONCFOR sequence.

The PCR-amplified DNA encoding the N- and C-terminal halves of the cytotoxic RNase, after being treated with the appropriate restriction enzymes, were joined at the NruI sites and subcloned into a staging vector, e.g., pBluescript from Stratagene. The ligated sequence encodes a polypeptide of 105 amino acids with an N-terminal Met.

Cloning of LL2 and MN-14 v-region sequences and humanization of LL2 and MN-14

The V-region sequences of hLL2 and hMN-14 have been published. Leung et al., Mol. Immunol., 32:1413 (1995); U.S. Pat. No. 5,874,540. The VK and VH sequences for LL2 and MN-14 were PCR-amplified using published methods and primers. Sequence analysis of the PCR-amplified DNAs indicated that they encoded proteins typical of antibody VK and VH domains. A chimeric antibody constructed based on the PCR-amplified LL2 and MN-14 sequences exhibited immunoreactivity comparable to their parent antibodies, confirming the authenticity of the sequence obtained.

Sequence analysis of the LL2 antibody revealed the presence of a VK-appended N-linked glycosylation site in the framework-1 region. Mutational studies indicated that glycosylation at the VK-appended site was not required to maintain the immunoreactivity of the antibody (not shown). Without the inclusion of the FR-1 glycosylation site, REI framework sequences were used as the scaffold for grafting the light chain CDRs, and EU/NEWM for grafting the heavy chain CDRs of LL2. The immunoreactivity of the humanized LL2 (hLL2) was shown to be comparable to that of murine and chimeric LL2 (not shown). The rate of internalization for LL2 was not affected by chimerization or humanization of the antibody (not shown).

Construction of Gene Encoding Fusion Protein of Humanized LL2 and a Cytotoxic RNase The VH and VK sequences of hLL2 were used as templates to assemble the hLL2-scFv gene by standard PCR procedures. A Met initiation codon at the −1 position was incorporated at the N-terminus of the VL gene, which was linked via a 16 amino acid linker to the VH domain. A tail consisting of six histidyl residues was included at the carboxyl end of the VH chain to facilitate the purification of the fusion protein via metal chelate chromatography.

The immunotoxin fusion protein gene for ranpirnase-hLL2scFv was constructed in a similar fashion by restriction digestion and ligation methods. The cDNA sequence, when expressed, encoded a fusion protein with ranpirnase attached to the N-terminal end of the LL2 VL sequence via a short linker. There are a variety of linkers that can be inserted between the cytotoxic RNase C-terminus and the VL domain N-terminus. A preferable linker is the amino acid sequence TRHRQPRGW (SEQ ID NO: 94) from the C-terminal position 273-281 of *Pseudomonas* exotoxin (PE). This sequence has been shown to be a recognition site for intracellular cleavage of PE into active fragments by subtilisins, with cleavage occurring between the G and W residues of the sequence. Chiron et al., J. Biol. Chem., 269:18167 (1994). Incorporation of this sequence facilitates the release of active cytotoxic RNase after internalization of the fusion immunotoxin. Alternatively, a 13-amino acid residue spacer consisting of amino acid residues 48-60 of fragment B of *Staphylococcal* Protein A, used in the construction of an EDN-scFv fusion, can be used instead to allow for flexible linkage between the cytotoxic RNase and the scFv. Tai et al., Biochemistry, 29:8024 (1990) and Rybak et al., Tumor Targeting, 1:141 (1995).

Construction of Gene Encoding Fusion Protein of Humanized MN-14 and Ranpirnase

MN-14 scFv was produced by PCR amplification of cDNA from humanized MN-14 transfectoma. The linker used for MN-14 scFv was a 15-amino acid linker and the orientation was VL-linker-VH. After continuation of the DNA sequences, the single chain construct was subcloned into a eukaryotic expression vector and transfected into an appropriate mammalian host cell for expression.

Another single chain construct also was made. This was made with the opposite 5'-3' orientation of the heavy and light chains, was assembled in pCANTABE5E (Pharmacia Biotech, Piscataway, N.J.) and expressed in phage. Specific binding of recombinant phage expressing this scFv was demonstrated by ELISA (not shown).

The scFv sequence was used for construction of ranpirnase-MN-14 fusion protein, with ranpirnase attached via linker to the N-terminus of the VL sequence. The DNA fragment encoding ranpirnase was obtained as discussed above. A 23-amino acid linker was used between the ranpirnase sequence and the scFv. Kurucz et al. (1995).

Dock and Lock

Example 3

General Strategy for Production of Modular Fab Subunits

Fab modules may be produced as fusion proteins containing either a DDD or AD sequence. Independent transgenic cell lines are developed for each fusion protein. Once produced, the modules can be purified if desired or maintained in the cell culture supernatant fluid. Following production, any $DDD_2$ module can be combined with any AD module to generate a DNL construct.

The plasmid vector pdHL2 has been used to produce a number of antibodies and antibody-based constructs. See Gillies et al., J Immunol Methods (1989), 125:191-202; Losman et al., Cancer (Phila) (1997), 80:2660-6. The dicistronic mammalian expression vector directs the synthesis of the heavy and light chains of IgG. The vector sequences are mostly identical for many different IgG-pdHL2 constructs, with the only differences existing in the variable domain (VH and VL) sequences. Using molecular biology tools known to those skilled in the art, these IgG expression vectors can be converted into Fab-DDD or Fab-AD expression vectors. To generate Fab-DDD expression vectors, the coding sequences for the hinge, CH2 and CH3 domains of the heavy chain are replaced with a sequence encoding the first 4 residues of the hinge, a 14 residue Gly-Ser linker and the first 44 residues of human RIIα (referred to as DDD1). To generate Fab-AD expression vectors, the sequences for the hinge, CH2 and CH3 domains of IgG are replaced with a sequence encoding the first 4 residues of the hinge, a 15 residue Gly-Ser linker and a 17 residue synthetic AD called AKAP-IS (referred to as AD1), which was generated using bioinformatics and peptide array technology and shown to bind RIIα dimers with a very high affinity (0.4 nM). See Alto, et al. Proc. Natl. Acad. Sci., U.S.A (2003), 100:4445-50.

Two shuttle vectors were designed to facilitate the conversion of IgG-pdHL2 vectors to either Fab-DDD1 or Fab-AD1 expression vectors, as described below.

Preparation of CH1

The CH1 domain was amplified by PCR using the pdHL2 plasmid vector as a template. The left PCR primer consists of the upstream (5') of the CH1 domain and a SacII restriction endonuclease site, which is 5' of the $CH_1$ coding sequence. The right primer consists of the sequence coding for the first 4 residues of the hinge followed by a short linker, with the final two codons comprising a Bam HI restriction site.

```
5' of CH1 Left Primer
                                           (SEQ ID NO: 63)
5'GAACCTCGCGGACAGTTAAG-3'

CH1 + G4S-Bam Right ("G4S" disclosed as SEQ ID
NO: 96)
                                           (SEQ ID NO: 64)
5'GGATCCTCCGCCGCCGCAGCTCTTAGGTTTCTTGTCCACCTTGGTGT

TGCTGG-3'
```

The 410 bp PCR amplimer was cloned into the pGemT PCR cloning vector (Promega, Inc.) and clones were screened for inserts in the T7 (5') orientation.

Construction of $(G_4S)_2DDD1$ ("$(G_4S)_2$" disclosed as SEQ ID NO: 97)

A duplex oligonucleotide, designated $(G_4S)_2DDD1$ ("$(G_4S)_2$" disclosed as SEQ ID NO: 97), was synthesized by Sigma Genosys (Haverhill, UK) to code for the amino acid sequence of DDD1 preceded by 11 residues of the linker peptide, with the first two codons comprising a BamHI restriction site. A stop codon and an EagI restriction site are appended to the 3' end. The encoded polypeptide sequence is shown below.

```
                                           (SEQ ID NO: 65)
GSGGGGSGGGGSHIQIPPGLTELLQGYTVEVLRQQPPDLVEFAVEYFTR

LREARA
```

The two oligonucleotides, designated RIIA1-44 top and RIIA1-44 bottom, that overlap by 30 base pairs on their 3' ends, were synthesized (Sigma Genosys) and combined to comprise the central 154 base pairs of the 174 bp DDD1 sequence. The oligonucleotides were annealed and subjected to a primer extension reaction with Taq polymerase.

```
RIIA1-44 top
                                           (SEQ ID NO: 66)
5'GTGGCGGGTCTGGCGGAGGTGGCAGCCACATCCAGATCCCGCCGGGG

CTCACGGAGCTGCTGCAGGGCTACACGGTGGAGGTGCTGCGACAG-3'

RIIA1-44 bottom
                                           (SEQ ID NO: 67)
5'GCGCGAGCTTCTCTCAGGCGGGTGAAGTACTCCACTGCGAATTCGAC

GAGGTCAGGCGGCTGCTGTCGCAGCACCTCCACCGTGTAGCCCTG-3'
```

Following primer extension, the duplex was amplified by PCR using the following primers:

```
G4S Bam-Left ("G4S" disclosed as SEQ ID NO: 96)
                                         (SEQ ID NO: 68)
5'-GGATCCGGAGGTGGCGGGTCTGGCGGAGGT-3'

1-44 stop Eag Right
                                         (SEQ ID NO: 69)
5'-CGGCCGTCAAGCGCGAGCTTCTCTCAGGCG-3'
```

This amplimer was cloned into pGemT and screened for inserts in the T7 (5') orientation.

Construction of (G$_4$S)$_2$-AD1 ("(G$_4$S)$_2$" Disclosed as SEQ ID NO: 97)

A duplex oligonucleotide, designated (G$_4$5)$_2$-AD1 ("(G$_4$5)$_2$" disclosed as SEQ ID NO: 97), was synthesized (Sigma Genosys) to code for the amino acid sequence of AD1 preceded by 11 residues of the linker peptide with the first two codons comprising a BamHI restriction site. A stop codon and an EagI restriction site are appended to the 3' end. The encoded polypeptide sequence is shown below.

```
                                         (SEQ ID NO: 70)
    GSGGGGSGGGGSQIEYLAKQIVDNAIQQA
```

Two complimentary overlapping oligonucleotides, designated AKAP-IS Top and AKAP-IS Bottom, were synthesized.

```
AKAP-IS Top
                                         (SEQ ID NO: 71)
5'GGATCCGGAGGTGGCGGGTCTGGCGGAGGTGGCAGCCAGATCGAGTA

CCTGGCCAAGCAGATCGTGGACAACGCCATCCAGCAGGCCTGACGGCC

G-3'

AKAP-IS Bottom
                                         (SEQ ID NO: 72)
5'CGGCCGTCAGGCCTGCTGGATGGCGTTGTCCACGATCTGCTTGGCCA

GGTACTCGATCTGGCTGCCACCTCCGCCAGACCCGCCACCTCCGGATC

C-3'
```

The duplex was amplified by PCR using the following primers:

```
G4S Bam-Left ("G4S" disclosed as SEQ ID NO: 96)
                                         (SEQ ID NO: 73)
5'-GGATCCGGAGGTGGCGGGTCTGGCGGAGGT-3'

AKAP-IS stop Eag Right
                                         (SEQ ID NO: 74)
5'-CGGCCGTCAGGCCTGCTGGATG-3'
```

This amplimer was cloned into the pGemT vector and screened for inserts in the T7 (5') orientation.

Ligating DDD1 with CH1

A 190 bp fragment encoding the DDD1 sequence was excised from pGemT with BamHI and NotI restriction enzymes and then ligated into the same sites in CH$_1$-pGemT to generate the shuttle vector CH$_1$-DDD1-pGemT.

Ligating AD1 with CH1

A 110 bp fragment containing the AD1 sequence was excised from pGemT with BamHI and NotI and then ligated into the same sites in CH1-pGemT to generate the shuttle vector CH1-AD1-pGemT.

Cloning CH$_1$-DDD1 or CH1-AD1 into pdHL2-Based Vectors

With this modular design either CH1-DDD1 or CH1-AD1 can be incorporated into any IgG construct in the pdHL2 vector. The entire heavy chain constant domain is replaced with one of the above constructs by removing the SacII/EagI restriction fragment (CH1-CH3) from pdHL2 and replacing it with the SacII/EagI fragment of CH1-DDD1 or CH1-AD1, which is excised from the respective pGemT shuttle vector.

N-Terminal DDD Domains

The location of the DDD or AD is not restricted to the carboxyl terminal end of CH1. A construct was engineered in which the DDD1 sequence was attached to the amino terminal end of the VH domain.

Example 4

DNL Expression Vectors

Construction of h679-Fd-AD1-pdHL2 h679-Fd-AD1-pdHL2 is an expression vector for production of h679 Fab with AD1 coupled to the carboxyl terminal end of the CH1 domain of the Fd via a flexible Gly/Ser peptide spacer composed of 14 amino acid residues. A pdHL2-based vector containing the variable domains of h679 was converted to h679-Fd-AD1-pdHL2 by replacement of the SacII/EagI fragment with the CH1-AD1 fragment, which was excised from the CH1-AD1-SV3 shuttle vector with SacI and EagI.

Construction of C-DDD1-Fd-hMN-14-pdHL2

C-DDD1-Fd-hMN-14-pdHL2 is an expression vector for production of fusion protein C-DDD1-Fab-hMN-14, in which DDD1 is linked to hMN-14 Fab at the carboxyl terminus of CH1 via a flexible peptide spacer. The plasmid vector hMN14(I)-pdHL2, which has been used to produce hMN-14 IgG, was converted to C-DDD1-Fd-hMN-14-pdHL2 by digestion with SacII and EagI restriction endonucleases to remove the CH1-CH3 domains and insertion of the CH$_1$-DDD1 fragment, which was excised from the CH$_1$-DDD1-SV3 shuttle vector with SacII and EagI.

Construction of N-DDD1-Fd-hMN-14-pdHL2

N-DDD1-Fd-hMN-14-pdHL2 is an expression vector for production of a stable dimer that comprises two copies of a fusion protein N-DDD1-Fab-hMN-14, in which DDD1 is linked to hMN-14 Fab at the amino terminus of VH via a flexible peptide spacer. The expression vector was engineered as follows. The DDD1 domain was amplified by PCR using the two primers shown below.

```
DDD1 Nco Left
                                         (SEQ ID NO: 75)
5' CCATGGGCAGCCACATCCAGATCCCGCC-3'

DDD1-G$_4$S Bam Right ("G$_4$S" disclosed as SEQ ID
NO: 96)
                                         (SEQ ID NO: 76)
5'GGATCCGCCACCTCCAGATCCTCCGCCGCCAGCGCGAGCTTCTCTCA

GGCGGGTG-3'
```

As a result of the PCR, an NcoI restriction site and the coding sequence for part of the linker containing a BamHI restriction were appended to the 5' and 3' ends, respectively. The 170 bp PCR amplimer was cloned into the pGemT vector and clones were screened for inserts in the T7 (5') orientation. The 194 bp insert was excised from the pGemT vector with NcoI and SalI restriction enzymes and cloned into the SV3 shuttle vector, which was prepared by digestion with those same enzymes, to generate the intermediate vector DDD1-SV3.

The hMN-14 Fd sequence was amplified by PCR using the oligonucleotide primers shown below.

hMN-14VH left G4S Bam ("G4S" disclosed as SEQ ID NO: 96)
(SEQ ID NO: 77)
5'-GGATCCGGCGGAGGTGGCTCTGAGGTCCAACTGGTGGAGAGCGG-3'

CH1-C stop Eag
(SEQ ID NO: 78)
5'- CGGCCGTCAGCAGCTCTTAGGTTTCTTGTC -3'

As a result of the PCR, a BamHI restriction site and the coding sequence for part of the linker were appended to the 5' end of the amplimer. A stop codon and EagI restriction site was appended to the 3' end. The 1043 bp amplimer was cloned into pGemT. The hMN-14-Fd insert was excised from pGemT with BamHI and EagI restriction enzymes and then ligated with DDD1-SV3 vector, which was prepared by digestion with those same enzymes, to generate the construct N-DDD1-hMN-14Fd-SV3.

The N-DDD1-hMN-14 Fd sequence was excised with XhoI and EagI restriction enzymes and the 1.28 kb insert fragment was ligated with a vector fragment that was prepared by digestion of C-hMN-14-pdHL2 with those same enzymes. The final expression vector is N-DDD1-Fd-hMN-14-pDHL2.

Example 5

Production and Purification of h679-Fab-AD1

The 679 antibody binds to an HSG target antigen and may be purified by affinity chromatography. The h679-Fd-AD1-pdHL2 vector was linearized by digestion with Sal I restriction endonuclease and transfected into Sp/EEE myeloma cells by electroporation. The di-cistronic expression vector directs the synthesis and secretion of both h679 kappa light chain and h679 Fd-AD1, which combine to form h679 Fab-AD1. Following electroporation, the cells were plated in 96-well tissue culture plates and transfectant clones were selected with 0.05 μM methotrexate (MTX). Clones were screened for protein expression by ELISA using microtitre plates coated with a BSA-IMP-260 (HSG) conjugate and detection with HRP-conjugated goat anti-human Fab. BIAcore analysis using an HSG (IMP-239) sensorchip was used to determine the productivity by measuring the initial slope obtained from injection of diluted media samples. The highest producing clone had an initial productivity of approximately 30 mg/L. A total of 230 mg of h679-Fab-AD1 was purified from 4.5 liters of roller bottle culture by single-step IMP-291 affinity chromatography. Culture media was concentrated approximately 10-fold by ultrafiltration before loading onto an IMP-291-affigel column. The column was washed to baseline with PBS and h679-Fab-AD1 was eluted with 1 M imidazole, 1 mM EDTA, 0.1 M NaAc, pH 4.5. SE-HPLC analysis of the eluate showed a single sharp peak with a retention time (9.63 min) consistent with a 50 kDa protein (not shown). Only two bands, which represent the polypeptide constituents of h679-AD1, were evident by reducing SDS-PAGE analysis (not shown).

Example 6

Production and Purification of
N-DDD1-Fab-hMN-14 and C-DDD1-Fab-hMN-14

The C-DDD1-Fd-hMN-14-pdHL2 and N-DDD1-Fd-hMN-14-pdHL2 vectors were transfected into Sp2/0-derived myeloma cells by electroporation. C-DDD1-Fd-hMN-14-pdHL2 is a di-cistronic expression vector, which directs the synthesis and secretion of both hMN-14 kappa light chain and hMN-14 Fd-DDD1, which combine to form C-DDD1-hMN-14 Fab. N-DDD1-hMN-14-pdHL2 is a di-cistronic expression vector, which directs the synthesis and secretion of both hMN-14 kappa light chain and N-DDD1-Fd-hMN-14, which combine to form N-DDD1-Fab-hMN-14. Each fusion protein forms a stable homodimer via the interaction of the DDD1 domain.

Following electroporation, the cells were plated in 96-well tissue culture plates and transfectant clones were selected with 0.05 μM methotrexate (MTX). Clones were screened for protein expression by ELISA using microtitre plates coated with WI2 (a rat anti-id monoclonal antibody to hMN-14) and detection with HRP-conjugated goat anti-human Fab. The initial productivity of the highest producing C-DDD1-Fab-hMN14 Fab and N-DDD1-Fab-hMN14 Fab clones was 60 mg/L and 6 mg/L, respectively.

Affinity Purification of N-DDD1-hMN-14 and C-DDD1-hMN-14 with AD1-Affigel

The DDD/AD interaction was utilized to affinity purified DDD1-containing constructs. AD1-C is a peptide that was made synthetically consisting of the AD1 sequence and a carboxyl terminal cysteine residue, which was used to couple the peptide to Affigel following reaction of the sulfhydryl group with chloroacetic anhydride. DDD-containing $a_2$ structures specifically bind to the AD1-C-Affigel resin at neutral pH and can be eluted at low pH (e.g., pH 2.5).

A total of 81 mg of C-DDD1-Fab-hMN-14 was purified from 1.2 liters of roller bottle culture by single-step AD1-C affinity chromatography. Culture media was concentrated approximately 10-fold by ultrafiltration before loading onto an AD1-C-affigel column. The column was washed to baseline with PBS and C-DDD1-Fab-hMN-14 was eluted with 0.1 M Glycine, pH 2.5. SE-HPLC analysis of the eluate showed a single protein peak with a retention time (8.7 min) consistent with a 107 kDa protein (not shown). The purity was also confirmed by reducing SDS-PAGE, showing only two bands of molecular size expected for the two polypeptide constituents of C-DDD1-Fab-hMN-14 (not shown).

A total of 10 mg of N-DDD1-hMN-14 was purified from 1.2 liters of roller bottle culture by single-step AD1-C affinity chromatography as described above. SE-HPLC analysis of the eluate showed a single protein peak with a retention time (8.77 min) similar to C-DDD1-Fab-hMN-14 and consistent with a 107 kDa protein (not shown). Reducing SDS-PAGE showed only two bands attributed to the polypeptide constituents of N-DDD1-Fab-hMN-14 (not shown).

The binding activity of C-DDD1-Fab-hMN-14 was determined by SE-HPLC analysis of samples in which the test article was mixed with various amounts of WI2. A sample prepared by mixing WI2 Fab and C-DDD1-Fab-hMN-14 at a molar ratio of 0.75:1 showed three peaks, which were attributed to unbound C-DDD1-Fab-hMN14 (8.71 min), C-DDD1-Fab-hMN-14 bound to one WI2 Fab (7.95 min), and C-DDD1-Fab-hMN14 bound to two WI2 Fabs (7.37 min) (not shown). When a sample containing WI2 Fab and C-DDD1-Fab-hMN-14 at a molar ratio of 4 was analyzed, only a single peak at 7.36 minutes was observed (not shown). These results demonstrate that hMN14-Fab-DDD1 is dimeric and has two active binding sites. Very similar results were obtained when this experiment was repeated with N-DDD1-Fab-hMN-14.

A competitive ELISA demonstrated that both C-DDD1-Fab-hMN-14 and N-DDD1-Fab-hMN-14 bind to CEA with an avidity similar to hMN-14 IgG, and significantly stronger than monovalent hMN-14 Fab (not shown). ELISA plates were coated with a fusion protein containing the epitope (A3B3) of CEA for which hMN-14 is specific.

Example 7

Formation of $a_2b$ Complexes

Evidence for the formation of an $a_2b$ complex was provided by SE-HPLC analysis of a mixture containing C-DDD1-Fab-hMN-14 (as $a_2$) and h679-Fab-AD1 (as b) in an equal molar amount. When such a sample was analyzed, a single peak was observed having a retention time of 8.40 minutes, which is consistent with the formation of a new protein that is larger than either h679-Fab-AD1 (9.55 min) or C-DDD1-Fab-hMN-14 (8.73 min) alone (not shown). The upfield shift was not observed when hMN-14 F(ab')$_2$ was mixed with h679-Fab-AD1 or C-DDD1-Fab-hMN-14 was mixed with 679-Fab-NEM, demonstrating that the interaction is mediated specifically via the DDD1 and AD1 domains. Very similar results were obtained using h679-Fab-AD1 and N-DDD1-Fab-hMN-14 (not shown).

BIAcore was used to further demonstrate and characterize the specific interaction between the DD 1 and AD1 fusion proteins. The experiments were performed by first allowing either h679-Fab-AD1 or 679-Fab-NEM to bind to the surface of a high density HSG-coupled (IMP239) sensorchip, followed by a subsequent injection of C— DDD1-Fab-hMN-14 or hMN-14 F(ab')$_2$. As expected, only the combination of h679-Fab-AD1 and C-DDD1-Fab-hMN-14 resulted in a further increase in response units when the latter was injected (not shown). Similar results were obtained using N-DDD1-Fab-hMN-14 and h679-Fab-AD1 (not shown).

Equilibrium SE-HPLC experiments were carried out to determine the binding affinity of the specific interaction between AD1 and DDD1 present in the respective fusion proteins. The dissociation constants ($K_d$) for the binding of h679-Fab-AD1 with C-DDD1-Fab-hMN-14, N-DDD1-hMN-14 and a commercial sample of recombinant human RIIα were found to be 15 nM, 8 nM and 30 nM, respectively.

Example 8

Affinity Purification of Either DDD or AD Fusion Proteins

Universal affinity purification systems can be developed by production of DDD or AD proteins, which have lower affinity docking. The DDD formed by RIα dimers binds AKAP-IS (AD1) with a 500-fold weaker affinity (225 nM) compared to RIIa. Thus, RIa dimers formed from the first 44 amino acid resides can be produced and coupled to a resin to make an affinity matrix for purification of any AD1-containing fusion protein.

Many lower affinity (0.1 μM) AKAP anchoring domains exist in nature. If necessary, highly predicable amino acid substitutions can be introduced to further lower the binding affinity. A low affinity AD can be produced either synthetically or biologically and coupled to resin for use in affinity purification of any DDD1 fusion protein.

Example 9

Vectors for Producing Disulfide Stabilized Structures

N-DDD2-Fd-hMN-14-pdHL2

N-DDD2-hMN-14-pdHL2 is an expression vector for production of N-DDD2-Fab-hMN-14, which possesses a dimerization and docking domain sequence of DDD2 appended to the amino terminus of the Fd. The DDD2 is coupled to the $V_H$ domain via a 15 amino acid residue Gly/Ser peptide linker. DDD2 has a cysteine residue preceding the dimerization and docking sequences, which are identical to those of DDD1.

The expression vector was engineered as follows. Two overlapping, complimentary oligonucleotides (DDD2 Top and DDD2 Bottom), which comprise residues 1-13 of DDD2, were made synthetically. The oligonucleotides were annealed and phosphorylated with T4 polynucleotide kinase (PNK), resulting in overhangs on the 5' and 3' ends that are compatible for ligation with DNA digested with the restriction endonucleases NcoI and PstI, respectively.

```
DDD2 Top
                                        (SEQ ID NO: 79)
5'CATGTGCGGCCACATCCAGATCCCGCCGGGGCTCACGGAGCTGCTGC
A-3'

DDD2 Bottom
                                        (SEQ ID NO: 80)
5'GCAGCTCCGTGAGCCCCGGCGGGATCTGGATGTGGCCGCA-3'
```

The duplex DNA was ligated with a vector fragment, DDD1-hMN14 Fd-SV3 that was prepared by digestion with NcoI and PstI, to generate the intermediate construct DDD2-hMN14 Fd-SV3. A 1.28 kb insert fragment, which contained the coding sequence for DDD2-hMN14 Fd, was excised from the intermediate construct with XhoI and EagI restriction endonucleases and ligated with hMN14-pdHL2 vector DNA that was prepared by digestion with those same enzymes. The final expression vector is N-DDD2-Fd-hMN-14-pdHL2.

C-DDD2-Fd-hMN-14-pdHL2

C-DDD2-Fd-hMN-14-pdHL2 is an expression vector for production of C-DDD2-Fab-hMN-14, which possesses a dimerization and docking domain sequence of DDD2 appended to the carboxyl terminus of the Fd via a 14 amino acid residue Gly/Ser peptide linker. The expression vector was engineered as follows. Two overlapping, complimentary oligonucleotides, which comprise the coding sequence for part of the linker peptide (GGGGSGGGCG, SEQ ID NO:81) and residues 1-13 of DDD2, were made synthetically. The oligonucleotides were annealed and phosphorylated with T4 PNK, resulting in overhangs on the 5' and 3' ends that are compatible for ligation with DNA digested with the restriction endonucleases BamHI and PstI, respectively.

```
G4S-DDD2 top ("G4S" disclosed as SEQ ID NO: 96)
                                        (SEQ ID NO: 82)
5'GATCCGGAGGTGGCGGGTCTGGCGGAGGTTGCGGCCACATCCAGATC

CCGCCGGGGCTCACGGAGCTGCTGCA-3'
```

-continued

G4S-DDD2 bottom ("G4S" disclosed as SEQ ID NO: 96)

(SEQ ID NO: 83)
5'GCAGCTCCGTGAGCCCCGGCGGGATCTGGATGTGGCCGCAACCTCCG

CCAGACCCGCCACCTCCG-3'

The duplex DNA was ligated with the shuttle vector $CH_1$-DDD1-pGemT, which was prepared by digestion with BamHI and PstI, to generate the shuttle vector CH1-DDD2-pGemT. A 507 bp fragment was excised from CH1-DDD2-pGemT with SacII and EagI and ligated with the IgG expression vector hMN14(I)-pdHL2, which was prepared by digestion with SacII and EagI. The final expression construct is C-DDD2-Fd-hMN-14-pdHL2.

h679-Fd-AD2-pdHL2 h679-Fd-AD2-pdHL2 is an expression vector for the production of h679-Fab-AD2, which possesses an anchor domain sequence of AD2 appended to the carboxyl terminal end of the CH1 domain via a 14 amino acid residue Gly/Ser peptide linker. AD2 has one cysteine residue preceding and another one following the anchor domain sequence of AD1.

The expression vector was engineered as follows. Two overlapping, complimentary oligonucleotides (AD2 Top and AD2 Bottom), which comprise the coding sequence for AD2 and part of the linker sequence, were made synthetically. The oligonucleotides were annealed and phosphorylated with T4 PNK, resulting in overhangs on the 5' and 3' ends that are compatible for ligation with DNA digested with the restriction endonucleases BamHI and SpeI, respectively.

AD2 Top (SEQ ID NO: 84)
5'GATCCGGAGGTGGCGGGTCTGGCGGATGTGGCCAGATCGAGTACCTG

GCCAAGCAGATCGTGGACAACGCCATCCAGCAGGCCGGCTGCTGAA-3'

AD2 Bottom (SEQ ID NO: 85)
5'TTCAGCAGCCGGCCTGCTGGATGGCGTTGTCCACGATCTGCTTGGCC

AGGTACTCGATCTGGCCACATCCGCCAGACCCGCCACCTCCG-3'

The duplex DNA was ligated into the shuttle vector CH1-AD1-pGemT, which was prepared by digestion with BamHI and SpeI, to generate the shuttle vector CH1-AD2-pGemT. A 429 base pair fragment containing CH1 and AD2 coding sequences was excised from the shuttle vector with SacII and EagI restriction enzymes and ligated into h679-pdHL2 vector that prepared by digestion with those same enzymes. The final expression vector is h679-Fd-AD2-pdHL2.

Example 10

Generation of TF1

A large scale preparation of a DNL construct, referred to as TF1, was carried out as follows. N-DDD2-Fab-hMN-14 (Protein L-purified) and h679-Fab-AD2 (IMP-291-purified) were first mixed in roughly stoichiometric concentrations in 1 mM EDTA, PBS, pH 7.4. Before the addition of TCEP, SE-HPLC did not show any evidence of $a_2b$ formation (not shown). Instead there were peaks representing $a_4$ (7.97 min; 200 kDa), $a_2$ (8.91 min; 100 kDa) and B (10.01 min; 50 kDa). Addition of 5 mM TCEP rapidly resulted in the formation of the $a_2b$ complex as demonstrated by a new peak at 8.43 min, consistent with a 150 kDa protein (not shown). Apparently there was excess B in this experiment as a peak attributed to h679-Fab-AD2 (9.72 min) was still evident yet no apparent peak corresponding to either $a_2$ or $a_4$ was observed. After reduction for one hour, the TCEP was removed by overnight dialysis against several changes of PBS. The resulting solution was brought to 10% DMSO and held overnight at room temperature.

When analyzed by SE-HPLC, the peak representing $a_2b$ appeared to be sharper with a slight reduction of the retention time by 0.1 min to 8.31 min (not shown), which, based on our previous findings, indicates an increase in binding affinity. The complex was further purified by IMP-291 affinity chromatography to remove the kappa chain contaminants. As expected, the excess h679-AD2 was co-purified and later removed by preparative SE-HPLC (not shown).

TF1 is a highly stable complex. When TF1 was tested for binding to an HSG (IMP-239) sensorchip, there was no apparent decrease of the observed response at the end of sample injection. In contrast, when a solution containing an equimolar mixture of both C-DDD1-Fab-hMN-14 and h679-Fab-AD1 was tested under similar conditions, the observed increase in response units was accompanied by a detectable drop during and immediately after sample injection, indicating that the initially formed $a_2b$ structure was unstable. Moreover, whereas subsequent injection of WI2 gave a substantial increase in response units for TF1, no increase was evident for the C-DDD1/AD1 mixture.

The additional increase of response units resulting from the binding of WI2 to TF1 immobilized on the sensorchip corresponds to two fully functional binding sites, each contributed by one subunit of N-DDD2-Fab-hMN-14. This was confirmed by the ability of TF1 to bind two Fab fragments of WI2 (not shown). When a mixture containing h679-AD2 and N-DDD1-hMN14, which had been reduced and oxidized exactly as TF1, was analyzed by BIAcore, there was little additional binding of WI2 (not shown), indicating that a disulfide-stabilized $a_2b$ complex such as TF1 could only form through the interaction of DDD2 and AD2.

Two improvements to the process were implemented to reduce the time and efficiency of the process. First, a slight molar excess of N-DDD2-Fab-hMN-14 present as a mixture of $a_4/a_2$ structures was used to react with h679-Fab-AD2 so that no free h679-Fab-AD2 remained and any $a_4/a_2$ structures not tethered to h679-Fab-AD2, as well as light chains, would be removed by IMP-291 affinity chromatography. Second, hydrophobic interaction chromatography (HIC) has replaced dialysis or diafiltration as a means to remove TCEP following reduction, which would not only shorten the process time but also add a potential viral removing step. N-DDD2-Fab-hMN-14 and 679-Fab-AD2 were mixed and reduced with 5 mM TCEP for 1 hour at room temperature. The solution was brought to 0.75 M ammonium sulfate and then loaded onto a Butyl FF HIC column. The column was washed with 0.75 M ammonium sulfate, 5 mM EDTA, PBS to remove TCEP. The reduced proteins were eluted from the HIC column with PBS and brought to 10% DMSO. Following incubation at room temperature overnight, highly purified TF1 was isolated by IMP-291 affinity chromatography (not shown). No additional purification steps, such as gel filtration, were required.

Example 11

Generation of TF2

Following the successful creation of TF1, an analog designated TF2 was obtained by reacting C-DDD2-FabhMN-14 with h679-Fab-AD2. A pilot batch of TF2 was generated with >90% yield as follows. Protein L-purified C-DDD2-Fab-hMN-14 (200 mg) was mixed with h679-Fab-AD2 (60 mg) at a 1.4:1 molar ratio. The total protein concentration was 1.5 mg/ml in PBS containing 1 mM EDTA. Subsequent steps involving TCEP reduction, HIC chromatography, DMSO oxidation, and IMP-291 affinity chromatography were the same as described for TF1. Before the addition of TCEP, SE-HPLC did not show any evidence of $a_2b$ formation (not shown). Instead there were peaks corresponding to $a_4$ (8.40 min; 215 kDa), $a_2$ (9.32 min; 107 kDa) and b (10.33 min; 50 kDa). Addition of 5 mM TCEP rapidly resulted in the formation of $a_2b$ complex as demonstrated by a new peak at 8.77 min (not shown), consistent with a 157 kDa protein expected for the binary structure. TF2 was purified to near homogeneity by IMP-291 affinity chromatography (not shown). SE-HPLC analysis of the IMP-291 unbound fraction demonstrated the removal of $a_4$, $a_2$ and free kappa chains from the product (not shown).

The functionality of TF2 was determined by BIACORE as described for TF1. TF2, C-DDD1-hMN-14+ h679-AD1 (used as a control sample of noncovalent $a_2b$ complex), or C-DDD2-hMN-14+ h679-AD2 (used as a control sample of unreduced $a_2$ and b components) were diluted to 1 μg/ml (total protein) and pass over a sensorchip immobilized with HSG. The response for TF2 was approximately two-fold that of the two control samples, indicating that only the h679-Fab-AD component in the control samples would bind to and remains on the sensorchip. Subsequent WI2 IgG injections demonstrated that only TF2 had a DDD-Fab-hMN-14 component that was tightly associated with h679-Fab-AD as indicated by an additional signal response. The additional increase of response units resulting from the binding of WI2 to TF2 immobilized on the sensorchip also corresponds to two fully functional binding sites, each contributed by one subunit of C-DDD2-Fab-hMN-14. This was confirmed by the ability of TF2 to bind two Fab fragments of WI2 (not shown).

The relative CEA-binding avidity of TF2 was determined by competitive ELISA. Plates were coated (0.5 μg/well) with a fusion protein containing the A3B3 domain of CEA, which is recognized by hMN-14. Serial dilutions of TF1, TF2 and hMN-14 IgG were made in quadruplicate and incubated in wells containing HRP-conjugated hMN-14 IgG (1 nM). The data indicate that TF2 binds CEA with an avidity that is at least equivalent to that of IgG and two-fold stronger than TF1 (not shown).

Example 12

Serum Stability of TF1 and TF2

TF1 and TF2 were designed to be stably tethered structures that could be used in vivo where extensive dilution in blood and tissues would occur. The stability of TF2 in human sera was assessed using BIACORE. TF2 was diluted to 0.1 mg/ml in fresh human serum, which was pooled from four donors, and incubated at 37° C. under 5% $CO_2$ for seven days. Daily samples were diluted 1:25 and then analyzed by BIACORE using an IMP-239 HSG sensorchip. An injection of WI2 IgG was used to quantify the amount of intact and fully active TF2. Serum samples were compared to control samples that were diluted directly from the stock. TF2 is highly stable in serum, retaining 98% of its bispecific binding activity after 7 days (not shown). Similar results were obtained for TF1 in either human or mouse serum (not shown).

Example 13

Creation of C—H-AD2-IgG-pdHL2 Expression Vectors

The pdHL2 mammalian expression vector has been used to mediate the expression of many recombinant IgGs (Qu et al., Methods 2005, 36:84-95). A plasmid shuttle vector was produced to facilitate the conversion of any IgG-pdHL2 vector into a C—H-AD2-IgG-pdHL2 vector. The gene for the Fc (CH2 and CH3 domains) was amplified using the pdHL2 vector as a template and the oligonucleotides Fc BglII Left and Fc Bam-EcoRI Right as primers.

```
Fc BglII Left
                                    (SEQ ID NO: 86)
5'-AGATCTGGCGCACCTGAACTCCTG-3'

Fc Bam-EcoRI Right
                                    (SEQ ID NO: 87)
5'-GAATTCGGATCCTTTACCCGGAGACAGGGAGAG-3'
```

The amplimer was cloned in the pGemT PCR cloning vector. The Fc insert fragment was excised from pGemT with XbaI and BamHI restriction enzymes and ligated with AD2-pdHL2 vector that was prepared by digestion of h679-Fab-AD2-pdHL2 with XbaI and BamHI, to generate the shuttle vector Fc-AD2-pdHL2.

To convert any IgG-pdHL2 expression vector to a C—H-AD2-IgG-pdHL2 expression vector, an 861 bp BsrGI/NdeI restriction fragment is excised from the former and replaced with a 952 bp BsrGI/NdeI restriction fragment excised from the Fc-AD2-pdHL2 vector. BsrGI cuts in the CH3 domain and NdeI cuts downstream (3') of the expression cassette.

Example 14

Production of C—H-AD2-hLL2 IgG

Epratuzumab, or hLL2 IgG, is a humanized anti-human CD22 MAb. An expression vector for C—H-AD2-hLL2 IgG was generated from hLL2 IgG-pdHL2, as described above and used to transfect Sp2/0 myeloma cells by electroporation. Following transfection, the cells were plated in 96-well plates and transgenic clones were selected in media containing methotrexate. Clones were screened for C—H-AD2-hLL2 IgG productivity by a sandwich ELISA using 96-well microtitre plates coated with an hLL2-specific anti-idiotype MAb and detection with peroxidase-conjugated anti-human IgG. Clones were expanded to roller bottles for protein production and C—H-AD2-hLL2 IgG was purified from the spent culture media in a single step using Protein-A affinity chromatography. SE-HPLC analysis resolved two protein peaks (not shown). The retention time of the slower eluted peak (8.63 min) was similar to hLL2 IgG. The retention time of the faster eluted peak (7.75 min) was consistent with a ~300 kDa protein. It was later determined that this peak represents disulfide linked dimers of C—H-AD2-hLL2-IgG. This dimer is reduced to the monomeric form during the DNL reaction. SDS-PAGE analysis demonstrated that the purified C—H-AD2-hLL2-IgG consisted of both monomeric and disulfide-linked dimeric forms of the module (not shown). Protein bands representing these two forms were evident by SDS-PAGE under non-reducing conditions, while under reducing conditions all of the forms were reduced to two bands representing the constituent polypeptides (Heavy chain-AD2 and kappa chain) (not shown). No other contaminating bands were detected.

Example 15

Production of C—H-AD2-hA20 IgG hA20 IgG is a humanized anti-human CD20 MAb. An expression vector for C—H-AD2-hA20 IgG was generated from hA20 IgG-pDHL2, and used to transfect Sp2/0 myeloma cells by electroporation. Following transfection, the cells were plated in 96-well plates and transgenic clones were selected in media containing methotrexate. Clones were screened for C—H-AD2-hA20 IgG productivity by a sandwich ELISA using 96-well microtitre plates coated with an hA20-specific anti-idiotype MAb and detection with peroxidase-conjugated anti-human IgG. Clones were expanded to roller bottles for protein production and C—H-AD2-hA20 IgG was purified from the spent culture media in a single step using Protein-A affinity chromatography. SE-HPLC and SDS-PAGE analyses gave very similar results to those obtained for C—H-AD2-hLL2 IgG (not shown).

Example 16

Production of AD- and DDD-linked Fab and IgG Fusion Proteins From Multiple Antibodies Using the techniques described in the preceding Examples, the following IgG or Fab fusion proteins were constructed and incorporated into DNL constructs. The fusion proteins retained the antigen-binding characteristics of the parent antibodies and the DNL constructs exhibited the antigen-binding activities of the incorporated antibodies or antibody fragments.

TABLE 3

Fusion proteins comprising IgG or Fab Moieties

| Fusion Protein | Binding Specificity |
|---|---|
| C-AD1-Fab-h679 | HSG |
| C-AD2-Fab-h679 | HSG |
| C-(AD2)$_2$-Fab-H679 | HSG |
| C-AD2-IgG-h734 | Indium-DTPA |
| C-AD2-IgG-hA20 | CD20 |
| C-AD2-IgG-hA20L | CD20 |
| C-AD2-IgG-hL243 | HLA-DR |
| C-AD2-IgG-hLL2 | CD22 |
| N-AD2-IgG-hLL2 | CD22 |
| C-AD2-IgG-hMN-14 | CEA |
| C-AD2-IgG-hR1 | IGF-1R |
| C-AD2-IgG-hRS7 | EGP-1 |
| C-AD2-IgG-hPAM4 | MUC1 |
| C-AD2-IgG-hLL1 | CD74 |
| C-DDD1-Fab-hMN-14 | CEACAM5 |
| C-DDD2-Fab-hMN-14 | CEACAM5 |
| C-DDD2-Fab-h679 | |
| C-DDD2-Fab-hA19 | CD19 |
| C-DDD2-Fab-hA20 | CD20 |
| C-DDD2-Fab-hAFP | AFP |
| C-DDD2-Fab-hL243 | HLA-DR |
| C-DDD2-Fab-hLL1 | CD74 |
| C-DDD2-Fab-hLL2 | CD22 |
| C-DDD2-Fab-hMN-3 | CEACAM6 |
| C-DDD2-Fab-hMN-15 | CEACAM6 |
| C-DDD2-Fab-hPAM4 | MUC1 |
| C-DDD2-Fab-hR1 | IGF-1R |
| C-DDD2-Fab-hRS7 | IGP-1 |
| N-DDD2-Fab-hMN-14 | CEACAM5 |

Example 17

Ribonuclease Based DNL Immunotoxins Comprising Quadruple Ranpirnase (Rap) Conjugated to B-Cell Lymphoma-Targeting Antibodies We applied the Dock-and-Lock (DNL) method to generate a novel class of immunotoxins, each of which comprises four copies of Rap site-specifically linked to a bivalent IgG. We combined a recombinant Rap-DDD module, produced in *E. coli*, with recombinant, humanized IgG-AD modules, which were produced in myeloma cells and target B-cell lymphomas and leukemias via binding to CD20 (hA20, veltuzumab), CD22 (hLL2, epratuzumab) or HLA-DR (hL243, IMMU-114), to generate 20-Rap, 22-Rap and C2-Rap, respectively. For each construct, a dimer of Rap was covalently tethered to the C-terminus of each heavy chain of the respective IgG. A control construct, 14-Rap, was made similarly, using labetuzumab (hMN-14), that binds to an antigen (CEACAM5) not expressed on B-cell lymphomas/leukemias.

Rap-DDD2
(SEQ ID NO: 98)
pQDWLTFQKKHITNTRDVDCDNIMSTNLFHCKDKNTFIYSRPEPVKAIC

KGIIASKNVLTTSEFYLSDCNVTSRPCKYKLKKSTNKFCVTCENQAPVH

FVGVGSCGGGGSLECGHIQIPPGLTELLQGYTVEVLRQQPPDLVEFAVE

YFTRLREARAVEHHHHHH

The deduced amino acid sequence of secreted Rap-DDD2 is shown above (SEQ ID NO:98). Rap, underlined; linker, italics; DDD2, bold; pQ, amino-terminal glutamine converted to pyroglutamate. Rap-DDD2 was produced in *E. coli* as inclusion bodies, which were purified by IMAC under denaturing conditions, refolded and then dialyzed into PBS before purification by Q-Sepharose anion exchange chromatography. SDS-PAGE under reducing conditions resolved a protein band with a Mr appropriate for Rap-DDD2 (18.6 kDa) (not shown). The final yield of purified Rap-DDD2 was 10 mg/L of culture.

The DNL method was employed to rapidly generate a panel of IgG-Rap conjugates. The IgG-AD modules were expressed in myeloma cells and purified from the culture supernatant using Protein A affinity chromatography. The Rap-DDD2 module was produced and mixed with IgG-AD2 to form a DNL complex. Since the CH3-AD2-IgG modules possess two AD2 peptides and each can tether a Rap dimer, the resulting IgG-Rap DNL construct comprises four Rap groups and one IgG. IgG-Rap is formed nearly quantitatively from the constituent modules and purified to near homogeneity with Protein A.

Prior to the DNL reaction, the CH$_3$-AD2-IgG exists as both a monomer, and a disulfide-linked dimer (not shown). Under non-reducing conditions, the IgG-Rap resolves as a cluster of high molecular weight bands of the expected size between those for monomeric and dimeric CH$_3$-AD2-IgG (not shown). Reducing conditions, which reduces the conjugates to their constituent polypeptides, shows the purity of the IgG-Rap and the consistency of the DNL method, as only bands representing heavy-chain-AD2 (HC-AD2), kappa light chain and Rap-DDD2 are visualized (not shown).

Reversed phase HPLC analysis of 22-Rap (not shown) resolved a single protein peak at 9.10 min eluting between the two peaks of CH$_3$-AD2-IgG-hLL2, representing the monomeric (7.55 min) and the dimeric (8.00 min) forms. The Rap-DDD2 module was isolated as a mixture of dimer and tetramer (reduced to dimer during DNL), which were eluted at 9.30 and 9.55 min, respectively (not shown).

LC/MS analysis of 22-Rap was accomplished by coupling reversed phase HPLC using a C8 column with ESI-TOF mass spectrometry (not shown). The spectrum of unmodified 22-Rap identifies two major species, having either two G0F (G0F/G0F) or one G0F plus one G1F (G0F/G1F) N-linked glycans, in addition to some minor glycoforms (not shown). Enzymatic deglycosylation resulted in a single deconvoluted mass consistent with the calculated mass of 22-Rap (not shown). The resulting spectrum following reduction with TCEP identified the heavy chain-AD2 polypeptide modified with an N-linked glycan of the G0F or G1F structure as well as additional minor forms (not shown). Each of the three subunit polypeptides comprising 22-Rap were identified in the deconvoluted spectrum of the reduced and deglycosylated sample (not shown). The results confirm that both the Rap-DDD2 and HC-AD2 polypeptides have an amino terminal glutamine that is converted to pyroglutamate (pQ); therefore, 22-Rap has 6 of its 8 constituent polypeptides modified by pQ.

Figure 13:
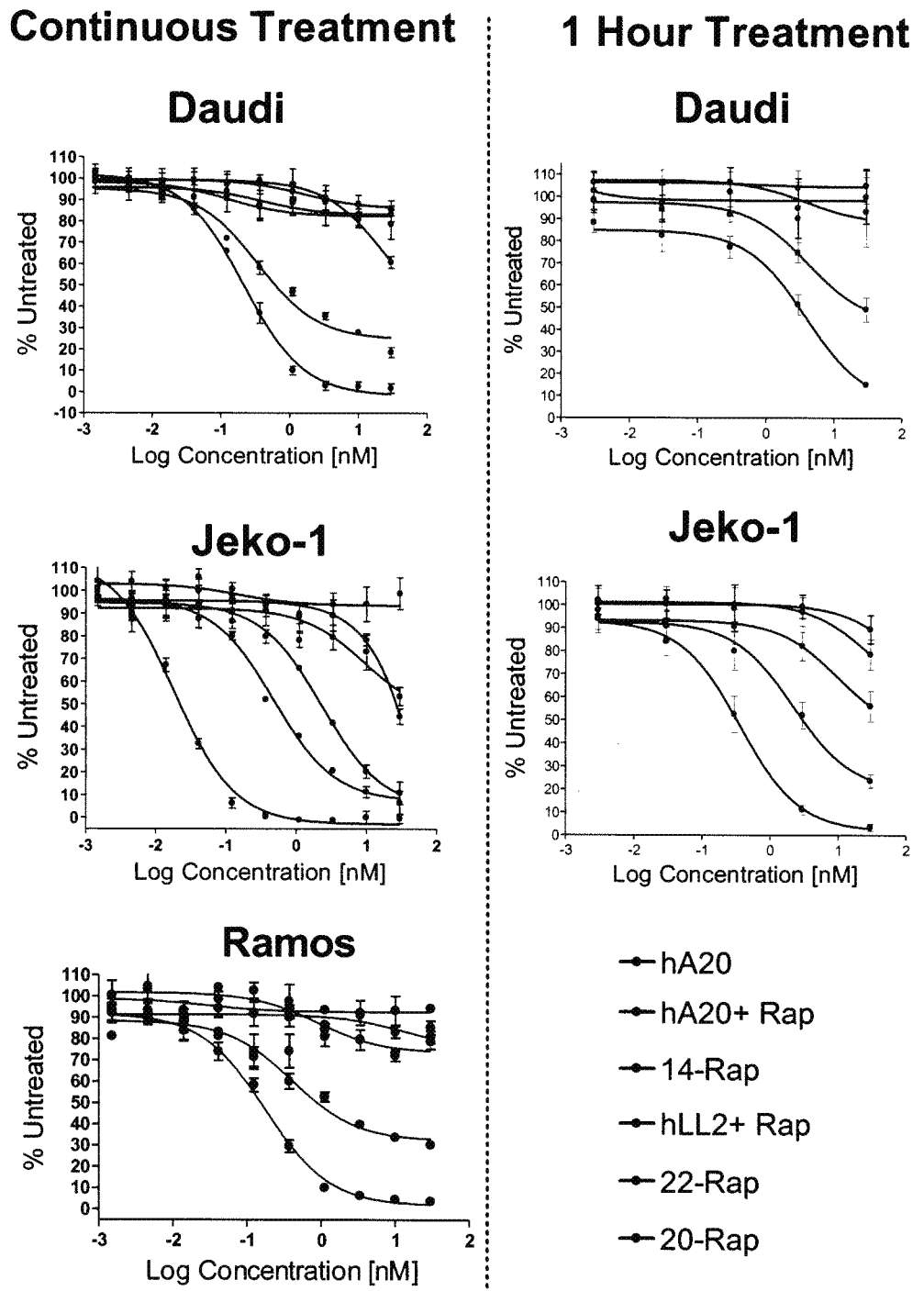
FIG. 13 shows in vitro cytotoxicity of DNL-Rap immunotoxin constructs either treated continuously with immunotoxin or with washing after a 1 hour treatment.

In vitro cytotoxicity was evaluated in three NHL cell lines. Each cell line expresses CD20 at a considerably higher surface density compared to CD22; however, the internalization rate for hLL2 (anti-CD22) is much faster than hA20 (anti-CD20). 14-Rap shares the same structure as 22-Rap and 20-Rap, but its antigen (CEACAM5) is not expressed by the NHL cells. In FIG. 13, Left panel: Cells were treated continuously with IgG-Rap as single agents or with combinations of the parental MAbs plus rRap. Both 20-Rap and 22-Rap killed each cell line at concentrations above 1 nM, indicating that their action is cytotoxic as opposed to merely cytostatic. 20-Rap was the most potent IgG-Rap, suggesting that antigen density may be more important than internalization rate. Similar results were obtained for Daudi and Ramos, where 20-Rap ($EC_{50}$~0.1 nM) was 3-6-fold more potent than 22-Rap. The rituximab-resistant mantle cell lymphoma line, Jeko-1, exhibits increased CD20 but decreased CD22, compared to Daudi and Ramos. Importantly, 20-Rap exhibited very potent cytotoxicity ($EC_{50}$~20 µM) in Jeko-1, which was 25-fold more potent than 22-Rap.

As shown in FIG. 13. Right panel: Expectedly, washing the cells after 1-h treatment significantly decreased the cytotoxicity (~50-fold) of each agent. Again, 20-Rap was the most potent, suggesting that its slower internalization rate is not limiting. 14-Rap shows increased cytotoxicity compared to rRap (in combination with MAbs), indicating that the quadruple Rap structure of the IgG-Rap may enhance its internalization. Washing after the 1-h incubation reduced the cytotoxicity of 14-Rap more than the targeting 22-Rap and 20-Rap.

Figure 14:
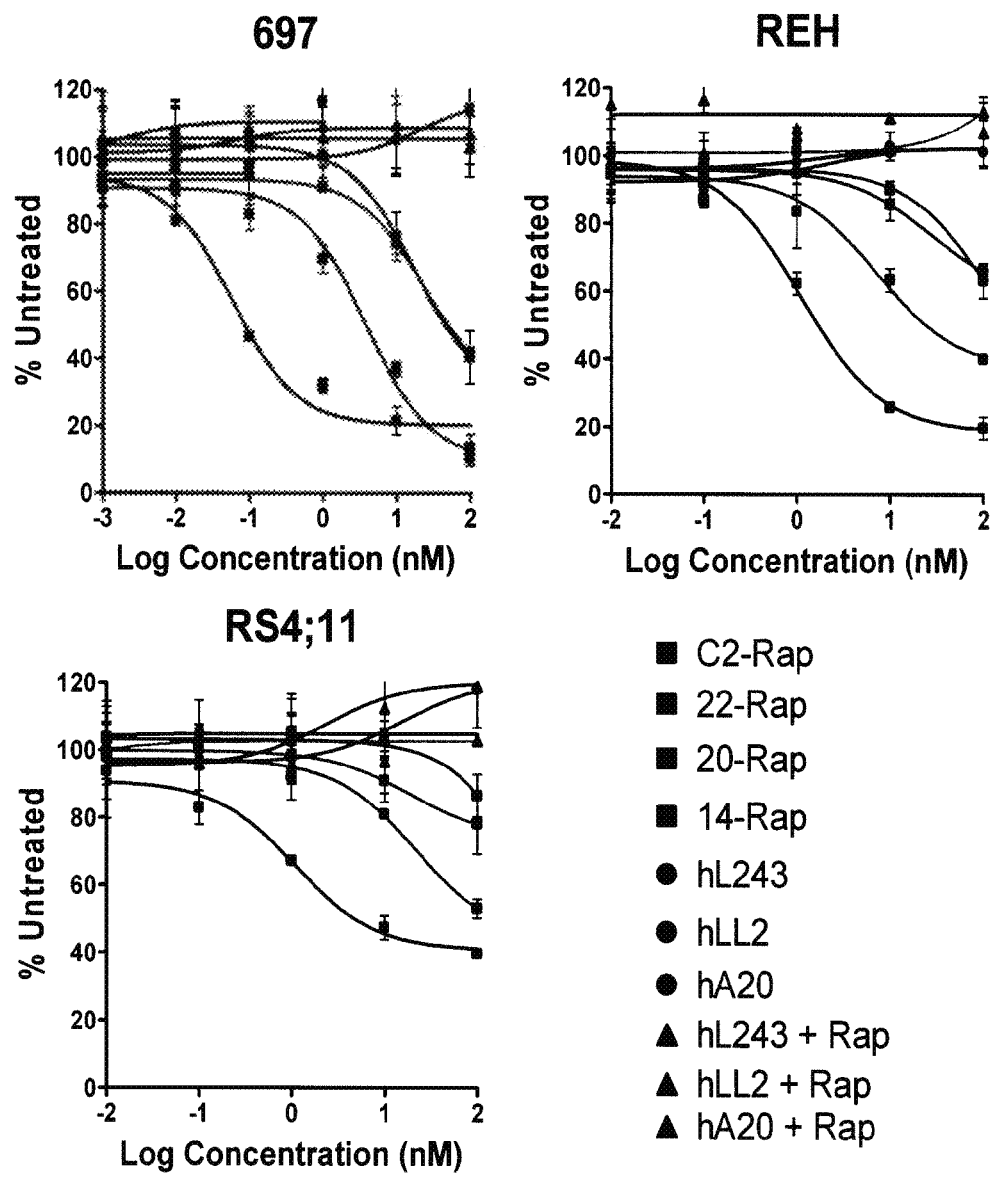
FIG. 14 shows in vitro cytotoxicity of DNL-Rap immunotoxin constructs in ALL cell lines.

IgG-Rap was evaluated with three ALL cell lines (FIG. 14). The relative antigen density was similar among the three lines, with HLA-DR>>CD22> CD20. None of the parental MAbs, either alone or combined with rRap, were cytotoxic in these assays. However, the non-targeting 14-Rap showed some activity, similar to the results with NHL lines. For each cell line, C2-Rap, which targets the most abundant antigen (HLA-DR), gave the most potent response, which was ~50-fold greater than 22-Rap. For the ALL lines, which have very low CD20 antigen density, 20-Rap showed modest cytotoxicity, which was similar to that of the non-targeting 14-Rap. This is in contrast to the results for the NHL lines, which have high CD20 density and were most responsive to 20-Rap. Thus, the efficacy of IgG-Rap correlates with the relative abundance of the targeted antigen.

CONCLUSIONS

The DNL method provides a modular approach to efficiently tether multiple cytotoxins onto a targeting antibody, resulting in novel immunotoxins that are expected to show higher in vivo potency due to improved pharmacokinetics and targeting specificity. LC/MS, RP-HPLC and SDS-PAGE demonstrated the homogeneity and purity of IgG-Rap. Targeting Rap with a MAb to a cell surface antigen enhanced its tumor-specific cytotoxicity. Antigen density and internalization rate are both critical factors for the observed in vitro potency of IgG-Rap. In vitro results show that CD20-, CD22-, or HLA-DR-targeted IgG-Rap have potent biologic activity for therapy of B-cell lymphomas and leukemias.

Example 18

High Potency of a Rap-anti-Trop-2 IgG DNL Construct Against Carcinomas

Using the same techniques described in Example 17, an E1-Rap DNL construct, comprising hRS7-IgG-Ad2 (anti-Trop-2) linked to four copies of Rap-DDD2 was produced and showed potent in vitro growth inhibitory properties against a variety of carcinoma cell lines (not shown). In breast (MDA-MB-468), cervical (ME-180), and pancreatic (BxPC-3 and Capan-1) tumor lines, all of which express high levels of Trop-2, E1-Rap was very potent, showing $EC_{50}$ in the subnanomolar range (5 to 890 µM), which was 1,000- to 100.00-fold higher than untargeted Rap or the combination of Rap and hRS7. In cell lines expressing moderate levels of Trop-2, such as the three prostate cancer lines (PC-3, DU 145, and LNCaP), E1-Rap was less potent, but still showed $EC_{50}$ in the nanomolar range (1 to 890 nM). The cell binding data obtained for these solid cancer cell lines suggest that the sensitivity of a cell line to E1-Rap appears to correlate with its Trop-2 expression on the cell surface. No toxicity was observed for E1-Rap in the prostate cancer line, 22Rv1, which fails to bind hRS7. These results show the efficacy of E1-Rap as a new therapeutic for Trop-2-positive solid tumors, including breast, colon, stomach, lung, ovarian, endometrial, cervical, pancreatic, and prostatic carcinomas.

All of the COMPOSITIONS and METHODS disclosed and claimed herein can be made and used without undue experimentation in light of the present disclosure. While the compositions and methods have been described in terms of preferred embodiments, it is apparent to those of skill in the art that variations maybe applied to the COMPOSITIONS and METHODS and in the steps or in the sequence of steps of the METHODS described herein without departing from the concept, spirit and scope of the invention. More specifically, certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A complex comprising:
   a) a first fusion protein comprising a toxin attached to a DDD (dimerization and docking domain) moiety from human protein kinase A (PKA) regulatory subunit RIα, RIβ, RIIα or RIIβ, wherein the toxin is selected from the group consisting of ranpirnase (Rap), saporin, diphtheria toxin, gelonin, Pseudomonas exotoxin; and
   b) a second fusion protein comprising an antibody or antigen binding antibody fragment attached to an AD (anchoring domain) moiety from an AKAP protein, wherein the antibody or antibody fragment is selected from the group consisting of hR1 (anti-IGF-1R), hPAM4 (anti-mucin), hA20 (anti-CD20), hLL1 (anti-CD74), hLL2 (anti-CD22), hMN-14 (anti-CEA), hMN-15 (anti-CEA) and hRS7 (anti-EGP-1);

wherein two copies of the DDD moiety form a dimer that binds to the AD moiety to form the complex.

2. The complex of claim 1, wherein the antibody or antibody fragment is selected from the group consisting of an IgG, a F(ab')$_2$, a F(ab)$_2$, a Fab', a Fab, a Fv, a scFv and a dAb.

3. The complex according to claim 1, wherein the antibody or antibody fragment is selected from the group consisting of hRS7 (anti-EGP-1), hLL1 (anti-CD74), hLL2 (anti-CD22) and hA20 (anti-CD20).

\* \* \* \* \*

SEQUENCE LISTING

```
<160> NUMBER OF SEQ ID NOS: 98

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asn Tyr Gly Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp Ile Asn Thr Tyr Thr Gly Glu Pro Thr Tyr Thr Asp Asp Phe Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Phe Gly Ser Ser Tyr Trp Tyr Phe Asp Val
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Ala Ser Gln Asp Val Ser Ile Ala Val Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Ala Ser Tyr Arg Tyr Thr
1               5

<210> SEQ ID NO 6
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 6

Gln Gln His Tyr Ile Thr Pro Leu Thr
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ala Ser Ser Ser Val Ser Tyr Ile His
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Thr Ser Asn Leu Ala Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Gln Trp Thr Ser Asn Pro Pro Thr
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Tyr Asn Met His
1               5

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 11

Ala Ile Tyr Pro Gly Asn Gly Asp Thr Ser Tyr Asn Gln Lys Phe Lys
1               5                   10                  15

Gly

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Val Tyr Tyr Ser Asn Ser Tyr Trp Tyr Phe Asp Val
1               5                   10

<210> SEQ ID NO 13
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 14
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Ile Glu Tyr Leu Ala Lys Gln Ile Val Asp Asn Ala Ile Gln Gln
1               5                   10                  15

Ala

<210> SEQ ID NO 16
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 17
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ser Leu Arg Glu Cys Glu Leu Tyr Val Gln Lys His Asn Ile Gln Ala
1               5                   10                  15

Leu Leu Lys Asp Ser Ile Val Gln Leu Cys Thr Ala Arg Pro Glu Arg
            20                  25                  30

Pro Met Ala Phe Leu Arg Glu Tyr Phe Glu Arg Leu Glu Lys Glu Glu
        35                  40                  45

Ala Lys
    50

<210> SEQ ID NO 18
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Ser Cys Gly Gly Ser Leu Arg Glu Cys Glu Leu Tyr Val Gln Lys
1               5                   10                  15

His Asn Ile Gln Ala Leu Leu Lys Asp Ser Ile Val Gln Leu Cys Thr
            20                  25                  30

Ala Arg Pro Glu Arg Pro Met Ala Phe Leu Arg Glu Tyr Phe Glu Arg
        35                  40                  45

Leu Glu Lys Glu Glu Ala Lys
    50                  55

<210> SEQ ID NO 19
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Cys Gly Phe Glu Glu Leu Ala Trp Lys Ile Ala Lys Met Ile Trp Ser
1               5                   10                  15

Asp Val Phe Gln Gln Gly Cys
            20
```

```
<210> SEQ ID NO 20
<211> LENGTH: 381
<212> TYPE: PRT
<213> ORGANISM: Homo sapiens

<400> SEQUENCE: 20

Met Ala Ser Pro Pro Ala Cys Pro Ser Glu Glu Asp Glu Ser Leu Lys
1               5                   10                  15

Gly Cys Glu Leu Tyr Val Gln Leu His Gly Ile Gln Gln Val Leu Lys
            20                  25                  30

Asp Cys Ile Val His Leu Cys Ile Ser Lys Pro Glu Arg Pro Met Lys
        35                  40                  45

Phe Leu Arg Glu His Phe Glu Lys Leu Glu Lys Glu Glu Asn Arg Gln
    50                  55                  60

Ile Leu Ala Arg Gln Lys Ser Asn Ser Gln Ser Asp Ser His Asp Glu
65                  70                  75                  80

Glu Val Ser Pro Thr Pro Pro Asn Pro Val Val Lys Ala Arg Arg Arg
                85                  90                  95

Arg Gly Gly Val Ser Ala Glu Val Tyr Thr Glu Asp Ala Val Ser
            100                 105                 110

Tyr Val Arg Lys Val Ile Pro Lys Asp Tyr Lys Thr Met Thr Ala Leu
            115                 120                 125

Ala Lys Ala Ile Ser Lys Asn Val Leu Phe Ala His Leu Asp Asp Asn
        130                 135                 140

Glu Arg Ser Asp Ile Phe Asp Ala Met Phe Pro Val Thr His Ile Ala
145                 150                 155                 160

Gly Glu Thr Val Ile Gln Gln Gly Asn Glu Gly Asp Asn Phe Tyr Val
                165                 170                 175

Val Asp Gln Gly Glu Val Asp Val Tyr Val Asn Gly Glu Trp Val Thr
            180                 185                 190

Asn Ile Ser Glu Gly Gly Ser Phe Gly Glu Leu Ala Leu Ile Tyr Gly
        195                 200                 205

Thr Pro Arg Ala Ala Thr Val Lys Ala Lys Thr Asp Leu Lys Leu Trp
210                 215                 220

Gly Ile Asp Arg Asp Ser Tyr Arg Arg Ile Leu Met Gly Ser Thr Leu
225                 230                 235                 240

Arg Lys Arg Lys Met Tyr Glu Glu Phe Leu Ser Lys Val Ser Ile Leu
                245                 250                 255

Glu Ser Leu Glu Lys Trp Glu Arg Leu Thr Val Ala Asp Ala Leu Glu
            260                 265                 270

Pro Val Gln Phe Glu Asp Gly Glu Lys Ile Val Val Gln Gly Glu Pro
        275                 280                 285

Gly Asp Asp Phe Tyr Ile Ile Thr Glu Gly Thr Ala Ser Val Leu Gln
    290                 295                 300

Arg Arg Ser Pro Asn Glu Glu Tyr Val Glu Val Gly Arg Leu Gly Pro
305                 310                 315                 320

Ser Asp Tyr Phe Gly Glu Ile Ala Leu Leu Leu Asn Arg Pro Arg Ala
                325                 330                 335

Ala Thr Val Val Ala Arg Gly Pro Leu Lys Cys Val Lys Leu Asp Arg
            340                 345                 350

Pro Arg Phe Glu Arg Val Leu Gly Pro Cys Ser Glu Ile Leu Lys Arg
        355                 360                 365

Asn Ile Gln Arg Tyr Asn Ser Phe Ile Ser Leu Thr Val
    370                 375                 380
```

<210> SEQ ID NO 21
<211> LENGTH: 418
<212> TYPE: PRT
<213> ORGANISM: Homo sapiens

<400> SEQUENCE: 21

Met Ser Ile Glu Ile Pro Ala Gly Leu Thr Glu Leu Leu Gln Gly Phe
1               5                   10                  15

Thr Val Glu Val Leu Arg His Gln Pro Ala Asp Leu Leu Glu Phe Ala
            20                  25                  30

Leu Gln His Phe Thr Arg Leu Gln Gln Glu Asn Glu Arg Lys Gly Thr
        35                  40                  45

Ala Arg Phe Gly His Glu Gly Arg Thr Trp Gly Asp Leu Gly Ala Ala
    50                  55                  60

Ala Gly Gly Gly Thr Pro Ser Lys Gly Val Asn Phe Ala Glu Glu Pro
65                  70                  75                  80

Met Gln Ser Asp Ser Glu Asp Gly Glu Glu Glu Ala Ala Pro Ala
                85                  90                  95

Asp Ala Gly Ala Phe Asn Ala Pro Val Ile Asn Arg Phe Thr Arg Arg
            100                 105                 110

Ala Ser Val Cys Ala Glu Ala Tyr Asn Pro Asp Glu Glu Asp Asp
        115                 120                 125

Ala Glu Ser Arg Ile Ile His Pro Lys Thr Asp Gln Arg Asn Arg
    130                 135                 140

Leu Gln Glu Ala Cys Lys Asp Ile Leu Leu Phe Lys Asn Leu Asp Pro
145                 150                 155                 160

Glu Gln Met Ser Gln Val Leu Asp Ala Met Phe Glu Lys Leu Val Lys
                165                 170                 175

Asp Gly Glu His Val Ile Asp Gln Gly Asp Asp Gly Asp Asn Phe Tyr
            180                 185                 190

Val Ile Asp Arg Gly Thr Phe Asp Ile Tyr Val Lys Cys Asp Gly Val
        195                 200                 205

Gly Arg Cys Val Gly Asn Tyr Asp Asn Arg Gly Ser Phe Gly Glu Leu
    210                 215                 220

Ala Leu Met Tyr Asn Thr Pro Arg Ala Ala Thr Ile Thr Ala Thr Ser
225                 230                 235                 240

Pro Gly Ala Leu Trp Gly Leu Asp Arg Val Thr Phe Arg Arg Ile Ile
                245                 250                 255

Val Lys Asn Asn Ala Lys Lys Arg Lys Met Tyr Glu Ser Phe Ile Glu
            260                 265                 270

Ser Leu Pro Phe Leu Lys Ser Leu Glu Phe Ser Glu Arg Leu Lys Val
        275                 280                 285

Val Asp Val Ile Gly Thr Lys Val Tyr Asn Asp Gly Glu Gln Ile Ile
    290                 295                 300

Ala Gln Gly Asp Ser Ala Asp Ser Phe Phe Ile Val Glu Ser Gly Glu
305                 310                 315                 320

Val Lys Ile Thr Met Lys Arg Lys Gly Lys Ser Glu Val Glu Glu Asn
                325                 330                 335

Gly Ala Val Glu Ile Ala Arg Cys Ser Arg Gly Gln Tyr Phe Gly Glu
            340                 345                 350

Leu Ala Leu Val Thr Asn Lys Pro Arg Ala Ala Ser Ala His Ala Ile
        355                 360                 365

Gly Thr Val Lys Cys Leu Ala Met Asp Val Gln Ala Phe Glu Arg Leu
    370                 375                 380

```
Leu Gly Pro Cys Met Glu Ile Met Lys Arg Asn Ile Ala Thr Tyr Glu
385                 390                 395                 400

Glu Gln Leu Val Ala Leu Phe Gly Thr Asn Met Asp Ile Val Glu Pro
                405                 410                 415

Thr Ala

<210> SEQ ID NO 22
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(2)
<223> OTHER INFORMATION: Any conservative amino acid substitution
<220> FEATURE:
<221> NAME/KEY: MOD_RES
<222> LOCATION: (4)..(4)
<223> OTHER INFORMATION: Any conservative amino acid substitution
<220> FEATURE:
<221> NAME/KEY: MOD_RES
<222> LOCATION: (6)..(8)
<223> OTHER INFORMATION: Any conservative amino acid substitution
<220> FEATURE:
<221> NAME/KEY: MOD_RES
<222> LOCATION: (10)..(11)
<223> OTHER INFORMATION: Any conservative amino acid substitution
<220> FEATURE:
<221> NAME/KEY: MOD_RES
<222> LOCATION: (14)..(15)
<223> OTHER INFORMATION: Any conservative amino acid substitution
<220> FEATURE:
<221> NAME/KEY: MOD_RES
<222> LOCATION: (17)..(17)
<223> OTHER INFORMATION: Any conservative amino acid substitution
<220> FEATURE:
<221> NAME/KEY: MOD_RES
<222> LOCATION: (19)..(19)
<223> OTHER INFORMATION: Any conservative amino acid substitution
<220> FEATURE:
<221> NAME/KEY: MOD_RES
<222> LOCATION: (22)..(27)
<223> OTHER INFORMATION: Any conservative amino acid substitution
<220> FEATURE:
<221> NAME/KEY: MOD_RES
<222> LOCATION: (30)..(30)
<223> OTHER INFORMATION: Any conservative amino acid substitution
<220> FEATURE:
<221> NAME/KEY: MOD_RES
<222> LOCATION: (32)..(32)
<223> OTHER INFORMATION: Any conservative amino acid substitution
<220> FEATURE:
<221> NAME/KEY: MOD_RES
<222> LOCATION: (34)..(34)
<223> OTHER INFORMATION: Any conservative amino acid substitution
<220> FEATURE:
<221> NAME/KEY: MOD_RES
<222> LOCATION: (37)..(38)
<223> OTHER INFORMATION: Any conservative amino acid substitution
<220> FEATURE:
<221> NAME/KEY: MOD_RES
<222> LOCATION: (40)..(44)
<223> OTHER INFORMATION: Any conservative amino acid substitution

<400> SEQUENCE: 22

Xaa Xaa Ile Xaa Ile Xaa Xaa Xaa Leu Xaa Xaa Leu Leu Xaa Xaa Tyr
1               5                   10                  15

Xaa Val Xaa Val Leu Xaa Xaa Xaa Xaa Xaa Xaa Leu Val Xaa Phe Xaa
                20                  25                  30

Val Xaa Tyr Phe Xaa Xaa Leu Xaa Xaa Xaa Xaa Xaa
```

```
                        35                  40

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any conservative amino acid substitution
<220> FEATURE:
<221> NAME/KEY: MOD_RES
<222> LOCATION: (7)..(8)
<223> OTHER INFORMATION: Any conservative amino acid substitution
<220> FEATURE:
<221> NAME/KEY: MOD_RES
<222> LOCATION: (11)..(12)
<223> OTHER INFORMATION: Any conservative amino acid substitution
<220> FEATURE:
<221> NAME/KEY: MOD_RES
<222> LOCATION: (15)..(17)
<223> OTHER INFORMATION: Any conservative amino acid substitution

<400> SEQUENCE: 23

Xaa Xaa Xaa Xaa Xaa Ala Xaa Xaa Ile Val Xaa Xaa Ala Ile Xaa Xaa
1               5                   10                  15

Xaa

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Ile Glu Tyr Val Ala Lys Gln Ile Val Asp Tyr Ala Ile His Gln
1               5                   10                  15

Ala

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Ile Glu Tyr Lys Ala Lys Gln Ile Val Asp His Ala Ile His Gln
1               5                   10                  15

Ala

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Ile Glu Tyr His Ala Lys Gln Ile Val Asp His Ala Ile His Gln
1               5                   10                  15
```

Ala

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Ile Glu Tyr Val Ala Lys Gln Ile Val Asp His Ala Ile His Gln
1               5                   10                  15

Ala

<210> SEQ ID NO 28
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Pro Leu Glu Tyr Gln Ala Gly Leu Leu Val Gln Asn Ala Ile Gln Gln
1               5                   10                  15

Ala Ile

<210> SEQ ID NO 29
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Leu Ile Glu Thr Ala Ser Ser Leu Val Lys Asn Ala Ile Gln Leu
1               5                   10                  15

Ser Ile

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Leu Ile Glu Glu Ala Ala Ser Arg Ile Val Asp Ala Val Ile Glu Gln
1               5                   10                  15

Val Lys

<210> SEQ ID NO 31
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Leu Tyr Gln Phe Ala Asp Arg Phe Ser Glu Leu Val Ile Ser Glu

```
                1               5                  10                  15
Ala Leu

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Glu Gln Val Ala Asn Gln Leu Ala Asp Gln Ile Ile Lys Glu Ala
1               5                   10                  15
Thr

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Phe Glu Glu Leu Ala Trp Lys Ile Ala Lys Met Ile Trp Ser Asp Val
1               5                   10                  15
Phe

<210> SEQ ID NO 34
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Glu Leu Val Arg Leu Ser Lys Arg Leu Val Glu Asn Ala Val Leu Lys
1               5                   10                  15
Ala Val

<210> SEQ ID NO 35
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Thr Ala Glu Glu Val Ser Ala Arg Ile Val Gln Val Val Thr Ala Glu
1               5                   10                  15
Ala Val

<210> SEQ ID NO 36
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36
```

```
Gln Ile Lys Gln Ala Ala Phe Gln Leu Ile Ser Gln Val Ile Leu Glu
1               5                   10                  15

Ala Thr
```

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Leu Ala Trp Lys Ile Ala Lys Met Ile Val Ser Asp Val Met Gln Gln
1               5                   10                  15
```

<210> SEQ ID NO 38
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Asp Leu Ile Glu Glu Ala Ala Ser Arg Ile Val Asp Ala Val Ile Glu
1               5                   10                  15

Gln Val Lys Ala Ala Gly Ala Tyr
                20
```

<210> SEQ ID NO 39
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Leu Glu Gln Tyr Ala Asn Gln Leu Ala Asp Gln Ile Ile Lys Glu Ala
1               5                   10                  15

Thr Glu
```

<210> SEQ ID NO 40
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

```
Phe Glu Glu Leu Ala Trp Lys Ile Ala Lys Met Ile Trp Ser Asp Val
1               5                   10                  15

Phe Gln Gln Cys
                20
```

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
Gln Ile Glu Tyr Leu Ala Lys Gln Ile Pro Asp Asn Ala Ile Gln Gln
1               5                   10                  15

Ala

<210> SEQ ID NO 42
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Lys Gly Ala Asp Leu Ile Glu Glu Ala Ala Ser Arg Ile Val Asp Ala
1               5                   10                  15

Val Ile Glu Gln Val Lys Ala Ala Gly
            20                  25

<210> SEQ ID NO 43
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Lys Gly Ala Asp Leu Ile Glu Glu Ala Ala Ser Arg Ile Pro Asp Ala
1               5                   10                  15

Pro Ile Glu Gln Val Lys Ala Ala Gly
            20                  25

<210> SEQ ID NO 44
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 45
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Pro Glu Asp Ala Glu Leu Val Arg Thr Ser Lys Arg Leu Val Glu Asn
1               5                   10                  15

Ala Val Leu Lys Ala Val Gln Gln Tyr
            20                  25

<210> SEQ ID NO 46
<211> LENGTH: 25
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 46

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 47
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Pro Glu Asp Ala Glu Leu Val Arg Leu Ser Lys Arg Leu Pro Glu Asn
1               5                   10                  15

Ala Val Leu Lys Ala Val Gln Gln Tyr
            20                  25

<210> SEQ ID NO 48
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Pro Glu Asp Ala Glu Leu Val Arg Leu Ser Lys Arg Leu Pro Glu Asn
1               5                   10                  15

Ala Pro Leu Lys Ala Val Gln Gln Tyr
            20                  25

<210> SEQ ID NO 49
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Pro Glu Asp Ala Glu Leu Val Arg Leu Ser Lys Arg Leu Val Glu Asn
1               5                   10                  15

Ala Val Glu Lys Ala Val Gln Gln Tyr
            20                  25

<210> SEQ ID NO 50
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Glu Glu Gly Leu Asp Arg Asn Glu Glu Ile Lys Arg Ala Ala Phe Gln
1               5                   10                  15

Ile Ile Ser Gln Val Ile Ser Glu Ala
            20                  25
```

<210> SEQ ID NO 51
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Leu Val Asp Asp Pro Leu Glu Tyr Gln Ala Gly Leu Leu Val Gln Asn
1               5                   10                  15

Ala Ile Gln Gln Ala Ile Ala Glu Gln
            20                  25

<210> SEQ ID NO 52
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Tyr Glu Thr Leu Leu Ile Glu Thr Ala Ser Ser Leu Val Lys Asn
1               5                   10                  15

Ala Ile Gln Leu Ser Ile Glu Gln Leu
            20                  25

<210> SEQ ID NO 53
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Leu Glu Lys Gln Tyr Gln Glu Gln Leu Glu Glu Val Ala Lys Val
1               5                   10                  15

Ile Val Ser Met Ser Ile Ala Phe Ala
            20                  25

<210> SEQ ID NO 54
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asn Thr Asp Glu Ala Gln Glu Glu Leu Ala Trp Lys Ile Ala Lys Met
1               5                   10                  15

Ile Val Ser Asp Ile Met Gln Gln Ala
            20                  25

<210> SEQ ID NO 55
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

```
Val Asn Leu Asp Lys Lys Ala Val Leu Ala Glu Lys Ile Val Ala Glu
1               5                   10                  15

Ala Ile Glu Lys Ala Glu Arg Glu Leu
            20                  25

<210> SEQ ID NO 56
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asn Gly Ile Leu Glu Leu Glu Thr Lys Ser Ser Lys Leu Val Gln Asn
1               5                   10                  15

Ile Ile Gln Thr Ala Val Asp Gln Phe
            20                  25

<210> SEQ ID NO 57
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Thr Gln Asp Lys Asn Tyr Glu Asp Glu Leu Thr Gln Val Ala Leu Ala
1               5                   10                  15

Leu Val Glu Asp Val Ile Asn Tyr Ala
            20                  25

<210> SEQ ID NO 58
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Glu Thr Ser Ala Lys Asp Asn Ile Asn Ile Glu Glu Ala Ala Arg Phe
1               5                   10                  15

Leu Val Glu Lys Ile Leu Val Asn His
            20                  25

<210> SEQ ID NO 59
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any conservative amino acid substitution
<220> FEATURE:
<221> NAME/KEY: MOD_RES
<222> LOCATION: (4)..(4)
<223> OTHER INFORMATION: Any conservative amino acid substitution
<220> FEATURE:
<221> NAME/KEY: MOD_RES
<222> LOCATION: (7)..(7)
<223> OTHER INFORMATION: Any conservative amino acid substitution
<220> FEATURE:
```

```
<221> NAME/KEY: MOD_RES
<222> LOCATION: (10)..(10)
<223> OTHER INFORMATION: Any conservative amino acid substitution
<220> FEATURE:
<221> NAME/KEY: MOD_RES
<222> LOCATION: (18)..(18)
<223> OTHER INFORMATION: Any conservative amino acid substitution
<220> FEATURE:
<221> NAME/KEY: MOD_RES
<222> LOCATION: (23)..(23)
<223> OTHER INFORMATION: Any conservative amino acid substitution
<220> FEATURE:
<221> NAME/KEY: MOD_RES
<222> LOCATION: (26)..(26)
<223> OTHER INFORMATION: Any conservative amino acid substitution
<220> FEATURE:
<221> NAME/KEY: MOD_RES
<222> LOCATION: (33)..(34)
<223> OTHER INFORMATION: Any conservative amino acid substitution
<220> FEATURE:
<221> NAME/KEY: MOD_RES
<222> LOCATION: (37)..(38)
<223> OTHER INFORMATION: Any conservative amino acid substitution
<220> FEATURE:
<221> NAME/KEY: MOD_RES
<222> LOCATION: (40)..(40)
<223> OTHER INFORMATION: Any conservative amino acid substitution
<220> FEATURE:
<221> NAME/KEY: MOD_RES
<222> LOCATION: (42)..(42)
<223> OTHER INFORMATION: Any conservative amino acid substitution
<220> FEATURE:
<221> NAME/KEY: MOD_RES
<222> LOCATION: (44)..(44)
<223> OTHER INFORMATION: Any conservative amino acid substitution

<400> SEQUENCE: 59

Xaa His Ile Xaa Ile Pro Xaa Gly Leu Xaa Glu Leu Leu Gln Gly Tyr
1               5                   10                  15

Thr Xaa Glu Val Leu Arg Xaa Gln Pro Xaa Asp Leu Val Glu Phe Ala
            20                  25                  30

Xaa Xaa Tyr Phe Xaa Xaa Leu Xaa Glu Xaa Arg Xaa
        35                  40

<210> SEQ ID NO 60
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gln Lys Ser Leu Ser Leu Ser Pro Gly Leu Gly Ser Gly Gly Gly Gly
1               5                   10                  15

Ser Gly Gly Cys Gly
            20

<210> SEQ ID NO 61
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Lys Ser Leu Ser Leu Ser Pro Gly Ala Gly Ser Gly Gly Gly Gly
1               5                   10                  15

Ser Gly Gly Cys Gly
```

```
<210> SEQ ID NO 62
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Lys Ser Leu Ser Leu Ser Pro Gly Gly Ser Gly Gly Gly Gly Ser
1               5                   10                  15

Gly Gly Cys Gly
            20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gaacctcgcg gacagttaag                                                  20

<210> SEQ ID NO 64
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ggatcctccg ccgccgcagc tcttaggttt cttgtccacc ttggtgttgc tgg            53

<210> SEQ ID NO 65
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gly Ser Gly Gly Gly Gly Ser Gly Gly Gly Gly Ser His Ile Gln Ile
1               5                   10                  15

Pro Pro Gly Leu Thr Glu Leu Leu Gln Gly Tyr Thr Val Glu Val Leu
                20                  25                  30

Arg Gln Gln Pro Pro Asp Leu Val Glu Phe Ala Val Glu Tyr Phe Thr
            35                  40                  45

Arg Leu Arg Glu Ala Arg Ala
        50                  55

<210> SEQ ID NO 66
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
```

```
gtggcgggtc tggcggaggt ggcagccaca tccagatccc gccggggctc acggagctgc    60
tgcagggcta cacggtggag gtgctgcgac ag                                  92
```

<210> SEQ ID NO 67
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67

```
gcgcgagctt ctctcaggcg ggtgaagtac tccactgcga attcgacgag gtcaggcggc    60
tgctgtcgca gcacctccac cgtgtagccc tg                                  92
```

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68

```
ggatccggag gtggcgggtc tggcggaggt                                     30
```

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69

```
cggccgtcaa gcgcgagctt ctctcaggcg                                     30
```

<210> SEQ ID NO 70
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

```
Gly Ser Gly Gly Gly Gly Ser Gly Gly Gly Gly Ser Gln Ile Glu Tyr
1               5                   10                  15

Leu Ala Lys Gln Ile Val Asp Asn Ala Ile Gln Gln Ala
            20                  25
```

<210> SEQ ID NO 71
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71

```
ggatccggag gtggcgggtc tggcggaggt ggcagccaga tcgagtacct ggccaagcag    60
atcgtggaca acgccatcca gcaggcctga cggccg                              96
```

<210> SEQ ID NO 72

```
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
cggccgtcag gcctgctgga tggcgttgtc cacgatctgc ttggccaggt actcgatctg      60
gctgccacct ccgccagacc cgccacctcc ggatcc                               96

<210> SEQ ID NO 73
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ggatccggag gtggcgggtc tggcggaggt                                      30

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
cggccgtcag gcctgctgga tg                                              22

<210> SEQ ID NO 75
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ccatgggcag ccacatccag atcccgcc                                        28

<210> SEQ ID NO 76
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ggatccgcca cctccagatc ctccgccgcc agcgcgagct tctctcaggc gggtg          55

<210> SEQ ID NO 77
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ggatccggcg gaggtggctc tgaggtccaa ctggtggaga gcgg                      44
```

```
<210> SEQ ID NO 78
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cggccgtcag cagctcttag gtttcttgtc                                    30

<210> SEQ ID NO 79
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
catgtgcggc cacatccaga tcccgccggg gctcacggag ctgctgca                48

<210> SEQ ID NO 80
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gcagctccgt gagccccggc gggatctgga tgtggccgca                         40

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Gly Gly Gly Ser Gly Gly Gly Cys Gly
1               5                   10

<210> SEQ ID NO 82
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gatccggagg tggcgggtct ggcggaggtt gcggccacat ccagatcccg ccggggctca   60
cggagctgct gca                                                      73

<210> SEQ ID NO 83
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gcagctccgt gagccccggc gggatctgga tgtggccgca acctccgcca gacccgccac   60
```

```
ctccg                                                                65
```

<210> SEQ ID NO 84
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84

```
gatccggagg tggcgggtct ggcggatgtg gccagatcga gtacctggcc aagcagatcg    60
tggacaacgc catccagcag gccggctgct gaa                                 93
```

<210> SEQ ID NO 85
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85

```
ttcagcagcc ggcctgctgg atggcgttgt ccacgatctg cttggccagg tactcgatct    60
ggccacatcc gccagacccg ccacctccg                                      89
```

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86

```
agatctggcg cacctgaact cctg                                           24
```

<210> SEQ ID NO 87
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87

```
gaattcggat cctttacccg gagacaggga gag                                 33
```

<210> SEQ ID NO 88
<211> LENGTH: 139
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88

```
tggctaacgt ttcagaagaa acatatcacg aatacacgag atgtagactg ggacaatata    60
atgtctacga atctgtttca ctgtaaggat aagaatacct ttatatacag tcggccagag   120
cctgtaaagg ctatctgta                                                139
```

<210> SEQ ID NO 89
<211> LENGTH: 39

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
aagcttcata tgcaggattg gctaacgttt cagaagaaa                                 39

<210> SEQ ID NO 90
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
cttactcgcg ataatgcctt tacagatagc ctttacaggc tctg                           44

<210> SEQ ID NO 91
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
tgctgactac ttccgagttc tatctgtccg attgcaatgt gacttcacgg ccctgcaaat          60
ataagctgaa gaaaagcact aacaaatttt gcgtaacttg cgagaaccag gctcctgtac         120
atttcgttgg agtcggg                                                        137

<210> SEQ ID NO 92
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
attatcgcga gtaagaacgt gctgactact tccgagttct at                             42

<210> SEQ ID NO 93
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ttaggatcct tagcagctcc cgactccaac gaaatgtac                                 39

<210> SEQ ID NO 94
<211> LENGTH: 9
<212> TYPE: PRT
<213> ORGANISM: Pseudomonas sp.

<400> SEQUENCE: 94

Thr Arg His Arg Gln Pro Arg Gly Trp
1               5

<210> SEQ ID NO 95
```

<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ser Thr Tyr Tyr Gly Gly Asp Trp Tyr Phe Asp Val
1               5                   10

<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Gly Gly Gly Ser
1               5

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Gly Gly Gly Ser Gly Gly Gly Gly Ser
1               5                   10

<210> SEQ ID NO 98
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Pyroglutamate

<400> SEQUENCE: 98

Gln Asp Trp Leu Thr Phe Gln Lys Lys His Ile Thr Asn Thr Arg Asp
1               5                   10                  15

Val Asp Cys Asp Asn Ile Met Ser Thr Asn Leu Phe His Cys Lys Asp
                20                  25                  30

Lys Asn Thr Phe Ile Tyr Ser Arg Pro Glu Pro Val Lys Ala Ile Cys
            35                  40                  45

Lys Gly Ile Ile Ala Ser Lys Asn Val Leu Thr Thr Ser Glu Phe Tyr
        50                  55                  60

Leu Ser Asp Cys Asn Val Thr Ser Arg Pro Cys Lys Tyr Lys Leu Lys
65                  70                  75                  80

Lys Ser Thr Asn Lys Phe Cys Val Thr Cys Glu Asn Gln Ala Pro Val
                85                  90                  95

His Phe Val Gly Val Gly Ser Cys Gly Gly Gly Ser Leu Glu Cys
                100                 105                 110

Gly His Ile Gln Ile Pro Pro Gly Leu Thr Glu Leu Leu Gln Gly Tyr
            115                 120                 125

-continued

```
Thr Val Glu Val Leu Arg Gln Gln Pro Pro Asp Leu Val Glu Phe Ala
    130                 135             140
Val Glu Tyr Phe Thr Arg Leu Arg Glu Ala Arg Ala Val Glu His His
145             150             155             160
His His His His
```